US006307056B1

(12) United States Patent
Corbett et al.

(10) Patent No.: US 6,307,056 B1
(45) Date of Patent: Oct. 23, 2001

(54) 4-ARYLOXINDOLES

(75) Inventors: Wendy Lea Corbett, Randolph; Kin-Chun Luk, North Caldwell; Paige E. Mahaney, Montclair, all of NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/464,466

(22) Filed: Dec. 15, 1999

Related U.S. Application Data

(60) Provisional application No. 60/112,590, filed on Dec. 17, 1998, and provisional application No. 60/149,028, filed on Aug. 16, 1999.

(51) Int. Cl.[7] .................. C07D 403/02; C07D 209/34; A61K 31/4178; A61K 31/404; A61N 19/02; A61N 29/00

(52) U.S. Cl. .................. 548/312.1; 514/397; 514/418; 548/486; 548/455; 548/466; 548/468

(58) Field of Search .................. 548/486, 3; 514/397

(56) References Cited

U.S. PATENT DOCUMENTS

| | | | |
|---|---|---|---|
| 4,556,672 | 12/1985 | Kadin | 514/414 |
| 5,206,261 | 4/1993 | Kawaguchi et al. | 514/418 |
| 5,322,950 | 6/1994 | Sircar et al. | 548/253 |
| 5,374,652 | 12/1994 | Buzzetti, et al. | 514/418 |
| 5,397,787 | 3/1995 | Buzzetti, et al. | 514/300 |
| 5,409,949 | 4/1995 | Buzzetti, et al. | 514/414 |
| 5,488,057 | 1/1996 | Buzzetti et al. | 514/312 |
| 5,576,330 | 11/1996 | Buzzetti et al. | 514/312 |
| 5,792,783 | 8/1998 | Tang et al. | 514/397 |
| 5,834,504 | 11/1998 | Tang et al. | 514/418 |
| 5,883,113 | 3/1999 | Tang et al. | 514/418 |
| 5,883,116 | 3/1999 | Tang et al. | 514/418 |
| 5,886,020 | 3/1999 | Tang et al. | 514/418 |

FOREIGN PATENT DOCUMENTS

| | | |
|---|---|---|
| 0436333 A2 | 12/1990 | (EP) . |
| 0580502 A1 | 7/1993 | (EP) . |
| WO 92/07830 | 5/1992 | (WO) . |
| WO 95/01349 | 1/1995 | (WO) . |
| WO 96/00226 | 1/1996 | (WO) . |
| WO 96/16964 | 6/1996 | (WO) . |
| WO 96/22976 | 8/1996 | (WO) . |
| WO 96/32380 | 10/1996 | (WO) . |
| WO 96/40116 | 12/1996 | (WO) . |
| WO 97/11692 | 4/1997 | (WO) . |
| WO 97/16447 | 5/1997 | (WO) . |
| WO 97/45409 | 12/1997 | (WO) . |
| WO 97/46551 | 12/1997 | (WO) . |
| WO 98/07695 | 2/1998 | (WO) . |
| WO 98/24432 | 6/1998 | (WO) . |
| WO 98/50356 | 11/1998 | (WO) . |
| WO 99/10325 | 3/1999 | (WO) . |
| WO 99/15500 | 4/1999 | (WO) . |
| WO 99/48868 | 9/1999 | (WO) . |
| WO 99/61422 | 12/1999 | (WO) . |
| WO 00 08202 | 2/2000 | (WO) . |
| WO 00/12084 | 3/2000 | (WO) . |

OTHER PUBLICATIONS

Abstract Acc. No. 94–028085/199404 (Abstract of EP 0580502) Adam et al.
Sun et al., J. Med. Chem., 41:2588–2603 (1998).
Sun et al., "Synthesis and Biological Evaluation of Novel 3–[(Substituted pyrrol–2–yl) methylidenyl] indolin–2–ones as Potent and Selective Inhibitors of the Flk–1/KDR Receptor Tyrosine Kinase", Abstract presented at Trip Report: ACS National Meeting, Dallas, Texas, Apr. 1998.
Mohammadi et al, Science, 276:955–960 (May 9, 1997).

*Primary Examiner*—Floyd D. Higel
(74) *Attorney, Agent, or Firm*—George W. Johnston; Patricia S. Rocha-Tramaloni

(57) ABSTRACT

Disclosed are 4-aryloxindoles that inhibit or modulate protein kinases, in particular JNK protein kinases. These compounds and their pharmaceutically acceptable salts, and prodrugs of said compounds, are useful as anti-inflammatory agents, particularly useful in the treatment of rheumatoid arthritis. Also disclosed are pharmaceutical compositions containing the foregoing compounds, as well as methods for the treatment and/or control of inflammation, particularly in the treatment or control of rheumatoid arthritis, using said compounds.

41 Claims, No Drawings

4-ARYLOXINDOLES

This application claims priority under 35 U.S.C. § 119(e) of provisional applications Ser. No. 60/112,590 filed on Dec. 17, 1998 and Ser. No. 60/149,028 filed on Aug. 16, 1999.

FIELD OF THE INVENTION

The present invention is directed to novel 4-aryloxindoles which inhibit or modulate protein kinases, in particular JNK protein kinases. These compounds and their pharmaceutically acceptable salts, and prodrugs of said compounds, are useful as anti-inflammatory agents, particularly useful in the treatment of rheumatoid arthritis. The invention is also directed to pharmaceutical compositions containing such compounds, and to methods for the treatment and/or control of inflammation, particularly in the treatment or control of rheumatoid arthritis. This invention is further directed to intermediates useful in the preparation of the foregoing compounds.

BACKGROUND OF THE INVENTION

Protein kinases are a class of proteins that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

The JNK (Jun N-terminal kinase) protein kinases (also know as "stress-activated protein kinases" or "SAPK") are members of the mitogen-activated protein (MAP) kinases. See, e.g., S. Gupta et al., EMBO J., vol. 15 no. 11 (1996) pp. 2760–2770; and Yang et al., Nature, vol. 389 (Oct. 23, 1997) pp. 865–870. At least ten JNK isoforms are currently known. See, Gupta, id. As its name indicates, one of the substrates for JNK is c-Jun. JNK phosphorylates the $NH_2$-terminal activation domain of c-Jun on Ser63 and Ser73, causing increased c-Jun transcriptional activity. See Gupta, id. In turn, c-Jun is an AP-1 transcription factor that mediates immediate-early gene expression. See, e.g., A. Minden et al., Biochimica et Biophysica Acta 1333 (1997) F85-F104; and A. Karin, Biochimica et Biophysica Acta, vol.172 (1991) pp.129–157.

The JNK protein kinase is markedly activated in response to treatment of cells with pro-inflammatory cytokines or exposure to environmental stress. JNK thus mediates the effect of extracellular stimuli on c-Jun. See Gupta, supra; and Minden, supra. Accordingly, JNK is a physiological regulator of AP-1 transcriptional activity. Thus, inhibition of JNK activity will inhibit AP-1-dependent transcription of inflammatory and immune mediators which are implicated in pathological proliferative conditions, for example inflammatory diseases and neuro-degenerative diseases, in particular, rheumatoid arthritis. See, e.g. Swantek et al., Molecular and Cellular Biology, vol. 17 (1997) pp. 6274–6282; Maroney et al., J. Neuroscience, vol. 18 (Jan. 1, 1998) pp. 104–111; and Minden, supra, at F92.

The rat homologue of JNK is also called SAPK (stress-activated protein kinase). SAPK isoforms share significant (>90%) sequence identity with the corresponding JNK isoforms [compare Kyriakis et al., Nature, Vol. 369 (May 12, 1994) pp. 156–160 and Gupta et al., supra]. Both JNK and SAPK are capable of phosphorylation of the c-Jun substrate and thus have very similar enzyme activity. JNK and SAPK are part of a protein kinase cascade that is activated by various extracellular stimuli. See e.g. Minden supra; and Kyriakis et al., BioEssays Vol. 18 (1996) pp. 567–577. JNK and SAPK each can be activated by phosphorylation on specific threonine and tyrosine residues by dual specificity MAP kinase kinases such as MKK4, SEK-1, or MKK7. See Kyriakis et al., supra; and Tournier et al., Proceedings of the National Academy of Sciences USA Vol. 94 (July 1997), pp. 7337–7342). The dual specificity MAP kinase kinases can be activated by phosphorylation on serine and/or threonine residues by MAP kinase kinase kinases such as MEKK-1. Thus, measurement of JNK or SAPK enzyme activity may be enhanced by activation by the upstream or preceding kinases. Moreover, measurement of SAPK inhibition closely correlates with JNK inhibition.

Inhibitors of protein kinase catalytic activity are known in the art. See U.S. Pat. No. 5,792,783 (3-heteroaryl-2-indolinones that modulate/inhibit tyrosine kinase signal transduction); WO 98/24432 (indoline compounds that inhibit FLK protein kinase); WO 97/45409 (substituted tetralylmethelen-oxindole analogues that inhibit tyrosine kinase). In particular, small molecule inhibitors typically block the binding of substrates by tightly interacting with the protein kinase ATP binding site (or "active site"). See WO 98/24432. It is desirable to identify small-molecule compounds that may be readily synthesized and are effective in inhibiting the catalytic activity of protein kinases, in particular of the JNK protein kinases.

Indolinone (also known as oxindole) compounds asserted to be useful in the regulating abnormal cell proliferation through tyrosine kinase inhibition are disclosed for example in WO 96/40116, WO 98/07695, WO 95/01349, WO 96/32380, WO 96/22976, WO 96/16964, WO 98/50356 (2-indolinone derivatives as modulators of protein kinase activity); Mohammadi et. al, Science, Vol. 276, May 9, 1997, pp. 955–960. Oxindole derivatives have also been described for various other therapeutic uses: U.S. Pat. No. 5,206,261 (improvement of cerebral function); WO 92/07830 (peptide antagonists); EP 580 502 A1 (antioxidants).

There continues to be a need for easily synthesized, small-molecule compounds effective in inhibiting JNK protein kinase and thus useful in the treatment or control of pathological proliferative conditions, for example inflammatory diseases and neuro-degenerative diseases, in particular, rheumatoid arthritis. It is thus an object of this invention to provide such compounds and compositions containing such compounds.

SUMMARY OF THE INVENTION

The present invention relates to 4-aryloxindoles capable of inhibiting the activity of one or more JNK protein kinases. Such compounds are useful for the treatment of inflammatory diseases and neuro-degenerative diseases. In particular, the compounds of the present invention are especially useful in the treatment or control of rheumatoid arthritis.

In one embodiment, the present invention is directed to 4-aryloxindoles having the following formula:

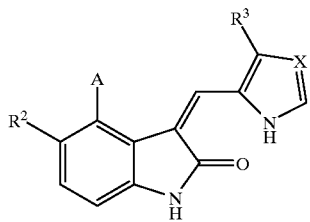

and prodrugs and pharmaceutically active metabolites of compounds of formula I, and the pharmaceutically acceptable salts of the foregoing compounds, wherein;

A is selected from the group consisting of aryl or heteroaryl, each of which optionally may be substituted by one or more substituents independently selected from the group consisting of
—H,
—$OR^4$,
—$COR^4$,
—$COOR^4$,
—$CONR^6R^7$,
—$NR^6R^7$,
—CN,
—$NO_2$,
—$SO_2R^4$,
—$SO_2NR^6R^7$,
—halogen,
—perfluoroalkyl,
lower alkyl which optionally may be substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, cycloalkyl, and heterocycle,
cycloalkyl which optionally may be substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, lower alkyl, and heterocycle, and
heterocycle which optionally may be substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, lower alkyl, and cycloalkyl;

$R^2$ is selected from the group consisting of
—H,
—$OR^4$,
—$COOR^4$,
—$CONR^6R^7$,
—$NR^6R^7$,
halogen,
—$NO_2$,
—CN,
—$SO_2NR^6R^7$,
—$SO_2R^4$
perfluoroalkyl, and
lower alkyl which optionally may be substituted by the group consisting of —$OR^8$, —$NR^6R^7$, —$COR^4$, —$COOR^4$, and —$CONR^6R^7$;

$R^3$ is selected from the group consisting of
—H,
—$OR^4$,
—$COR^4$,
—$COOR^4$,
—$CONR^6R^7$,
halogen,
—CN,
—$NR^6R^7$,
perfluoroalkyl, and
lower alkyl which optionally may be substituted by the group consisting of —$OR^8$ and —$NR^6R^7$;

$R^4$ is selected from the group consisting of
—H,
lower alkyl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$,
cycloalkyl which optionally may be substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$, and
heterocycle which optionally may be substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$;

$R^5$ is selected from the group consisting of
—H,
—$COR^8$,
—$CONR^8R^9$, and
lower alkyl which optionally may be substituted by the group consisting of —$OR^9$, —$NR^9R^{10}$, —$N(COR^9)R^{10}$, —$COR^9$, —$CONR^9R^{10}$, and —$COOR^9$;

$R^6$ and $R^7$ are each independently selected from the group consisting of
—H,
—$COR^8$,
—$COOR^8$,
—$CONR^8R^9$,
—$SO_2R^8$,
—$SO_2NR^8R^9$,
lower alkyl which optionally may be substituted by the group consisting of
—$OR^5$,
—$COOR^8$,
—$COR^8$,
—$CONR^8R^9$,
—CN,
—$NO_2$,
—$SO_2R^8$,
—$SO_2NR^8R^9$,
—$NR^8R^9$,
cycloalkyl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$,
heterocycle which optionally may be substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$,
aryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$, and
heteroaryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$,
cycloalkyl which optionally may be substituted by the group consisting of —$OR^5$, —$COOR^8$, —$COR^8$, —CONR⁸R⁹, —NR⁸R⁹, lower alkyl, heterocycle, —CN, —NO₂, —SO₂R⁸, and —SO₂NR⁸R⁹, heterocycle which optionally may be substituted by the group consisting of —OR⁵, —COOR⁸, —COR⁸, —CONR⁸R⁹, —NR⁸R⁹, lower alkyl, cycloalkyl, —CN, —NO₂, —SO₂R⁸, and —SO₂NR⁸R⁹, aryl which optionally may be substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹, and heteroaryl which optionally may be substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹;

or alternatively, —NR⁶R⁷ can optionally form a ring having 3 to 7 atoms, said ring optionally including one or more additional hetero atoms and being optionally substituted by the group consisting of one or more of lower alkyl, —OR⁵, —COR⁸, —COOR⁸, CONR⁸R⁹, and —NR⁵R⁹;

R⁸ is selected from the group consisting of

—H, lower alkyl which optionally may be substituted by the group consisting of cycloalkyl, heterocycle, aryl, heteroaryl, —OR⁹, —NR⁹R¹⁰, and —N(COR⁹)R¹⁰, aryl which optionally may be substituted by the group consisting of —OR⁹, —COOR⁹, —COR⁹, —CONR¹⁰R⁹, —NR¹⁰R⁹, lower alkyl, cycloalkyl, heterocycle, —CN, —NO₂, —SO₂R⁹, halogen, —SO₂F and —SO₂NR¹⁰R⁹, heteroaryl which optionally may be substituted by the group consisting of —OR⁹, —COOR⁹, —COR⁹, —CONR¹⁰R⁹, —NR¹⁰R⁹, lower alkyl, cycloalkyl, heterocycle, —CN, —NO₂, —SO₂R⁹, halogen, —SO₂F and —SO₂NR¹⁰R⁹, cycloalkyl which optionally may be substituted by the group consisting of —OR⁹, —COOR⁹, —COR⁹, —CONR¹⁰R⁹, —NR¹⁰R⁹, lower alkyl, heterocycle, aryl, —CN, —NO₂, —SO₂R⁹, and —SO₂NR¹⁰R⁹, and heterocycle which optionally may be substituted by the group consisting of —OR⁹, —COOR⁹, —COR⁹, —CON R¹⁰R⁹, —NR¹⁰R⁹, lower alkyl, cycloalkyl, aryl, —CN, —NO₂, —SO₂R⁹, and —SO₂NR¹⁰R⁹;

R⁹ and R¹⁰ are each independently selected from the group consisting of —H, lower alkyl and aryl; and X is selected from the group consisting of =N— and

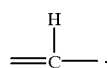

In a preferred embodiment, the present invention is directed to 4-aryloxindoles having the following formula:

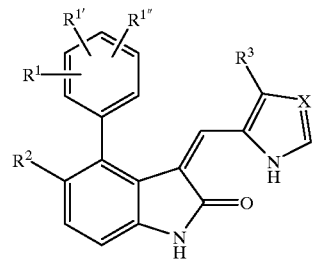

and prodrugs and pharmaceutically active metabolites of compounds of formula II, and the pharmaceutically acceptable salts of the foregoing compounds, wherein;

R¹, R¹' and R¹'' are each independently selected from the group consisting of
—H,
—OR⁴,
—COR⁴,
—COOR⁴,
—CONR⁶R⁷,
—NR⁶R⁷,
halogen,
—SO₂R⁴,
—SO₂NR⁶R⁷,
—NO₂,
—CN,
perfluoroalkyl,
lower alkyl which optionally may be substituted by the group consisting of —OR⁴, —NR⁶R⁷, —COR⁴, —COOR⁴, —OCOR⁴, —CONR⁶R⁷, —CN, —NO₂, —SO₂R⁴, —SO₂NR⁶R⁷, halogen, cycloalkyl, and heterocycle,
cycloalkyl which optionally may be substituted by the group consisting of —OR⁴, —NR⁶R⁷, —COR⁴, —COOR⁴, —OCOR⁴, —CONR⁶R⁷, —CN, —NO₂, —SO₂R⁴, —SO₂NR⁶R⁷, halogen, lower alkyl, and heterocycle, and
heterocycle which optionally may be substituted by the group consisting of —OR⁴, —NR⁶R⁷, —COR⁴, —COOR⁴, —OCOR⁴, —CONR⁶R⁷, —CN, —NO₂, —SO₂R⁴, —SO₂NR⁶R⁷, halogen, lower alkyl, and cycloalkyl; and R², R³, R⁴, R⁵, R⁶, R⁷, R⁸, R⁹, R¹⁰ and X are as defined above for formula I.

In another preferred embodiment, R³ in compounds of formula II is selected from the group consisting of
—H,
—OR⁴,
—NR⁶R⁷,
—lower alkyl which optionally may be substituted by the group consisting of —OR⁸ and —NR⁶R⁷.

In another preferred embodiment of compounds of formula I, A is heteroaryl, more particularly A is indole.

The present invention is further directed to pharmaceutical compositions comprising a pharmaceutically effective amount of any one or more of the above-described compounds and a pharmaceutically acceptable carrier or excipient.

The present invention is also directed to a method for treating and/or controlling inflammatory diseases and neurodegenerative diseases, in particular, the treatment or control of rheumatoid arthritis, by administering to a human patient in need of such therapy an effective amount of a compound according to the invention, prodrugs of such compounds and/or salts thereof.

The present invention is also directed to intermediates useful in the preparation of the above-described 4-aryloxindoles.

DETAILED DESCRIPTION OF THE INVENTION

Definitions

As used herein, the following terms shall have the following definitions.

"Aryl" means an aromatic group having 5 to 10 atoms and consisting of one or 2 rings. Examples of aryl groups include phenyl and 1- or 2-naphthyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective Amount" means an amount of at least one compound of Formula I or Formula II, or a pharmaceutically acceptable salt, prodrug or metabolite thereof, that inhibits the development or proliferation of (1) an inflammatory disease or response and/or (2) a neuro-degenerative disease or response, such as for example, and not as a limitation, rheumatoid arthritis.

"Halogen" means fluorine, chlorine, bromine or iodine.

"Heteroaryl" groups are aromatic groups having 5 to 10 atoms, one or 2 rings, and containing one or more hetero atoms. Examples of heteroaryl groups are 2-, 3- or 4-pyridyl, tetrazolyl, oxadiazolyl, pyrazinyl, indolyl and quinolyl.

"Hetero atom" means an atom selected from N, O and S.

"Heterocycle" means a 3- to 10-membered non-aromatic, partially or completely saturated hydrocarbon group, such as tetrahydroquinolyl, which contains one or two rings and at least one hetero atom.

"$IC_{50}$" refers to the concentration of a particular 4-aryloxindole or 4-heteroaryloxidole required to inhibit 50% of the SAPK protein kinase catalytic activity. $IC_{50}$ can be measured, inter alia, using the assay described herein in Example 66.

"Lower Alkyl" denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Pharmaceutically acceptable salt" refers to conventional acid-addition salts or base-addition salts which retain the biological effectiveness and properties of the compounds of formula I or formula II and are formed from suitable non-toxic organic or inorganic acids or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxide, such as for example tetramethylammonium hydroxide.

"Pharmaceutically acceptable," such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of formula I or formula II which is pharmaceutically acceptable and effective.

"Prodrug" refers to a compound that may be converted under physiological conditions or by solvolysis to any of the compounds of formula I or formula II or to a pharmaceutically acceptable salt of a compound of formula I or formula II. A prodrug may be inactive when administered to a subject but is converted in vivo to an active compound of formula I or formula II.

"Substituted," as in substituted alkyl means that the substitution can occur at one or more positions and, unless otherwise indicated, that the substituents are independently selected from the specified options.

The Compounds

In one embodiment, the present invention is directed to 4-aryloxindoles or 4-heteroaryloxindoles having the following formula:

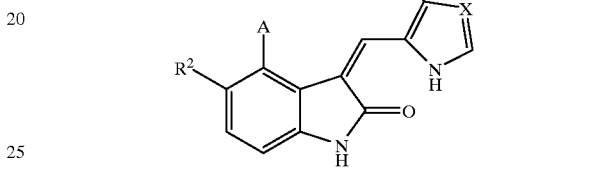

and prodrugs and pharmaceutically active metabolites of compounds of formula I, and the pharmaceutically acceptable salts of the foregoing compounds, wherein;

A is selected from the group consisting of aryl, or heteroaryl, each of which optionally may be substituted by one or more substituents independently selected from the group consisting of
—H,
—$OR^4$,
—$COR^4$,
—$COOR^4$,
—$CONR^6R^7$,
—$NR^6R^7$,
—CN,
—$NO_2$,
—$SO_2R^4$,
—$SO_2NR^6R^7$,
—halogen,
—perfluoroalkyl,
lower alkyl which optionally may be substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, cycloalkyl, and heterocycle,
cycloalkyl which optionally may be substituted by the group consisting of —$OR^4$, —$NR^6R^7$, $COR^4$, —$COOR^4$, —$OCOR^4$, —$CONR^6R^7$, —CN, —$NO_2$, —$SO_2R^4$, —$SO_2NR^6R^7$, halogen, lower alkyl, and heterocycle, and
heterocycle which optionally may be substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, lower alkyl, and cycloalkyl;

$R^2$ is selected from the group consisting of
—H,
—$OR^4$,
—$COOR^4$,
—$CONR^6R^7$,
—$NR^6R^7$, halogen,
—$NO_2$,
—CN,
—$SO_2NR^6R^7$,
—$SO_2R^4$
perfluoroalkyl, and
lower alkyl which optionally may be substituted by the group consisting of —$OR^8$, —$NR^6R^7$, —$COR^4$, —$COOR^4$, and —$CONR^6R^7$;

$R^3$ is selected from the group consisting of
—H,
—$OR^4$,
—$COR^4$,
—$COOR^4$,
—$CONR^6R^7$,
halogen,
—CN,
—$NR^6R^7$,
perfluoroalkyl, and
lower alkyl which optionally may be substituted by the group consisting of —$OR^8$ and —$NR^6R^7$;

$R^4$ is selected from the group consisting of
—H,
lower alkyl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$,
cycloalkyl which optionally may be substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$, and
heterocycle which optionally may be substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$;

$R^5$ is selected from the group consisting of
—H,
—$COR^8$,
—$CONR^8R^9$, and
lower alkyl which optionally may be substituted by the group consisting of —$OR^9$, —$NR^9R^{10}$, —$N(COR^9)R^{10}$, —$COR^9$, —$CONR^9R^{10}$, and —$COOR^9$;

$R^6$ and $R^7$ are each independently selected from the group consisting of
—H,
—$COR^8$,
—$COOR^8$,
—$CONR^8R^9$,
—$SO_2R^8$,
—$SO_2NR^8R^9$,
lower alkyl which optionally may be substituted by the group consisting of
—$OR^5$,
—$NR^8R^9$,
—$COOR^8$,
—$COR^8$,
—$CONR^8R^9$,
—CN,
—$NO_2$,
—$SO_2R^8$,
—$SO_2NR^8R^9$,
cycloalkyl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$,
heterocycle which optionally may be substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$,
aryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$, and
heteroaryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$,
cycloalkyl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$,
heterocycle which optionally may be substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$,
aryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$, and
heteroaryl which optionally may be substituted by the group consisting of —$OR^5$, —$COOR^8$, —$COR^8$, —$CONR^8R^9$, —$NR^8R^9$, lower alkyl, cycloalkyl heterocycle, —CN, —$NO_2$, —$SO_2R^8$, and —$SO_2NR^8R^9$;
or alternatively, —$NR^6R^7$ can optionally form a ring having 3 to 7 atoms, said ring optionally including one or more additional hetero atoms and being optionally substituted by the group consisting of one or more of lower alkyl, —$OR^5$, —$COR^8$, —$COOR^8$, $CONR^8R^9$, and —$NR^5R^9$;

$R^8$ is selected from the group consisting of
—H,
lower alkyl which optionally may be substituted by the group consisting of cycloalkyl, heterocycle, aryl, heteroaryl, —$OR^9$, —$NR^9R^{10}$, and —$N(COR^9)R^{10}$,
aryl which optionally may be substituted by the group consisting of —$OR^9$, —$COOR^9$, —$COR^9$, —$CONR^{10}R^9$, —$NR^{10}R^9$, lower alkyl, cycloalkyl, heterocycle, —CN, —$NO_2$, —$SO_2R^9$, halogen, —$SO_2F$ and —$SO_2NR^{10}R^9$, and
heteroaryl which optionally may be substituted by the group consisting of —$OR^9$, —$COOR^9$, —$COR^9$, —$CONR^{10}R^9$, —$NR^{10}R^9$, lower alkyl, cycloalkyl, heterocycle, —CN, —$NO_2$, —$SO_2R^9$, halogen, —$SO_2F$ and —$SO_2NR^{10}R^9$,
cycloalkyl which optionally may be substituted by the group consisting of —$OR^9$, —$COOR^9$, —$COR^9$, —$CONR^{10}R^9$, —$NR^{10}R^9$, lower alkyl, cycloalkyl, heterocycle, aryl, —CN, —$NO_2$, —$SO_2R^9$, and —$SO_2NR^{10}R^9$, and
heterocycle which optionally may be substituted by the group consisting of —$OR^9$, —$COOR^9$, —$COR^9$, —$CONR^{10}R^9$, —$NR^{10}R^9$, lower alkyl, cycloalkyl, aryl, —CN, —$NO_2$, —$SO_2R^9$, and —$SO_2NR^{10}R^9$;

$R^9$ and $R^{10}$ are each independently selected from the group consisting of —H, lower alkyl and aryl; and X is selected from the group consisting of =N— and

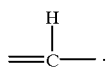

In a preferred embodiment of the compounds of formula I, A is aryl or heteroaryl, each of which optionally may be substituted by the group consisting of

—H,

—$NR^6R^7$,

—$OR^4$,

—$COR^4$,

—$COOR^4$,

—$CONR^6R^7$,

—$SO_2R^4$,

—$SO_2NR^6R^7$, and lower alkyl which optionally may be substituted by the group consisting of —$OR^5$, —$NR^6R^7$, —$COR^4$, —$COOR^4$, and —$CONR^6R^7$.

In another preferred embodiment of the compounds of formula I, $R^2$ is selected from the group consisting of —H, —$OR^4$, $NO_2$, perfluoroalkyl, —$NR^6R^7$, halogen, —$COR^4$, —$COOR^4$, —$CONR^6R^7$, and lower alkyl which optionally may be substituted by the group consisting of —$OR^8$ and —$NR^6R^7$, —$COR^4$, —$COOR^4$, and —$CONR^6R^7$. Preferred perfluoroalkyls include —$CF_3$.

In another preferred embodiment of the compounds of formula I, $R^3$ is selected from the group consisting of —H, —$OR^4$, —$NR^6R^7$, and -lower alkyl which optionally may be substituted by the group consisting of —$OR^8$ and —$NR^6R^7$.

In another preferred embodiment of the compounds of formula I, $R^4$ is selected from the group consisting of —H and lower alkyl which optionally may be substituted by the group consisting of —$OR^5$, —$COOR^8$, —$COR^8$, —$NR^6R^7$ and —$CONR^8R^9$.

In another preferred embodiment of the compounds of formula I, $R^5$ is selected from the group consisting of —$COR^8$, —$CONR^8R^9$, and lower alkyl.

In another preferred embodiment of the compounds of formula I, $R^6$ and $R^7$ are each independently selected from the group consisting of —H, —$COR^8$, —$COOR^8$, —$CONR^8R^9$, —$SO_2R^8$, aryl, heteroaryl and lower alkyl which optionally may be substituted by the group consisting of $OR^5$, and —$NR^8R^9$.

In another preferred embodiment of the compounds of formula I, $R^8$ is selected from the group consisting of —H, aryl, heteroaryl and lower alkyl which optionally may be substituted by the group consisting of aryl, heteroaryl, —$OR^9$, —$NR^9R^{10}$, and —$N(COR^9)R^{10}$.

In another preferred embodiment, the current invention is directed to compounds having the formula:

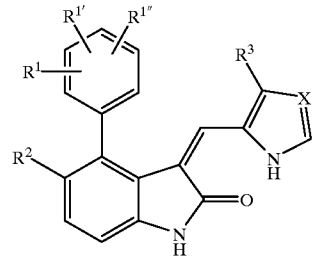

and prodrugs and pharmaceutically active metabolites of compounds of formula II, and the pharmaceutically accepted salts of the foregoing compounds, wherein;

$R^1$, $R^{1'}$ and $R^{1''}$ are each independently selected from the group consisting of
—H,
—$OR^4$,
—$COR^4$,
—$COOR^4$,
—$CONR^6R^7$,
—$NR^6R^7$,
halogen,
—$SO_2R^4$,
—$SO_2NR^6R^7$,
—$NO_2$,
—CN,
perfluoroalkyl,
lower alkyl which optionally may be substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, cycloalkyl, and heterocycle,
cycloalkyl which optionally may be substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, lower alkyl, and heterocycle, and
heterocycle which optionally may be substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, lower alkyl, and cycloalkyl; and $R^2$, $R^3$, $R^4$, $R^5$, $R^6$, $R^7$, $R^8$, $R^9$, $R^{10}$ and X are as defined above for formula I.

In a preferred embodiment of the compounds of formula II, $R^2$, $R^3$, $R^4$, $R^5$, $R^6$, $R^7$, $R^8$, $R^9$, $R^{10}$ and X are defined as above for the preferred embodiments of compounds of formula I.

In another preferred embodiment of the compounds of formula II, $R^{1'}$, $R^{1'}$ and $R^{1''}$ are each independently selected from the group consisting of

—H,
—$OR^4$,
—$COR^4$,
—$COOR^4$,
—$CONR^6R^7$,
—$NR^6R^7$,
—$SO_2R^4$,

—SO₂NR⁶R⁷, and lower alkyl which optionally may be substituted by the group consisting of —OR⁵ and —NR⁶R⁷; and R³ is selected from the group consisting of
—H,
—OR⁴,
—NR⁶R⁷,
—lower alkyl which optionally may be substituted by the group consisting of —OR⁸ and —NR⁶R⁷.

The following intermediate is useful in the synthesis of compounds of formula I:

(Z)-1,3-Dihydro-4-iodo-3-[(1H-pyrrol-2-yl)methylene]-2H-indol-2-one.

The following are examples of preferred compounds of formula I:

(Z)-1,3-Dihydro-4-phenyl-3-[(1H-pyrrol-2-yl)methylene]-2H-indol-2-one (A), (Z)-4-(3-Aminophenyl)-1,3-dihydro-3-[(1H-pyrrol-2-yl)methylene]-2H-indol-2-one (C), (Z)-4-(3-Aminophenyl)-1,3-dihydro-3-[(1H-pyrrol-2-yl)methylene]-2H-indol-2-one hydrochloride salt (D), (Z)-1,3-Dihydro-4-(4-methoxyphenyl)-3-[(1H-pyrrol-2-yl)methylene]-2H-indol-2-one (E), (Z)-1,3-Dihydro-4-(3-nitrophenyl)-3-[(1H-pyrrol-2-yl)methylene]-2H-indol-2-one (F), (Z)-1,3-Dihydro-3-[(1H-pyrrol-2-yl)methylene]-4-(3-trifluoromethylphenyl)-2H-indol-2-one (G), (Z)-1,3-Dihydro-4-(4-methylphenyl)-3-[(1H-pyrrol-2-yl)methylene]-2H-indol-2-one (H), (Z)-1,3-Dihydro-4-(2-methylphenyl)-3-[(1H-pyrrol-2-yl)methylene]-2H-indol-2-one (I), (Z)-4-(2,4-Dichlorophenyl)-1,3-dihydro-3-[(1H-pyrrol-2-yl)methylene]-2H-indol-2-one (J), (Z)-4-(4-Chlorophenyl)-1,3-dihydro-3-[(1H-pyrrol-2-yl)methylene]-2H-indol-2-one (L), (Z)-1,3-Dihydro-4-(2-methoxyphenyl)-3-[(1H-pyrrol-2-yl)methylene]-2H-indol-2-one (M), (Z)-1,3-Dihydro-4-(1-naphthalenyl)-3-[(1H-pyrrol-2-yl)methylene]-2H-indol-2-one (N), (Z)-4-(3-Chlorophenyl)-1,3-dihydro-3-[(1H-pyrrol-2-yl)methylene]-2H-indol-2-one (P), (Z)-1,3-Dihydro-4-(4-hydroxyphenyl)-3-[(1H-pyrrol-2-yl)methylene]-2H-indol-2-one (R), (Z)-4-(3-Aminophenyl)-1,3-dihydro-3-[(3-methoxy-1H-pyrrol-2-yl)methylene]-2H-indol-2-one (EE), (Z)-1,3-Dihydro-4-phenyl-3-[(3-methoxy-1H-pyrrol-2-yl)methylene]-2H-indol-2-one (GG), (Z)-1,3-Dihydro-4-(4-hydroxyphenyl)-3-[(3-methoxy-1H-pyrrol-2-yl)methylene]-2H-indol-2-one (HH), (Z)-4-[2,3-Dihydro-2-oxo-3-[(1H-pyrrol-2-yl)methylene]-1H-indol-4-yl]-benzoic acid (Q), (Z)-3-[2,3-Dihydro-2-oxo-3-[(1H-pyrrol-2-yl)methylene]-1H-indol-4-yl]-benzoic acid (BB), (Z)-4-[2,3-Dihydro-3-[(3-methoxy-1H-pyrrol-2-yl)methylene]-2-oxo-1H-indol-4-yl]-benzoic acid (II), (Z)-4-[2,3-Dihydro-3-[(3-methoxy-1H-pyrrol-2-yl)methylene]-5-nitro-2-oxo-1H-indol-4-yl]-benzoic acid methyl ester (RR), (Z)-4-[5-Amino-2,3-dihydro-3-[(3-methoxy-1H-pyrrol-2-yl)methylene]-2-oxo-1H-indol-4-yl]-benzoic acid methyl ester (SS), (Z)-4-[2,3-Dihydro-3-[(3-methoxy-1H-pyrrol-2-yl)methylene]-2-oxo-5-[(2-thienylacetyl)amino]-1H-indol-4-yl]-benzoic acid methyl ester (WW), (Z)-4-[2,3-Dihydro-3-[(3-methoxy-1H-pyrrol-2-yl)methylene]-2-oxo-5-[(2-thienylacetyl)amino]-1H-indol-4-yl]-benzoic acid (XX), (Z)-4-[2,3-Dihydro-5-fluoro-3-[(4-methyl-1H-imidazol-5-yl)methylene]-2-oxo-1H-indol-4-yl]-benzoic acid methyl ester trifluoroacetate salt (AAA), (Z)-N-[3-[2,3-Dihydro-2-oxo-3-[(1H-pyrrol-2-yl)methylene]-1H-indol-4-yl]-phenyl]-4-hydroxybenzamide (S), (Z)-N-[3-[2,3-Dihydro-2-oxo-3-[(1H-pyrrol-2-yl)methylene]-1H-indol-4-yl]-phenyl]-3-bromobenzamide (T), (Z)-N-[3-[2,3-Dihydro-2-oxo-3-[(1H-pyrrol-2-yl)methylene]-1H-indol-4-yl]-phenyl]-3-cyanobenzamide (U), (Z)-N-[3-[2,3-Dihydro-2-oxo-3-[(1H-pyrrol-2-yl)methylene]-1H-indol-4-yl]-phenyl]-3-nitrobenzamide (V), (Z)-N-[3-[2,3-Dihydro-2-oxo-3-[(1H-pyrrol-2-yl)methylene]-1H-indol-4-yl]-phenyl]-4-fluorobenzamide (W), (Z)-N-[3-[2,3-Dihydro-2-oxo-3-[(1H-pyrrol-2-yl)methylene]-1H-indol-4-yl]-phenyl]-4-nitrobenzamide (X), (Z)-N-[3-[2,3-Dihydro-2-oxo-3-[(1H-pyrrol-2-yl)methylene]-1H-indol-4-yl]-phenyl]-4-methoxybenzamide (Y), (Z)-4-Amino-N-[3-2,3-dihydro-2-oxo-3-[(1H-pyrrol-2-yl)methylene]-1H-indol-4-yl]phenyl]cyclohexanecarboxamide (Z), (Z)-N-[3-[2,3-Dihydro-2-oxo-3-[(1H-pyrrol-2-yl)methylene]-1H-indol-4-yl]-phenyl]-4-(fluorosulfonyl)benzamide (AA), (Z)-N-[2-[[3-[2,3-Dihydro-2-oxo-3-[(1H-pyrrol-2-yl)methylene]-1H-indol-4-yl]phenyl]amino]-2-oxoethyl]-4-(fluorosulfonyl)benzamide (CC), (Z)-1,3-Dihydro-3-[(1H-pyrrol-2-yl)methylene]-4-(2-thiophenyl)-2H-indol-2-one (B), (Z)-1,3-Dihydro-4-(2,4-dimethoxy-6-pyrimidinyl)-3-[(3-methoxy-1H-pyrrol-2-yl)methylene]-2H-indol-2-one (FF), (Z)-1,3-Dihydro-4-(5-indolyl)-3-[(3-methoxy-1H-pyrrol-2-yl)methylene]-2H-indol-2-one (MM), (Z)-1,3-Dihydro-4-(5-indolyl)-3-[(3-methoxy-1H-pyrrol-2-yl)methylene]-5-nitro-2H-indol-2-one, (Z)-5-Amino-1,3-dihydro-4-(5-indolyl)-3-[(3-methoxy-1H-pyrrol-2-yl)methylene]-2H-indol-2-one, (Z)-N-[2,3-Dihydro-4-(5-indolyl)-3-[(3-methoxy-1H-pyrrol-2-yl)methylene]-2-oxo-1H-indol-5-yl]-2-thiopheneacetamide (QQ), (Z)-1,3-Dihydro-4-(4-indolyl)-3-[(3-methoxy-1H-pyrrol-2-yl)methylene]-2H-indol-2-one (TT), (Z)-1,3-Dihydro-4-(6-indolyl)-3-[(3-methoxy-1H-pyrrol-2-yl)methylene]-2H-indol-2-one (UU), (Z)-1,3-Dihydro-4-(6-indolyl)-3-[(3-methoxy-1H-pyrrol-2-yl)methylene]-5-nitro-2H-indol-2-one, (Z)-5-Amino-1,3-dihydro-4-(6-indolyl)-3-[(3-methoxy-1H-pyrrol-2-yl)methylene]-2H-indol-2-one, (Z)-N-[2,3-Dihydro-4-(6-indolyl)-3-[(3-methoxy-1H-pyrrol-2-yl)methylene]-2-oxo-1H-indol-5-yl]-2-thiopheneacetamide (VV), (Z)-N-[3-[2,3-Dihydro-2-oxo-3-[(1H-pyrrol-2-yl)methylene]-1H-indol-4-yl]phenyl]methanesulfonamide (K), (Z)-N-[3-[2,3-Dihydro-2-oxo-3-[(1H-pyrrol-2-yl)methylene]-1H-indol-4-yl]phenyl]-2-thiophenesulfonamide (O), (Z)-N-[3-[2,3-Dihydro-2-oxo-3-[(1H-pyrrol-2-yl)
methylene]-1H-indol-4-yl]phenyl]-4-(phenylsulfonyl)-
2-thiophenesulfonamide (DD),
(Z)-1,3-Dihydro-4-(4-hydroxyphenyl)-3-[(3-methoxy-
1H-pyrrol-2-yl)methylene]-5-nitro-2H-indol-2-one
(JJ),
(Z)-1,3-Dihydro-3-[(3-methoxy-1H-pyrrol-2-yl)
methylene]-5-nitro-4-phenyl-2H-indol-2-one (KK),
(Z)-N-[2,3-Dihydro-3-[(3-methoxy-1H-pyrrol-2-yl)
methylene]-2-oxo-4-phenyl-1H-indol-5-yl]-2-
thiopheneacetamide (LL),
(Z)-5-Amino-1,3-dihydro-4-(4-hydroxyphenyl)-3-[(3-
methoxy-1H-pyrrol-2-yl)methylene]-2H-indol-2-one
(NN),
(Z)-N-[2,3-Dihydro-4-(4hydroxyphenyl)-3-[(3-methoxy-
1H-pyrrol-2-yl)methylene]-2-oxo-1H-indol-5-yl]-2-
thiopheneacetamide (OO),
(Z)-5-Amino-1,3-dihydro-3-[(3-methoxy-1H-pyrrol-2-
yl)methylene]-4-phenyl-2H-indol-2-one (PP),
(Z)-1,3-Dihydro-3-[(4-methyl-1H-imidazol-5-yl)
methylene]-5-nitro-4-phenyl-2H-indol-2-one (YY),
(Z)-1,3-Dihydro-5-fluoro-4-(4-hydroxyphenyl)-3-[(4-
methyl-1H-imidazol-5-yl)methylene]-2H-indol-2-one
trifluoroacetate salt (ZZ),
(Z)-1,3-Dihydro-5-fluoro-4-(4-methoxyphenyl)-3-[(4-
methyl-1H-imidazol-5-yl)methylene]-2H-indol-2-one
trifluoroacetate salt (BBB),
(Z)-1,3-Dihydro-4-(3,4-dimethoxyphenyl)-5-fluoro-3-
[(4-methyl-1H-imidazol-5-yl)methylene]-2H-indol-2-
one (CCC),
(Z)-1,3-Dihydro-4-(2,4-dimethoxyphenyl)-5-fluoro-3-
[(4-methyl-1H-imidazol-5-yl)methylene]-2H-indol-2-
one (DDD),
(Z)-4-(1,3-Benzodioxol-5-yl)-1,3-dihydro-5-fluoro3-[(4-
methyl-1H-imidazol-5-yl)methylene]-2H-indol-2-one
trifluoroacetate salt (EEE),
(Z)-4-(3-Aminophenyl)-1,3-dihydro-5-fluoro-3-[(4-
methyl-1H-imidazol-5-yl)methylene]-2H-indol-2-one
(FFF),
(Z)-4-(3-Amino-4-methyl-phenyl)-1,3-dihydro-5-fluoro-
3-[(4-methyl-1H-imidazol-5-yl)methylene]-2H-indol-
2-one (GGG),
(Z)-1,3-Dihydro-5-fluoro-4-(3-hydroxyphenyl)-3-[(4-
methyl-1H-imidazol-5-yl)methylene]-2H-indol-2-one
(HHH),
(Z)-1,3-Dihydro-5-fluoro-4-(4-hydroxyphenyl)-3-[(1H-
pyrrol-2-yl)methylene]-2H-indol-2-one (III),
(Z)-1,3-Dihydro-5-fluoro-4-(4-hydroxyphenyl)-3-[(3-
methoxy-1H-pyrrol-2-yl)methylene]-2H-indol-2-one
(JJJ),
2-[3-[5-Fluoro-3-[(3-methoxy-1H-pyrrol-2-yl)
methylene]-2-oxo-2,3-dihydro-1H-indol-4-yl]-
phenylamino]-acetamide (KKK), and
(Z)-1,3-Dihydro-5-fluoro4-(4-hydroxymethyl-3-
methoxy-phenyl)-3-[(3-methoxy-1H-pyrrol-2-yl)
methylene]-2H-indol-2-one (LLL).

The compounds disclosed herein and covered by the above formulae may exhibit tautomerism or structural isomerism. It is intended that the invention encompasses any tautomeric or structural isomeric form of these compounds, or mixtures of such forms, and is not limited to any one tautomeric or structural isomeric form utilized within the formulae drawn above.

Synthesis of Compounds of Formula I

The compounds of formula I may be prepared by processes known in the art. Suitable processes for synthesizing these compounds are provided in the examples. Generally, these compounds may be prepared according to the following synthesis scheme:

General Step 1

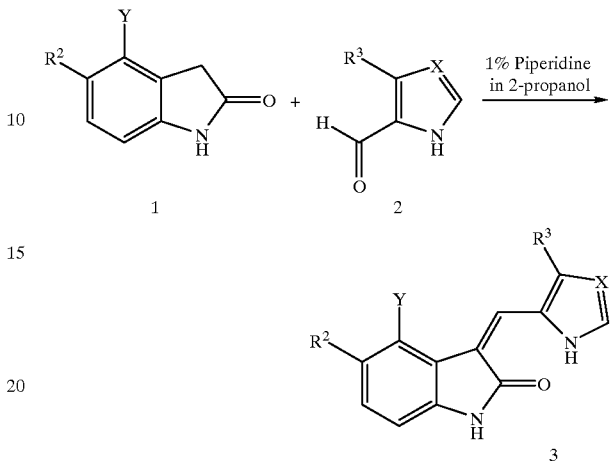

where Y = Br or I, X = N or C

General Step 2a

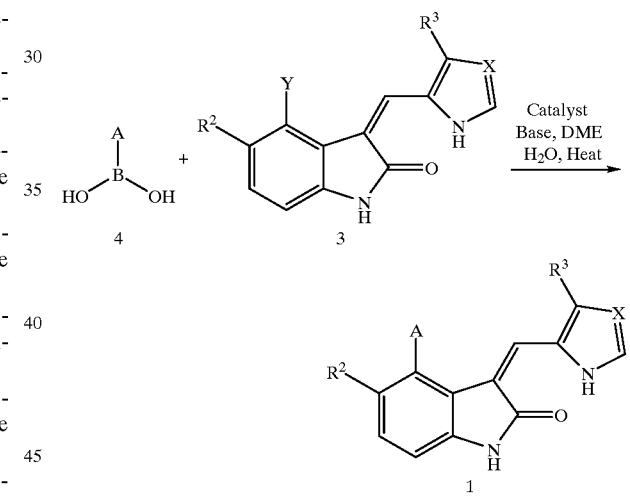

where Y = Br or I, X = N or C

Compounds 1 and 2 are either available from commercial sources or are synthesized by methods known in the art. Compounds 1 and 2 are reacted in piperidine and an appropriate solvent to yield compound 3. Compound 3 is then reacted with compound 4, which also is available from commercial sources or is synthesized by methods known in the art, to yield a compound of formula I. Compounds of formula II may be synthesized in an analogous manner.

Compositions/Formulations

In an alternative embodiment, the present invention is directed to pharmaceutical compositions comprising at least one compound according to the invention or a prodrug thereof, or a pharmaceutically acceptable salt of a compound according to the invention or a prodrug of such compound.

These pharmaceutical compositions can be administered orally, for example, in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I or formula II, prodrugs of such compounds, or the salts thereof, may be manufactured in a manner that is know in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid poll. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerin, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I or formula II.

Dosages

As mentioned above, the compounds of formula I or formula II, prodrugs thereof, and their salts, and compositions containing these compounds are useful in the treatment or control of inflammatory diseases and neuro-degenerative diseases, in particular, in the treatment or control of rheumatoid arthritis.

A therapeutically effective amount of a compound in accordance with this invention means an amount of compound that is effective to prevent, alleviate or ameliorate symptoms of disease of the subject being treated. Determination of a therapeutically effective amount is within the skill in the art.

The therapeutically effective amount or dosage of a compound according to this invention can vary within wide limits and will be adjusted to the individual requirements in each particular case. In general, in the case of oral or parental administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parental administration, it may be given as continuous infusion.

EXAMPLES

The compounds of the present invention may be synthesized according to known techniques, such as for example General Scheme I provided above. The following examples illustrate preferred methods for synthesizing the compounds and formulations of the present invention.

Example 1

General Synthesis Methods and Starting Materials
Method F: Preparation of Carboxylic Acids from the Methyl Esters

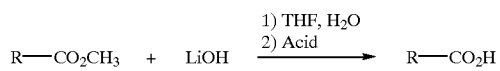

The appropriate methyl ester (0.14 mmol) was dissolved in a mixture of 2 mL tetrahydrofuran and 2 mL water. Lithium hydroxide (2.8 mmol, 20 equiv.) was added, and the reaction was stirred at room temperature for 14 hours. The tetrahydrofuran was then evaporated and 10 mL water was added. The aqueous layer was then extracted with ethyl acetate (2×10 mL). These ethyl acetate extracts were discarded. The aqueous layer was then acidified to pH=2 with 1 N hydrochloric acid, and extracted with ethyl acetate (4×20 mL). The combined organic extracts were washed with a saturated solution of sodium chloride and were then dried over magnesium sulfate. The ethyl acetate was then evaporated and the product was recrystallized from ethanol.
Method L:

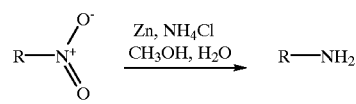

To a solution of nitro compound in 10% water in methanol was added Zn dust and $NH_4Cl$. The mixture was heated at reflux for 6 h then filtered through Celite® (Fisher Scientific). Filtrate was concentrated in vacuo. The product was purified via either flash column chromatography ($SiO_2$, 230–400 mesh with ethyl acetate/hexanes as solvent) or with reverse phase HPLC (using either acetonitrile/water or acetonitrile/water/trifluoroacetic acid as solvent).
Method M:

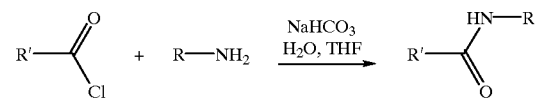

To a mixture of amino compound in THF and saturated aqueous $NaHCO_3$ was added a THF solution of the acid chloride dropwise. The mixture was stirred for from 3 h to 10 days at room temperature then diluted with ethyl acetate. The phases were separated and the organic solution was washed with water then dried ($MgSO_4$). The product was purified via either flash column chromatography ($SiO_2$, 230–400 mesh with ethyl acetate/hexanes as solvent) or with reverse phase HPLC (using either acetonitrile/water or acetonitrile/water/trifluoroacetic acid as solvent).
Method N: Preparation of 3-arylmethylene-substituted Oxindoles via Coupling with Aldehyde

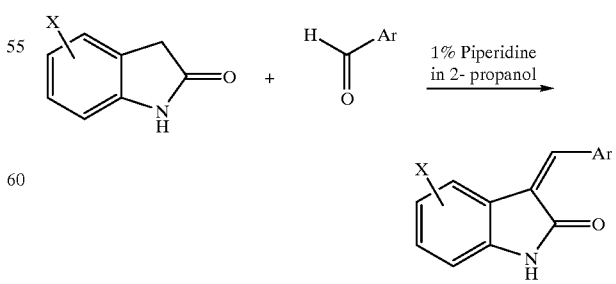

A solution or suspension of the appropriate oxindole (1 mmol), and excess aldehyde (1 to 2 mmol) in 2 mL of 1% piperidine in 2-propanol was heated at between 60 to 90° C. for 1 to 24 hours. Hot water (2 mL) was added. On cooling, the crystallized product was filtered off, washed with aqueous 2-propanol and dried.

Method S: Preparation of 4-aryloxindoles or 4-heteroaryloxindoles via Palladium(0)-mediated Coupling

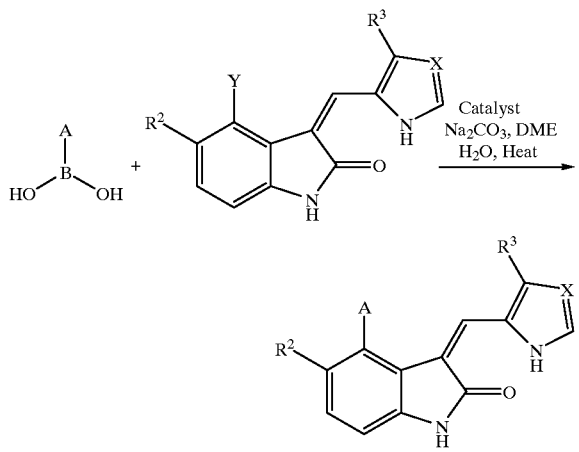

To a solution of the appropriate 4-iodooxindole (see T. Fukuyama et. al., *J. Am. Chem. Soc.* 118:7426–7427 (1996)) or 4-bromooxindole (see T. Kosuge et. al., *Chem. Pharm. Bull.* 33(4):1414–1418 (1985)) in dimethoxyethane was added an aryl or heteroaryl boronic acid, palladium catalyst, and an aqueous solution of 2M $Na_2CO_3$. The mixture was heated at reflux for up to 4 days. After cooling, the reaction mixture was filtered and concentrated. The product was purified via either flash column chromatography ($SiO_2$, 230–400 mesh with ethyl acetate/hexanes as solvent) or with reverse phase HPLC (using either acetonitrile/water or acetonitrile/water/trifluoroacetic acid as solvent).

STARTING MATERIALS

Starting Material 1
(Z)-1,3-Dihydro-4-iodo-3-[(1H-pyrrol-2-yl)methylene]-2H-indol-2-one

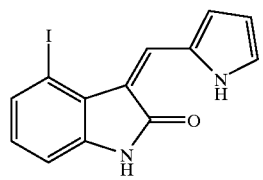

A mixture of 1,3-dihydro-4-iodo-2H-indol-2-one (404.1 mg, 1.56 mmol) (see Fukuyama et al., supra) and pyrrole-2-carboxaldehyde (163.2 mg, 1.72 mmol) (Aldrich) in 2-propanol (6.2 mL) was treated with 2 drops of piperidine. The reaction mixture was heated at reflux for 24 h and then allowed to cool to 23° C., at which time, the reaction mixture was filtered. The solid was washed several times with cold distilled water and then allowed to air dry to provide pure (Z)-1,3-dihydro-4-iodo-3-[(1H-pyrrol-2-yl)methylene]-2H-indol-2-one (341.8 mg, 65%) as a yellow solid which was used without further purification. (MP 256–258° C.).

Starting Materials 2
(Z)-4-Bromo-1,3-dihydro-3-[(1H-pyrrol-2-yl)methylene]-2H-indol-2-one

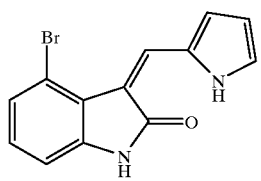

A mixture of 4-bromo-1,3-dihydro-2H-indol-2-one (0.2 g, 0.94 mmol) (see Kosuge et al., supra), and excess pyrrole-2-carboxaldehyde (0.11 g, 1.13 mmol) (Aldrich) in 1% piperidine in 2-propanol (2 mL) was heated at 85° C. for 2 h. Hot water (2 mL) was added. On cooling, the crystallized product was filtered off, washed with aqueous 2-propanol and dried. (Yield 0.26 g, 96%).

Starting Material 3
(Z)-1,3-Dihydro-4-iodo-3-[(3-methoxy-1H-pyrrol-2-yl)methylene]-2H-indol-2-one

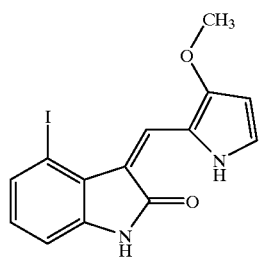

A mixture of 1,3-dihydro-4-iodo-2H-indol-2-one (0.51 g, 1.97 mmol) (see Fukuyama et al., supra), and excess 3-methoxy-2-pyrrolecarboxyaldehyde (0.30 g, 2.36 mmol) (prepared according to F. Bellamy et al., *J. Chem. Research (S)* (1979), 18–19; *J. Chem. Research (M)* (1979), 0101–0116) in 1% piperidine in 2-propanol (10 mL) was heated at 85° C. for 4 h. Hot water (10 mL) was added. On cooling, the crystallized product was filtered off, washed with aqueous 2-propanol and dried. (Yield 0.46 g, 64%).

Starting Material 4
1,3-Dihydro-4-iodo-5-nitro-2H-indol-2-one

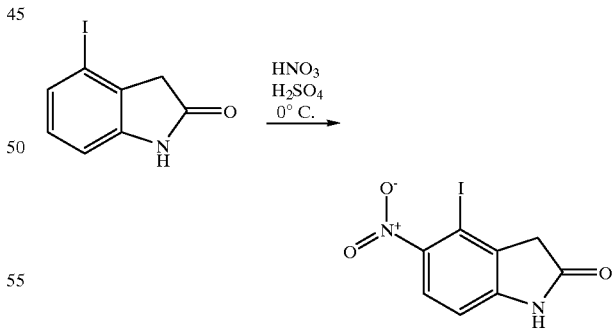

A mixture of concentrated sulfuric acid (0.73 mL) and concentrated nitric acid (0.14 mL) was added slowly to a solution of 1,3-dihydro-4-iodo-2H-indol-2-one (0.5 g, 1.93 mmol) (see Fukuyama et al., supra) in concentrated sulfuric acid (6 mL) at −5° C. with stirring. The mixture was stirred for an additional 15 min at −5° C. then poured into ice. After standing for 1 h, solid was collected by filtration and washed with water, and dried in a vacuum oven to give the above product. (Yield 0.46 g, 78%).

Starting Material 5
4-Bromo-1,3-dihydro-5-nitro-2H-indol-2-one

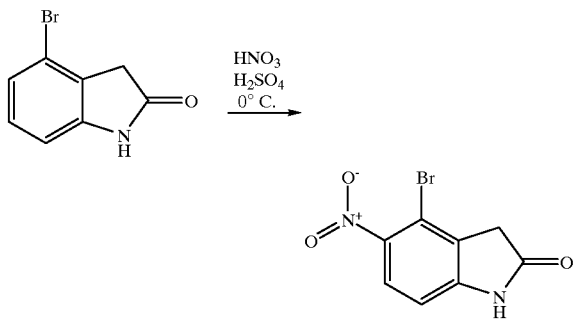

A mixture of concentrated sulfuric acid (3.6 mL) and concentrated nitric acid (0.7 mL) was added slowly to a solution of 4-bromo-1,3-dihydro-2H-indol-2-one (2 g, 9.48 mmol) (see Kosuge et al., supra) in concentrated sulfuric acid (20 mL) at −5° C. with stirring. The mixture was stirred for an additional 1 h at −5° C. then poured into ice. After standing for 1 h, precipitate formed was collected by filtration and washed with water, and dried in a vacuum oven to give the above product. (Yield 2.33 g, 96%).

Starting Material 6
(Z)-4-Bromo-1,3-dihydro-3-[(3-methoxy-1H-pyrrol-2-yl)methylene]-5-nitro-2H-indol-2-one

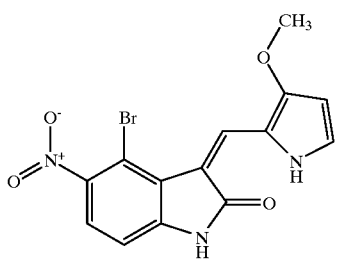

A mixture of 4-bromo-1,3-dihydro-5-nitro-2H-indol-2-one (0.113 g, 0.44 mmol) (Starting Material 5 above), and excess 3-methoxy-2-pyrrolecarboxyaldehyde (66.3 mg, 0.53 mmol) (see Bellamy et al., supra) in 1% piperidine in 2-propanol (2 mL) was heated at 85° C. for 3 h. Hot water (2 mL) was added. On cooling, the crystallized product was filtered off, washed with aqueous 2-propanol and dried. (Yield 0.136 g, 85%).

Starting Material 7
(Z)-4-Bromo-1,3-dihydro-3-[(3-methoxy-1H-pyrrol-2-yl)methylene]-2H-indol-2-one

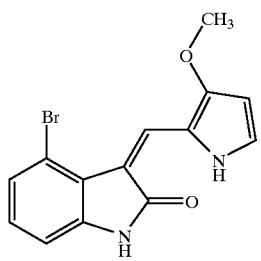

A mixture of 4-bromo-1,3-dihydro-2H-indol-2-one (100 mg, 0.47 mmol) (see Kosuge et al., supra) and excess 3-methoxy-2-pyrrolecarboxyaldehyde (70.8 mg, 0.57 mmol) (see Bellamy et al., supra) in 1% piperidine in 2-propanol (1 mL) was heated at 85° C. for 2 h. Hot water (1 mL) was added. On cooling, the crystallized product was filtered off, washed with aqueous 2-propanol and dried. (Yield 0.13 g, 83%).

Starting Material 8
2,4-Dimethoxy-6-(tributylstannyl)-pyrimidine

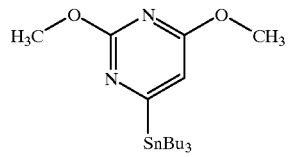

2,4-Dimethoxy-6-bromopyridine (1.73 g, 7.9 mmol) (prepared according to B. W. Langly et al., *J. Am. Chem. Soc.* 78:2136 (1955)) was dissolved in dry tetrahydrofuran (50 mL) under argon. The solution was cooled to −100° C. with an ethanol/liquid nitrogen bath. n-Butyllithium (4.74 mL, 11.8 mmol, 2.5 M solution in hexanes) (Aldrich) was added dropwise, very slowly (dripped down the inside of the flask in order to precool the solution), and the reaction was stirred at −100° C. for 5 min. Tributyltin chloride (Aldrich) was then added neat, and the reaction was slowly allowed to warm to room temperature where it was stirred for 1 h. A saturated solution of sodium bicarbonate (10 mL) was then added, and the tetrahydrofuran was evaporated in vacuo. The product was then extracted with chloroform (3×50 mL), and the combined organic extracts were dried over magnesium sulfate. The product was purified via flash column chromatography (5% MeOH/CHCl₃) to yield 2.17 g (64%) stannane as a clear oil.

Starting Material 9

(Z)-4-Bromo-1,3-dihydro-3-[(4-methyl-1H-imidazol-5-yl)methylene]-5-nitro-2H-indol-2-one

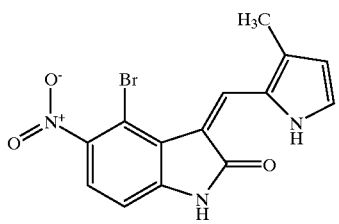

A mixture of 4-bromo-1,3-dihydro-5-nitro-2H-indol-2-one (1.49 g, 5.8 mmol) (Starting Material 5 above), and excess 4-methyl-5-imidazolecarboxyaldehyde (0.83 g, 7.54 mmol) (Aldrich) in 1% piperidine in 2-propanol (15 mL) was heated at 80° C. for 4 h. Hot water (15 mL) was added. On cooling, the crystallized product was filtered off, washed with aqueous 2-propanol and dried. (Yield 1.61 g, 80%).

Starting Material 10
1,3-Dihydro-5-fluoro-4-iodo-2H-indol-2-one

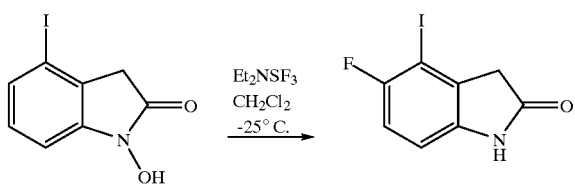

A suspension of 1,3-dihydro-1-hydroxy4-iodo-2H-indol-2-one, (2.43 g, 9 mmol) (prepared according to the procedure of A. S. Kende et al., *Synth. Commun.*, 20(14): 2133–2138 (1990)) in dry dichloromethane (500 mL) was cooled to −25° C. under an argon atmosphere with magnetic stirring. A solution of (diethylamino)sulfur trifluoride (DAST, 1.35 mL) (Aldrich) in dry dichloromethane (40 mL) was added dropwise at a rate such that the reaction temperature did not rise above −25° C. (about 15 min.) After stirring for an additional 30 min. at −25° C., the reaction was quenched by the addition of saturated aqueous sodium bicarbonate solution (180 mL) and allowed to warm to room temperature. The mixture was then filtered through Celite® (Fisher) and the layers separated. The aqueous layer was extracted with dichloromethane (2×300 mL). The dichloromethane layers were washed with saturated aqueous sodium chloride solution (200 mL), combined, dried (magnesium sulfate) and concentrated. Residue was purified by flash chromatography on silica gel using ethyl acetate—dichloromethane (1:7, V/V) as solvent to give 13-dihydro-5-fluoro-4-iodo-2H-indol-2-one (Yield 1.08 g, 43%).

Starting Material 11
(Z)-1,3-Dihydro-5-fluoro-4-iodo-3-[(4-methyl-1H-imidazol-5-yl)-methylene]-2H-indol-2-one

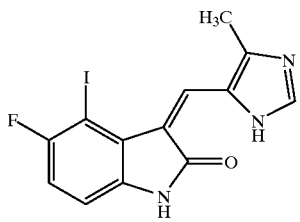

A mixture of 1,3-dihydro-5-fluoro-4-iodo-2H-indol-2-one (0.48 g, 1.7 mmol) (Starting Material 10 above), and excess 4-methyl-5-imidazolecarboxaldehyde (0.40 g, 3.6 mmol) (Aldrich) in 1% piperidine in 2-propanol (10 mL) was heated at 90° C. for 4 h. Hot water (10 mL) was added. On cooling, the crystallized product was filtered off, washed with aqueous 2-propanol and dried. Residue was purified by reverse phase chromatography using trifluoroacetic acid—acetonitrile—water as solvent to give (Z)-1,3-dihydro-5-fluoro-4-iodo-3-[(4-methyl-1H-imidazol-5-yl)-methylene]-2H-indol-2-one as trifluoroacetate salt. (Yield 0.64 g, 100%)

Starting Material 12
(Z)-1,3-Dihydro-5-fluoro-4-iodo-3-[(1H-pyrrol-2-yl)methylene]-2H-indol-2-one

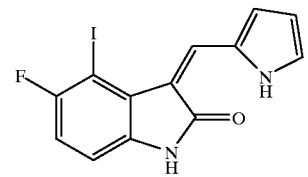

A mixture of 1,3-dihydro-5-fluoro-4-iodo-2H-indol-2-one (1.40 g, 5.05 mmol) (see Starting Material 10), and excess 2-pyrrolecarboxyaldehyde (0.60 g, 6.3 mmol) (Aldrich) in 1% piperidine in 2-propanol (20 mL) was heated at 85° C. for 2.25 h. Hot water (20 mL) was added. On cooling, the crystallized product was filtered off, washed with aqueous 2-propanol and dried. (Yield 1.50 g, 84%).

Starting Material 13
(Z)-1,3-Dihydro-5-fluoro-4-iodo-3-[(3-methoxy-1H-pyrrol-2-yl)methylene]-2H-indol-2-one

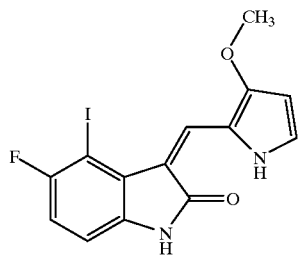

A mixture of 1,3-dihydro-5-fluoro-4-iodo-2H-indol-2-one (0.96 g, 3.47 mmol) (see Starting Material 10), and excess 3-methoxy-2-pyrrolecarboxyaldehyde (0.52 g, 4.16 mmol) (see Bellamy et al., *J. Chem. Research* (S), 18–19 (1979); *J. Chem. Research* (M), 0101–0116 (1979)), in 1% piperidine in 2-propanol (15 mL) was heated at 85° C. for 3 h. Hot water (15 mL) was added. On cooling, the crystallized product was filtered off, washed with aqueous 2-propanol and dried. (Yield 1.24 g, 93%).

Example 2
(Z)-1,3-Dihydro-4-phenyl-3-[(1H-pyrrol-2-yl)methylene]-2H-indol-2-one (A)

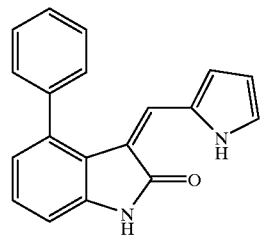

A solution of (Z)-1,3-dihydro-4-iodo-3-[(1H-pyrrol-2-yl)methylene]-2H-indol-2-one (30.4 mg, 0.090 mmol) (Starting Material 1), Et$_3$N (38 μL, 0.271 mmol), tri-o-tolylphosphine (1.7 mg, 0.006 mmol) (Aldrich), Pd(OAc)$_2$ (0.6 mg, 0.003 mmol)(Aldrich), and phenylboronic acid (16.5 mg, 0.136 mmol) (Aldrich) in 362 μL of dry N,N-dimethylformamide (Fisher Scientific) was heated at 100° C. for 24 h. The reaction mixture was allowed to cool to room temperature, concentrated in vacuo to remove N,N-dimethylformamide, and then directly purified by flash chromatography (Merck Silica gel 60, 70–230 mesh, 10% ethyl acetate-hexanes then 25% ethyl acetate-hexanes elution) to provide pure (Z)-1,3-dihydro-4-phenyl-3-[(1H-pyrrol-2-yl)methylene]-2H-indol-2-one (Yield 21.9 mg, 85%) as an orange solid (mp 184–185° C.).

Example 3
(Z)-1,3-Dihydro-3-[(1H-pyrrol-2-yl)methylene]-4-(2-thiophenyl)-2H-indol-2-one (B)

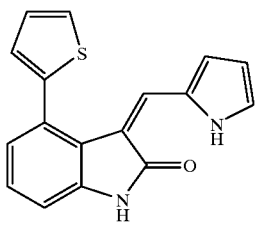

A solution of (Z)-1,3-dihydro-4-iodo-3-[(1H-pyrrol-2-yl) methylene]-2H-indol-2-one (36.9 mg, 0.110 mmol) (Starting Material 1), Et$_3$N (46 μL, 0.329 mmol), tri-o-tolylphosphine (2.1 mg, 0.007 mmol) (Aldrich), Pd(OAc)$_2$ (0.7 mg, 0.003 mmol) (Aldrich), and 2-thiopheneboronic acid (21.1 mg, 0.165 mmol) (Aldrich) in 439 μL of dry N,N-dimethylformamide was heated at 100° C. for 24 h. The reaction mixture was allowed to cool to room temperature, concentrated in vacuo to remove N,N-dimethylformamide, and then directly purified by flash chromatography (Merck Silica gel 60, 70–230 mesh, 10% ethyl acetate-hexanes then 25% ethyl acetate-hexanes elution) to provide pure (Z)-1,3-dihydro-3-[(1H-pyrrol-2-yl)methylene]-4-(2-thiophenyl)-2H-indol-2-one (Yield 26.8 mg, 83%) as an orange solid (mp 213–214° C.).

Example 4
(Z)-4-(3-Aminophenyl)-1,3-dihydro-3-[(1H-pyrrol-2-yl) methylene]-2H-indol-2-one (C)

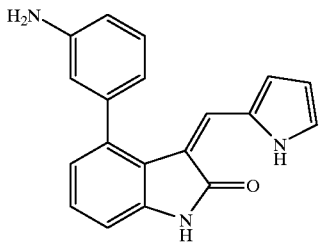

A solution of (Z)-1,3-dihydro-4-iodo-3-[(1H-pyrrol-2-yl) methylene]-2H-indol-2-one (500 mg, 1.49 mmol) (Starting Material 1), 2M aqueous Na$_2$CO$_3$ solution (1.49 mL, 2.98 mmol), (Ph$_3$P)$_4$Pd (86 mg, 0.074 mmol) (Aldrich), and 3-aminophenylboronic acid monohydrate (253 mg, 1.63 mmol) (Lancaster) in 10 mL of a 3:1 mixture of 1,2-dimethoxyethane:distilled water was heated at 100° C. under a nitrogen atmosphere for 96 h. The reaction mixture was allowed to cool to room temperature and then directly purified by flash chromatography (Merck Silica gel 60, 230–400 mesh, 35% ethyl acetate-hexanes elution) to yield pure (Z)-4-(3-aminophenyl)-1,3-dihydro-3-[(1H-pyrrol-2-yl)methylene]-2H-indol-2-one (410 mg, 91%) as a yellow solid (mp 92–94° C.) (solid to gel).

Example 5
(Z)-4-(3-Aminophenyl)-1,3-dihydro-3-[(1H-pyrrol-2-yl) methylene]-2H-indol-2-one hydrochloride salt (D)

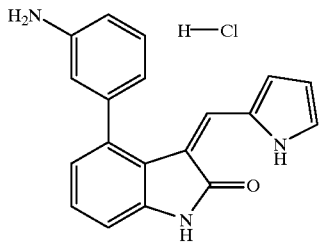

A solution of (Z)-4-(3-aminophenyl)-1,3-dihydro-3-[(1H-pyrrol-2-yl)methylene]-2H-indol-2-one (19.4 mg, 0.064 mmol) (Compound C from Example 4 above) in 7 mL of ethyl acetate was treated with anhydrous hydrogen chloride gas. A solid immediately precipitated. The anhydrous hydrogen chloride gas was bubbled into the reaction mixture for 4 min. The resulting solid was filtered and was allowed to air dry to provide pure hydrochloride salt (18.3 mg, 84%) as a yellow solid (mp 177–180° C.).

Example 6

(Z)-1,3-Dihydro-4-(4-methoxyphenyl)-3-[(1H-pyrrol-2-yl) methylene]-2H-indol-2-one (E)

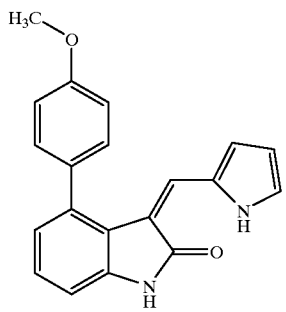

A solution of (Z)-1,3-dihydro-4-iodo-3-[(1H-pyrrol-2-yl) methylene]-2H-indol-2-one (100 mg, 0.298 mmol) (Starting Material 1), 2M aqueous Na$_2$CO$_3$ solution (342 μL, 0.684 mmol), (Ph$_3$P)$_4$Pd (17 mg, 0.015 mmol) (Aldrich), and 4-methoxyphenylboronic acid (52 mg, 0.342 mmol) (Aldrich) in 3 mL of a 2:1 mixture of 1,2-dimethoxyethane:distilled water was heated at 100° C. under a nitrogen atmosphere for 20 h. The reaction mixture was diluted with ethyl acetate, and the organic layer was washed with distilled water. The organic layer was concentrated in vacuo to provide a crude yellow-brown solid. Flash chromatography (Merck Silica gel 60, 230–400 mesh, 25% ethyl acetate-hexanes elution) yielded pure (Z)-1,3-dihydro-4-(4-methoxyphenyl)-3-[(1H-pyrrol-2-yl)methylene]-2H-indol-2-one (89.3 mg, 82%) as a yellow solid (mp 222–223° C.).

Example 7

(Z)-1,3-Dihydro-4-(3-nitrophenyl)-3-[(1H-pyrrol-2-yl) methylene]-2H-indol-2-one (F)

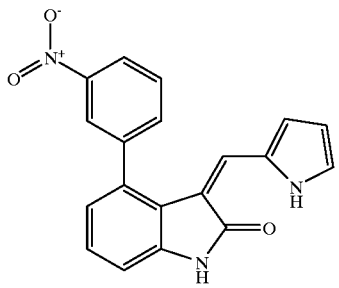

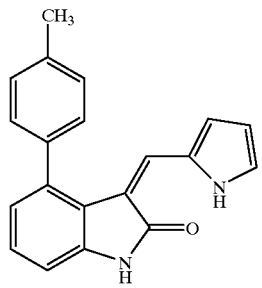

A solution of (Z)-1,3-dihydro-4-iodo-3-[(1H-pyrrol-2-yl) methylene]-2H-indol-2-one (35 mg, 0.104 mmol) (Starting Material 1), Et₃N (58 μL, 0.415 mmol), tri-o-tolylphosphine (6 mg, 0.020 mmol) (Aldrich), Pd(OAc)$_2$ (2 mg, 0.009 mmol) (Aldrich), and 3-nitrophenylboronic acid (26 mg, 0.156 mmol) (Aldrich) in 3 mL of dry N,N-dimethylformamide was heated at 100° C. for 16 h. The reaction mixture was allowed to cool to room temperature, concentrated in vacuo to remove N,N-dimethylformamide, and then directly purified by flash chromatography (Merck Silica gel 60, 70–230 mesh, 10% ethyl acetate-hexanes then 25% ethyl acetate-hexanes elution) to provide pure (Z)-1,3-dihydro-4-(3-nitrophenyl)-3-[(1H-pyrrol-2-yl)methylene]-2H-indol-2-one (24.1 mg, 70%) as an orange solid (mp 197–199° C.).

Example 8

(Z)-1,3-Dihydro-3-(1H-pyrrol-2-yl)methylene]-4-(3-trifluoromethylphenyl)-2H-indol-2-one (G)

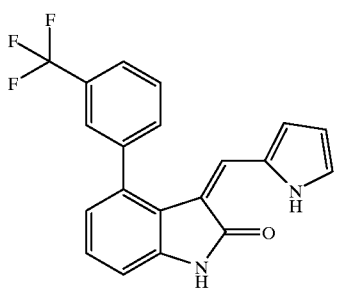

A suspension of (Z)-1,3-dihydro-4-iodo-3-[(1H-pyrrol-2-yl)methylene]-2H-indol-2-one (30 mg, 0.089 mmol) (Starting Material 1), K$_2$CO$_3$ (25 mg, 0.180 mmol), (Ph$_3$P)$_4$Pd (5 mg, 0.004 mmol) (Aldrich), and 3-(trifluoromethyl) phenylboronic acid (20 mg, 0.110 mmol) (Aldrich) in 2.5 mL of a 1.5:1 mixture of 1,2-dimethoxyethane:distilled water was heated at reflux under a nitrogen atmosphere for 14 h. The reaction mixture was allowed to cool to room temperature and then directly purified by flash chromatography (Merck Silica gel 60, 230–400 mesh, 25% ethyl acetate-hexanes then 40% ethyl acetate-hexanes elution) to yield pure (Z)-1,3-dihydro-3-[(1H-pyrrol-2-yl)methylene]-4-(3-trifluoromethylphenyl)-2H-indol-2-one (yield 18 mg, 56%) as a yellow solid (mp 197–198° C.).

Example 9

(Z)-1,3-Dihydro-4-(4-methylphenyl)-3-[(1H-pyrrol-2-yl) methylene]-2H-indol-2-one (H)

A solution of (Z)-1,3-dihydro-4-iodo-3-[(1H-pyrrol-2-yl) methylene]-2H-indol-2-one (30 mg, 0.089 mmol) (Starting Material 1) 2M aqueous Na$_2$CO$_3$ solution (89 μL, 0.178 mmol), (Ph$_3$P)$_4$Pd (5 mg, 0.004 mmol) (Aldrich), and 4-methylphenylboronic acid (15 mg, 0.110 mmol) (Aldrich) in 3 mL of a 2:1 mixture of 1,2-dimethoxyethane:distilled water was heated at 100° C. under a nitrogen atmosphere for 18 h. The reaction mixture was allowed to cool to room temperature and then directly purified by flash chromatography (Merck Silica gel 60, 230–400 mesh, 25% ethyl acetate-hexanes elution) to provide a crude yellow solid containing product. The solid was dissolved in chloroform and precipitation by the addition of hexanes provided pure (Z)-1,3-dihydro-4-(4-methylphenyl)-3-[(1H-pyrrol-2-yl) methylene]-2H-indol-2-one (yield 19 mg, 71%) as a yellow solid (mp 217–218° C.).

Example 10

(Z)-1,3-Dihydro-4-(2-methylphenyl)-3-[(1H-pyrrol-2-yl) methylene]-2H-indol-2-one (I)

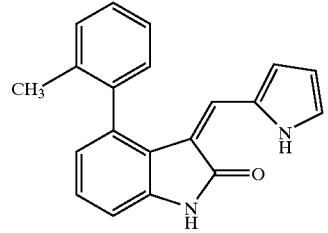

A solution of (Z)-1,3-dihydro-4-iodo-3-[(1H-pyrrol-2-yl) methylene]-2H-indol-2-one (30 mg, 0.089 mmol) (Starting Material 1), 2M aqueous Na$_2$CO$_3$ solution (89 μL, 0.178 mmol), (Ph$_3$P)$_4$Pd (3 mg, 0.003 mmol) (Aldrich), and 2-methylphenylboronic acid (15 mg, 0.110 mmol) (Aldrich) in 3 mL of a 3:1 mixture of 1,2-dimethoxyethane:distilled water was heated at 100° C. under a nitrogen atmosphere for 18 h. The reaction mixture was allowed to cool to room temperature and then directly purified by flash chromatography (Merck Silica gel 60, 230–400 mesh, 25% ethyl acetate-hexanes elution) to provide a crude yellow oil containing product. Recrystallization from chloroform-pentane yielded pure (Z)-1,3-dihydro-4-(2-methylphenyl)-3-[(1H-pyrrol-2-yl)methylene]-2H-indol-2-one (yield 20 mg, 75%) as yellow needle-like crystals (mp 195–197° C.).

Example 11

(Z)-4-(2,4-Dichlorophenyl)-1,3-dihydro-3-[(1H-pyrrol-2-yl)methylene]-2H-indol-2-one (J)

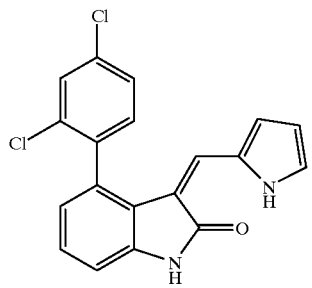

A solution of (Z)-1,3-dihydro-4-iodo-3-[(1H-pyrrol-2-yl)methylene]-2H-indol-2-one (70 mg, 0.208 mmol) (Starting Material 1), 2M aqueous Na$_2$CO$_3$ solution (210 μL, 0.420 mmol), (Ph$_3$P)$_4$Pd (10 mg, 0.009 mmol) (Aldrich), and 2,4-dichlorophenylboronic acid (44 mg, 0.231 mmol) (Lancaster) in 6 mL of a 5:1 mixture of benzene:1,2-dimethoxyethane was heated at reflux under a nitrogen atmosphere for 18 h. The reaction mixture was allowed to cool to room temperature and then directly purified by flash chromatography (Merck Silica gel 60, 230–400 mesh, 60% ethyl acetate-hexanes elution) to yield pure (Z)-$_4$-(2,4-dichlorophenyl)-1,3-dihydro-3-[(1H-pyrrol-2-yl)methylene]-2H-indol-2-one (yield 52 mg, 69%) as a yellow-brown solid (mp 185–187° C.).

Example 12

(Z)-N-[3-[2,3-Dihydro-2-oxo-3-(1H-pyrrol-2-yl-methylene)-1H-indol-4-yl]phenyl]methanesulfonamide (K)

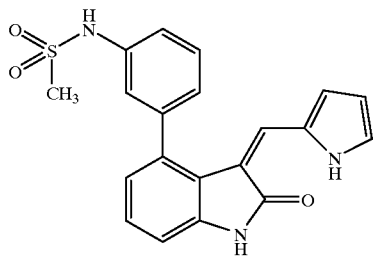

A solution of (Z)-4-(3-aminophenyl)-1,3-dihydro-3-[(1H-pyrrol-2-yl)methylene]-2H-indol-2-one (25 mg, 0.083 mmol) (from Example 4 supra) in 1 mL of dry pyridine (Fisher Scientific) was treated with methanesuffonyl chloride (11.4 mg, 0.100 mmol) (Aldrich). The reaction mixture was heated at 80° C. under a nitrogen atmosphere for 10 min. The reaction mixture was allowed to cool to room temperature and then directly purified by flash chromatography (Merck Silica gel 60, 230–400 mesh, 20% ethyl acetate-hexanes elution) to yield pure (Z)-N-[3-[2,3-dihydro-2-oxo-3-(1H-pyrrol-2-yl-methylene)-1H-indol-4-yl]phenyl]methanesuffonamide (21 mg, 67%) as a yellow solid (mp 224–225° C.).

Example 13

(Z)-4-(4-Chlorophenyl)-1,3-dihydro-3-[(1H-pyrrol-2-yl)methylene]-2H-indol-2-one (L)

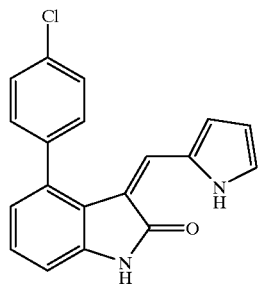

A solution of (Z)-1,3-dihydro-4-iodo-3-[(1H-pyrrol-2-yl)methylene]-2H-indol-2-one (40 mg, 0.119 mmol) (Starting Material 1), 2M aqueous Na$_2$CO$_3$ solution (119 μL, 0.238 mmol), (Ph$_3$P)$_4$Pd (5 mg, 0.004 mmol) (Aldrich), and 4-chlorophenylboronic acid (21 mg, 0.134 mmol) (Aldrich) in 4 mL of a 3:1 mixture of 1,2-dimethoxyethane:distilled water was heated at reflux under a nitrogen atmosphere for 20 h. The reaction mixture was allowed to cool to room temperature and then directly purified by column chromatography. Flash chromatography (Merck Silica gel 60, 230–400 mesh, 20% ethyl acetate-hexanes elution) provided a crude yellow solid. Recrystallization from chloroform-pentane yielded pure (Z)-4-(4-chlorophenyl)-1,3-dihydro-3-[(1H-pyrrol-2-yl)methylene]-2H-indol-2-one (34 mg, 89%) as a yellow solid (mp 188–190° C.).

Example 14

(Z)-1,3-Dihydro-4-(2-methoxyphenyl)-3-[(1H-pyrrol-2-yl)methylene]-2H-indol-2-one (M)

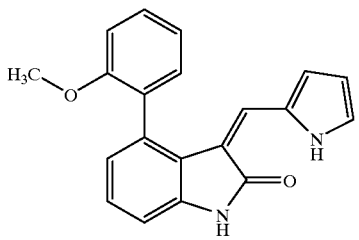

A solution of (Z)-1,3-dihydro-4-iodo-3-[(1H-pyrrol-2-yl)methylene]-2H-indol-2-one (50 mg, 0.149 mmol) (Starting Material 1), 2M aqueous Na$_2$CO$_3$ solution (149 μL, 0.298 mmol), (Ph$_3$P)$_4$Pd (5 mg, 0.004 mmol) (Aldrich), and 2-methoxyphenylboronic acid (25 mg, 0.164 mmol) (Aldrich) in 4 mL of a 2:1 mixture of 1,2-dimethoxyethane:distilled water was heated at 100° C. under a nitrogen atmosphere for 18 h. The reaction mixture was allowed to cool to room temperature and then directly purified by flash chromatography (Merck Silica gel 60, 230–400 mesh, 20% ethyl acetate-hexanes elution) to provide a crude yellow solid. Recrystallization from chloroform-pentane yielded pure (Z)-1,3-dihydro-4-(2-methoxyphenyl)-3-[(1H-pyrrol-2-yl)methylene]-2H-indol-2-one (Yield 37 mg, 79%) as yellow crystals (mp 223–225° C.).

Example 15

(Z)-1,3-Dihydro-4-(1-naphthalenyl)-3-[(1H-pyrrol-2-yl)methylene]-2H-indol-2-one (N)

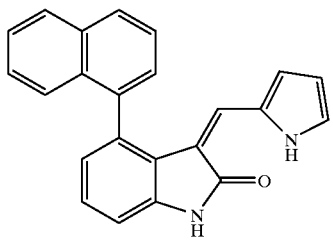

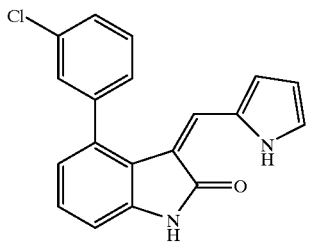

A solution of (Z)-1,3-dihydro-4-iodo-3-[(1H-pyrrol-2-yl) methylene]-2H-indol-2-one (40 mg, 0.119 mmol) (Starting Material 1), 2M aqueous $Na_2CO_3$ solution (119 µL, 0.238 mmol), $(Ph_3P)_4Pd$ (3 mg, 0.003 mmol) (Aldrich), and 1-naphthaleneboronic acid (22.5 mg, 0.131 mmol) (Lancaster) in 3 mL of a 3:1 mixture of 1,2-dimethoxyethane:distilled water was heated at 100° C. under a nitrogen atmosphere for 20 h. The reaction mixture was allowed to cool to room temperature and then directly purified by flash chromatography (Merck Silica gel 60, 230–400 mesh, 20% ethyl acetate-hexanes then 30% ethyl acetate-hexanes elution) to yield a crude solid. Recrystallization from chloroform-pentane provided pure (Z)-1,3-dihydro-4-(1-naphthalenyl)-3-[(1H-pyrrol-2-yl)methylene]-2H-indol-2-one (yield 31 mg, 78%) as yellow crystals (mp 210–212° C.).

Example 16

(Z)-N-[3-[2,3-Dihydro-2-oxo-3-[(1H-pyrrol-2-yl) methylene]-1H-indol-4-yl]phenyl]-2-thiophenesulfonamide (O)

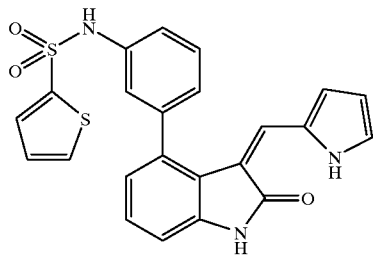

A suspension of (Z)-4-(3-aminophenyl)-1,3-dihydro-3-[(1H-pyrrol-2-yl)methylene]-2H-indol-2-one (27 mg, 0.090 mmol) (from Example 4 supra) in 1.5 mL of pyridine (Fisher Scientific) was treated dropwise with 2-thiophenesulfonyl chloride (19 mg, 0.104) (Aldrich). The reaction mixture was stirred at room temperature for 30 min and then directly purified by flash chromatography (Merck Silica gel 60, 230–400 mesh, 20% ethyl acetate-hexanes then 40% ethyl acetate-hexanes elution) to provide a crude yellow solid. Recrystallization from chloroform-pentane provided pure (Z)-N-[3-[2,3-dihydro-2-oxo-3-(1H-pyrrol-2-yl) methylene]-1H-indol-4-yl]phenyl]-2-thiophenesulfonamide (17 mg, 42%) as an orange solid (mp 218–220° C.).

Example 17

(Z)-4-(3-Chlorophenyl)-1,3-dihydro-3-[(1H-pyrrol-2-yl) methylene]-2H-indol-2-one (P)

A solution of (Z)-1,3-dihydro-4-iodo-3-[(1H-pyrrol-2-yl) methylene]-2H-indol-2-one (30 mg, 0.089 mmol) (Starting Material 1), 2M aqueous $Na_2CO_3$ solution (89 µL, 0.178 mmol), $(Ph_3P)_4Pd$ (5 mg, 0.004 mmol) (Aldrich), and 3-chlorophenylboronic acid (16 mg, 0.102 mmol) (Aldrich) in 3 mL of a 2:1 mixture of 1,2-dimethoxyethane:distilled water was heated at reflux under a nitrogen atmosphere for 16 h. The reaction mixture was allowed to cool to room temperature and then directly purified by flash chromatography (Merck Silica gel 60, 230–400 mesh, 25% ethyl acetate-hexanes elution) to provide pure (Z)-4-(3-chlorophenyl)-1,3-dihydro-3-[(1H-pyrrol-2-yl)methylene]-2H-indol-2-one (26 mg, 90%) as a yellow solid (mp 165–167° C.).

Example 18

(Z)-4-[2,3-Dihydro-2oxo-3-[(1H-pyrrol-2-yl)methylene]-1H-indol-4-yl]-benzoic acid (Q)

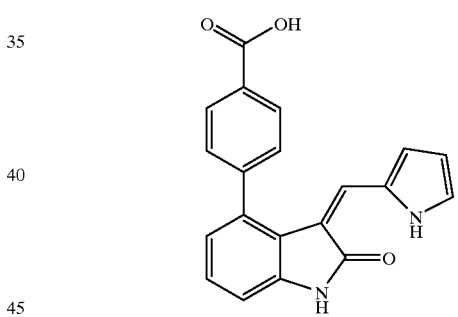

A solution of (Z)-1,3-dihydro-4-iodo-3-[(1H-pyrrol-2-yl) methylene]-2H-indol-2-one (30 mg, 0.089 mmol) (Starting Material 1), 2M aqueous $Na_2CO_3$ solution (151 µL, 0.303 mmol), $(Ph_3P)_2PdCl_2$ (3 mg, 0.004 mmol) (Aldrich), and 4-carboxyphenylboronic acid (18 mg, 0.108 mmol) (Lancaster) in 4.5 mL of a 2:1 mixture of 1,2-dimethoxyethane:distilled water was heated at reflux under a nitrogen atmosphere for 20 h. The reaction mixture was allowed to cool to room temperature and then directly purified by flash chromatography (Merck Silica gel 60, 230–400 mesh, 40% ethyl acetate-hexanes then 50% ethyl acetate-hexanes with 1% glacial acetic acid elution) to yield pure (Z)-4-[2,3-Dihydro-2-oxo-3-[(1H-pyrrol-2-yl) methylene]-1H-indol-4-yl]-benzoic acid (yield: 33 mg, 91%) as an orange solid (mp 315–317° C.).

Example 19

(Z)-1,3-Dihydro-4-(4-hydroxyphenyl)-3-[(1H-pyrrol-2-yl) methylene]-2H-indol-2-one (R)

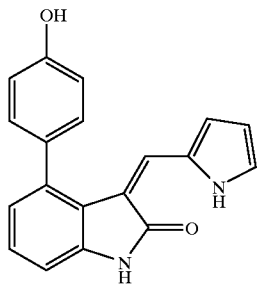

A solution of (Z)-1,3-dihydro-4-iodo-3-[(1H-pyrrol-2-yl)methylene]-2H-indol-2-one (45 mg, 0.134 mmol) (Starting Material 1), 2M aqueous Na$_2$CO$_3$ solution (134 μL, 0.268 mmol), (Ph$_3$P)$_4$Pd (5 mg, 0.004 mmol) (Aldrich), and 4-hydroxyphenylboronic acid (37 mg, 0.268 mmol) (prepared according to H. Gilman et al., *J. Am. Chem. Soc.* 79:3077–3081 (1957)) in 3 mL of a 3:1 mixture of 1,2-dimethoxyethane:distilled water was heated at reflux under a nitrogen atmosphere for 15 h. The reaction mixture was allowed to cool to room temperature and then directly purified by flash chromatography (Merck Silica gel 60, 230–400 mesh, 35% ethyl acetate-hexanes elution) to yield pure (Z)-1,3-dihydro-4-(4-hydroxyphenyl)-3-[(1H-pyrrol-2-yl)methylene]-2H-indol-2-one (yield: 32 mg, 79%) as a yellow solid (mp 271–273° C.).

Example 20

(Z)-N-[3-[2,3-Dihydro-2-oxo-3-[(1H-pyrrol-2-yl)methylene]-1H-indol-4-yl]-phenyl]-4-hydroxybenzamide (S)

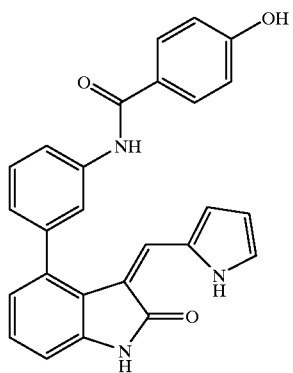

A mixture of (Z)-4-(3-aminophenyl)-1,3-dihydro-3-[(1H-pyrrol-2-yl)methylene]-2H-indol-2-one (59 mg, 0.196 mmol) (from Example 4 supra), 4-acetoxybenzoic acid (38 mg, 0.210 mmol) (Aldrich), and 1,3-dicyclohexylcarbodiimide (41 mg, 0.199) (Aldrich) in 4 mL of chloroform was heated at reflux for 22 h. The reaction mixture was diluted with hexane. The resulting yellow precipitate was collected by suction filtration to provide crude carbonic acid methyl ester 4-[3-[2-oxo-3-[(1H-pyrrol-2-yl)methylene]-2,3-dihydro-1H-indol-4-yl]-phenylcarbamoyl]-phenyl ester as a yellow solid (91 mg, 98%) which was used without further purification.

A solution of the crude carbonic acid methyl ester 4-[3-[2-oxo-3-[(1H-pyrrol-2-yl)methylene]-2,3-dihydro-1H-indol-4-yl]-phenylcarbamoyl]-phenyl ester (90 mg, 0.194 mmol) in 2 mL of 1,4-dioxane (Aldrich) was treated with 1.5 mL of distilled water and then powdered potassium hydroxide (25 mg, 0.445 mmol). The reaction mixture was heated at 90° C. for 1 h. The reaction mixture was then allowed to cool to room temperature and directly purified by flash chromatography (Merck Silica gel 60, 230–400 mesh, 45% ethyl acetate-hexanes elution) to provide a crude yellow solid containing the desired product and a 1,3-dicyclohexylcarbodiimide derivative. Most of the 1,3-dicyclohexylcarbodiimide derivative was removed by precipitation from an ethanolic solution through the slow addition of distilled water. The precipitated solid was collected by suction filtration. The filtrate was concentrated in vacuo and then directly purified by column chromatography. Two additional rounds of flash chromatography (Merck Silica gel 60, 230–400 mesh, 25% ethyl acetate-hexanes elution each) provided pure (Z)-N-[3-[2,3-dihydro-2-oxo-3-[(1H-pyrrol-2-yl)methylene]-1H-indol-4-yl]-phenyl]-4-hydroxybenzamide (yield: 49 mg, 60%) as a yellow solid (mp 236–238° C.).

Example 21

(Z)-N-[3-[2,3-Dihydro-2-oxo-3-[(1H-pyrrol-2-yl)methylene]-1H-indol-4-yl]-phenyl-3-bromobenzamide (T)

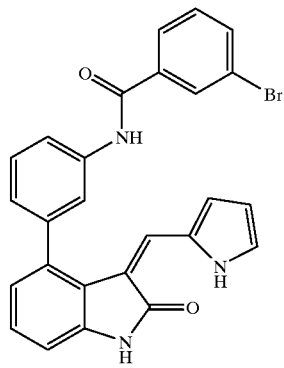

A solution of (Z)-4-(3-aminophenyl)-1,3-dihydro-3-[(1H-pyrrol-2-yl)methylene]-2H-indol-2-one hydrochloride (50 mg, 0.148 mmol) (from Example 5 supra) and Et$_3$N (41 μL, 0.296 mmol) in 3 mL of chloroform was cooled to −70° C. and then treated with 3-bromobenzoyl chloride (21 μL, 0.155 mmol) (Aldrich). The reaction mixture was stirred at −70° C. for 1 hr and then stirred at room temperature for 15 h. The reaction mixture was then concentrated in vacuo. The resulting yellow solid was suspended in water and collected by suction filtration to provide pure (Z)-N-[3-[2,3-dihydro-2-oxo-3-[(1H-pyrrol-2-yl)methylene]-1H-indol-4-yl]-phenyl]-3-bromobenzamide (yield: 70 mg, 98%) as a yellow solid (mp 251–253° C.).

Example 22

(Z)-N-[3-[2,3-Dihydro-2oxo-3-[(1H-pyrrol-2-yl)methylene]-1H-indol-4-yl]-phenyl]-3-cyanobenzamide (U)

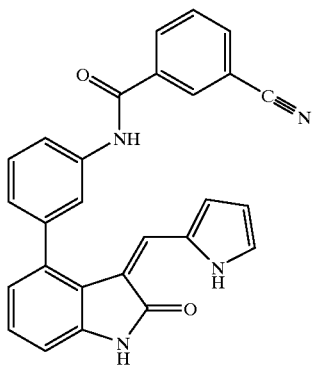

A solution of (Z)-4-(3-aminophenyl)-1,3-dihydro-3-[(1H-pyrrol-2-yl)methylene]-2H-indol-2-one hydrochloride (40 mg, 0.118 mmol) (from Example 5 supra) and Et$_3$N (33 μL, 0.237 mmol) in 3 mL of chloroform was treated with 3-cyanobenzoyl chloride (22 mg, 0.130 mmol) (Aldrich), and the resulting reaction mixture was stirred at room temperature for 15 h. The reaction mixture was concentrated in vacuo to remove chloroform. The yellow residue was suspended in distilled water, and the resulting solid was collected by suction filtration to provide pure (Z)-N-[3-[2,3-dihydro-2-oxo-3-[(1H-pyrrol-2-yl)methylene]-1H-indol-4-yl]-phenyl]-3-cyanobenzamide (yield: 41 mg, 81%) as a yellow solid (mp 250–251° C.).

Example 23
(Z)-N-[3-[2,3-Dihydro-2oxo-3-[(1H-pyrrol-2-yl)methylene]-1H-indol-4-yl]-phenyl]-3-nitrobenzamide (V)

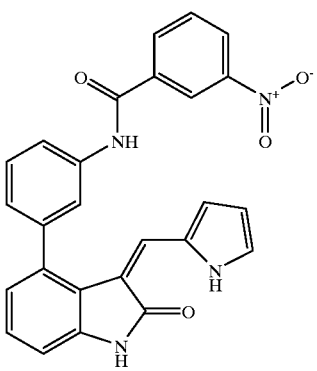

A solution of (Z)-4-(3-aminophenyl)-1,3-dihydro-3-[(1H-pyrrol-2-yl)methylene]-2H-indol-2-one hydrochloride (40 mg, 0.1 18 mmol) (from Example 5 supra) and Et$_3$N (33 μL, 0.237 mmol) in 3 mL of chloroform was cooled to −78° C. and then treated with 3-nitrobenzoyl chloride (24 mg, 0.129 mmol) (Aldrich). The reaction mixture was then stirred at room temperature under a nitrogen atmosphere for 7 h. The reaction mixture was then concentrated in vacuo. The resulting yellow solid was dissolved in ethanol, and re-precipitated by the addition of distilled water to yield pure (Z)-N-[3-[2,3-dihydro-2-oxo-3-[(1H-pyrrol-2-yl)methylene]-1H-indol-4-yl]-phenyl]-3-nitrobenzamide (yield: 50 mg, 94%) as a yellow solid (mp 265–266° C.).

Example 24
(Z)-N-[3-[2,3-Dihydro-2-oxo-3-[(1H-pyrrol-2-yl)methylene]-1H-indol-4-yl]-phenyl]-4-fluorobenzamide (W)

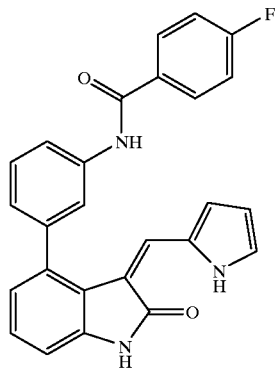

A solution of (Z)-4-(3-aminophenyl)-1,3-dihydro-3-[(1H-pyrrol-2-yl)methylene]-2H-indol-2-one hydrochloride (25 mg, 0.074 mmol) (from Example 5 supra) and Et$_3$N (21 μL, 0.148 mmol) in 3 mL of chloroform was treated with 4-fluorobenzoyl chloride (10.5 μL, 0.088 mmol) (Aldrich). The resulting reaction mixture was stirred at room temperature for 8 h and then directly purified by flash chromatography (Merck Silica gel 60, 230–400 mesh, 50% ethyl acetate-hexanes elution) to provide pure (Z)-N-[3-[2,3-dihydro-2-oxo-3-[(1H-pyrrol-2-yl)methylene]-1H-indol-4-yl]-phenyl]-4-fluorobenzamide (yield: 26 mg, 83%) as a yellow solid (mp 130–131° C.).

Example 25
(Z)-N-[3-[2,3-Dihydro-2-oxo-3-[(1H-pyrrol-2-yl)methylene]-1H-indol-4-yl]-phenyl]-4-nitrobenzamide (X)

A solution of (Z)-4-(3-aminophenyl)-1,3-dihydro-3-[(1H-pyrrol-2-yl)methylene]-2H-indol-2-one hydrochloride (25 mg, 0.074 mmol) (from Example 5 supra) and Et$_3$N (20 μL, 0.150 mmol) in 3 mL of chloroform was cooled to −70° C. and then treated with 4-nitrobenzoyl chloride (16 mg, 0.085 mmol) (Aldrich). The reaction mixture was stirred at −70° C. for 1 hr and then stirred at room temperature for 15 h. The reaction mixture was then concentrated in vacuo. Flash chromatography (Merck Silica gel 60, 230–400 mesh, 50% ethyl acetate-hexanes elution) provided pure (Z)-N-[3-[2,3-dihydro-2-oxo-3-[(1H-pyrrol-2-yl)methylene]-1H-indol-4-yl]-phenyl]-4-nitrobenzamide (yield: 24 mg, 72%) as a yellow-brown solid (mp 157–159° C.).

Example 26
(Z)-N-[3-[2,3-Dihydro-2-oxo-3-[(1H-pyrrol-2-yl)methylene]-1H-indol-4-yl]-phenyl]-4-methoxybenzamide (Y)

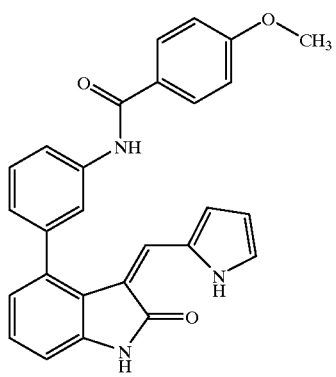

A solution of (Z)-4-(3-aminophenyl)-1,3-dihydro-3-[(1H-pyrrol-2-yl)methylene]-2H-indol-2-one hydrochloride (30 mg, 0.089 mmol) (from Example 5 supra) and Et$_3$N (24 μL, 0.172 mmol) in 3 mL of chloroform was cooled to −70° C. and then treated with 4-methoxybenzoyl chloride (17.4 mg, 0.102 mmol) (Fluka). The reaction mixture was stirred at −70° C. for 1 hr and then stirred at room temperature for 15 h. The reaction mixture was then concentrated in vacuo. Flash chromatography (Merck Silica gel 60, 230–400 mesh, 50% ethyl acetate-hexanes elution) provided pure (Z)-N-[3-[2,3-dihydro-2-oxo3-[(1H-pyrrol-2-yl) methylene]-1H-indol-4-yl]-phenyl]-4-methoxybenzamide (31 mg, 80%) as a brown solid (mp 209–211° C.).

Example 27
(Z)-4-Amino-N-[3-[2,3-dihydro-2-oxo-3-[(1H-pyrrol-2-yl)methylene]-1H-indol-4-yl]phenyl]cyclohexanecarboxamide (Z)

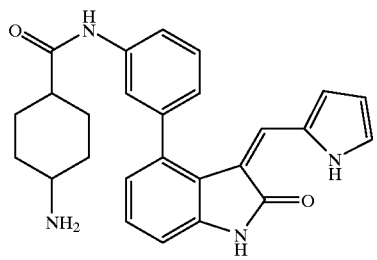

A suspension of (Z)-4-(3-aminophenyl)-1,3-dihydro-3-[(1H-pyrrol-2-yl)methylene)]-2H-indol-2-one hydrochloride (53 mg, 0.157 mmol) (from Example 5 supra) and 4-(tert-butoxycarbonylamino)cyclohexanecarboxylic acid (53 mg, 0.204 mmol) (prepared according to K. J. Cutrona et al., *Tetrahedron Lett.* 37(29):5045–5048 (1996)) in 4 mL of dry N,N-dimethylformamide was treated with O-benzotriazol-1-yl-N,N,N',N'-tetramethyluronium hexafluorophosphate (HBTU, 77 mg, 0.204 mmol) (Advance ChemTech) and N,N-diisopropylethylamine (88 μL, 0.628 mmol) (Aldrich). The reaction mixture was heated at 60° C. under a nitrogen atmosphere for 15 h. The reaction mixture was then diluted with 20 mL of a 1N aqueous hydrochloric acid solution and extracted with ethyl acetate (3×20 mL). The combined organic extracts were concentrated in vacuo. Flash chromatography (Merck Silica gel 60, 230–400 mesh, 45% ethyl acetate-hexanes elution) provided pure (Z)-[4-[3-[2,3-dihydro-2-oxo-3-[(1H-pyrrol-2-yl)methylene]-1H-indol-4-yl]-phenylcarbamoyl]-cyclohexyl]-carbamic acid tert-butyl ester (51.4 mg, 62%) as a yellow solid.

A solution of the (Z)-[4-[3-[2,3-dihydro-2-oxo-3-[(1H-pyrrol-2-yl)methylene]-1H-indol-4-yl]-phenylcarbamoyl]-cyclohexyl]-carbamic acid tert-butyl ester (51.4 mg, 0.098 mmol) in 3 mL of methylene chloride was then treated with 2 mL of trifluoroacetic acid. The reaction mixture was stirred at room temperature for 1 h, and the reaction mixture was diluted with 50 mL of ethyl acetate. The organic phase was carefully washed with a saturated aqueous sodium bicarbonate solution (3×20 mL), dried over sodium sulfate, filtered, and concentrated in vacuo to provide a yellow-brown solid. This crude solid was washed with 70% chloroform-hexanes, and the insoluble solid was collected by suction filtration to provide pure (Z)-4-amino-N-[3-[2,3-dihydro-2-oxo-3-[(1H-pyrrol-2-yl)methylene]-1H-indol-4-yl]phenyl]cyclohexanecarboxamide (yield: 17 mg, 40%) as a yellow solid (mp 210–212° C.).

Example 28

(Z)-N-[3-[2,3-Dihydro-2-oxo-3-[(1H-pyrrol-2-yl)methylene]-1H-indol-4-yl]-phenyl]-4-(fluorosulfonyl)benzamide (AA)

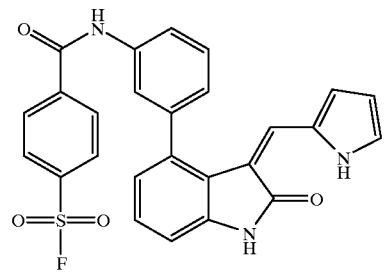

A solution of (Z)-4-(3-aminophenyl)-1,3-dihydro-3-[(1H-pyrrol-2-yl)methylene]-2H-indol-2-one (30 mg, 0.100 mmol) (from Example 4 supra) and Et$_3$N (14 μL, 0.100 mmol) in 5 mL of chloroform was cooled to −78° C. and then treated with 4-(fluorosulfonyl)benzoyl chloride (24 mg, 0.109 mmol) (Aldrich). The reaction mixture was stirred at −78° C. under a nitrogen atmosphere for 1 hr and then heated at reflux. The reaction mixture was allowed to cool to room temperature and then diluted with chloroform. The organic phase was then washed, in sequence, as follows: with a saturated aqueous sodium bicarbonate solution, with distilled water, with a 1N aqueous hydrochloric acid solution, and finally with a saturated aqueous sodium chloride solution. The organic phase was dried over sodium sulfate, filtered, and concentrated in vacuo. Flash chromatography (Merck Silica gel 60, 230–400 mesh, 30% ethyl acetate-hexanes elution) yielded pure (Z)-N-[3-[2,3-dihydro-2-oxo-3-[(1H-pyrrol-2-yl)methylene]-1H-indol-4-yl]-phenyl]-4-(fluorosulfonyl)benzamide (yield: 25.6 mg, 53%) as a yellow solid (mp: 148–151° C.).

Example 29

(Z)-3-[2,3-Dihydro-2-oxo-3-[(1H-pyrrol-2-yl)methylene]-1H-indol-4-yl]-benzoic acid (BB)

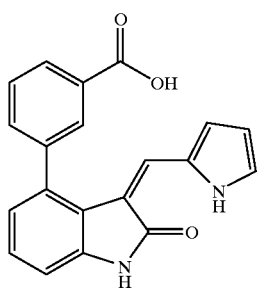

Step A: 3-Carboxyphenylboronic Acid

A solution of 3-formylphenylboronic acid (3.35 g, 22.34 mmol) (Lancaster) in a 1:1 mixture of distilled water-acetone (64 mL) was slowly treated with potassium permanganate (6.00 g, 37.98 mmol) in small portions. The dark reaction mixture was stirred at room temperature for 1 h and then filtered through a pad of Celite®. The pad of Celite® was washed with 200 mL of distilled water then washed with 200 mL of acetone. The filtrate was concentrated in vacuo to a volume of approximately 200 mL. The resulting aqueous filtrate was treated with concentrated hydrochloric acid until pH=1 and then cooled using an ice/water bath. The desired product precipitated upon cooling. The solid was filtered and washed well with cold distilled water to provide 3-carboxyphenylboronic acid as a cream-colored solid which was used without further purification. (Yield 1.95 g, 53%; mp 232–234° C.).

Step B:

A solution of (Z)-1,3-dihydro-4-iodo-3-[(1H-pyrrol-2-yl) methylene]-2H-indol-2-one (30 mg, 0.089 mmol) (Starting Material 1), 2M aqueous Na$_2$CO$_3$ solution (150 μL, 0.300 mmol), (Ph$_3$P)$_2$PdCl$_2$ (4 mg, 0.006 mmol)(Aldrich), and 3-carboxyphenylboronic acid (17 mg, 0.102 mmol) (from Step A above) in 4 mL of a 3:1 mixture of 1,2-dimethoxyethane:distilled water was heated at 95° C. under a nitrogen atmosphere for 24 h. The reaction mixture was allowed to cool to room temperature and then directly purified by flash chromatography (Merck Silica gel 60, 230–400 mesh, 50% ethyl acetate-hexanes then 100% ethyl acetate with 1% glacial acetic acid elution) to provide pure (Z)-3-[2,3-dihydro-2-oxo-3-[(1H-pyrrol- 2-yl)methylene1-1H-indol-4-yl]-benzoic acid (yield: 23 mg, 78%) as an orange solid (mp 233–235° C.).

Example 30

(Z)-N-[2-[[3-[2,3-Dihydro-2-oxo-3-[(1H-pyrrol-2-yl) methylene]-1H-indol-4-yl]phenyl]amino]-2-oxoethyl]-4-(fluorosulfonyl)benzamide (CC)

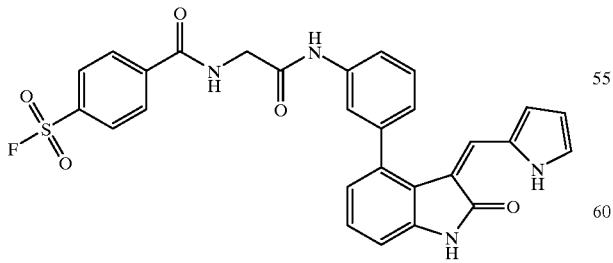

Step A:

A solution of glycine tert-butyl ester hydrochloride (300 mg, 1.79 mmol) (Aldrich), Et$_3$N (250 μL, 1.79 mmol), and 4-(fluorosulfonyl)benzoyl chloride (400 mg, 1.79 mmol) (Aldrich) in 9 mL of dry N,N-dimethylformamide was stirred at room temperature under a nitrogen atmosphere for 12 h. The reaction mixture was diluted with ethyl acetate. The organic phase was washed with distilled water, dried over sodium sulfate, filtered, and concentrated in vacuo to provide crude (4-fluorosulfonyl-benzoylamino)-acetic acid tert-butyl ester (541 mg, 95%) as an oil that solidified upon sitting at room temperature. The crude (4-fluorosulfonyl-benzoylamino)-acetic acid tert-butyl ester was used without further purification.

Step B:

A solution of the crude (4-fluorosulfonyl-benzoylamino)-acetic acid tert-butyl ester (541 mg, 1.70 mmol) (from step A above) in 2 mL of methylene chloride was treated with 2 mL of trifluoroacetic acid. The reaction mixture was stirred at room temperature for 72 h. The reaction mixture was concentrated in vacuo to provide crude (4-fluorosulfonyl-benzoylamino)-acetic acid (407.9 mg, 92%) as a solid that was used without further purification.

Step C:

A solution of (Z)-4-(3-aminophenyl)-1,3-dihydro-3-[(1H-pyrrol-2-yl)methylene]-2H-indol-2-one (30 mg, 0.100 mmol) (from Example 4 supra), crude (4-fluorosulfonyl-benzoylamino)-acetic acid (28 mg, 0.107 mmol) (from step B above), O-benzotriazol-1-yl-N,N,N',N'-tetramethyluronium hexafluorophosphate (HBTU, 45 mg, 0.119 mmol) (Advance ChemTech), 1-hydroxybenzotriazole hydrate (HOBT, 16 mg, 0.118 mmol) (Aldrich), and N,N-diisopropylethylamine (52 μL, 0.300 mmol) (Aldrich) in 3 mL of dry N,N-dimethylformamide (Fisher Scientific) was stirred at 50° C. under a nitrogen atmosphere for 7 h then stirred at room temperature under a nitrogen atmosphere for 12 h. The reaction mixture was diluted with 40 mL ethyl acetate and washed with distilled water. The organic phase was concentrated in vacuo. Flash chromatography (Merck Silica gel 60, 230–400 mesh, 40% acetone-hexanes then 70% acetone-hexanes elution) provided pure (Z)-N-[2-[[3-[2,3-dihydro-2-oxo-3-[(1H-pyrrol-2-yl)methylene]-1H-indol-4-yl] phenyl]amino]-2-oxoethyl]-4-(fluorosulfonyl)benzamide (yield: 13 mg, 24%) as a yellow solid (mp 248–250° C.).

Example 31

(Z)-N-[3-[2,3-Dihydro-2-oxo-3-[(1H-pyrrol-2-yl) methylene]-1H-indol-4-yl]phenyl]-4-(phenylsulfonyl)-2-thiophenesulfonamide (DD)

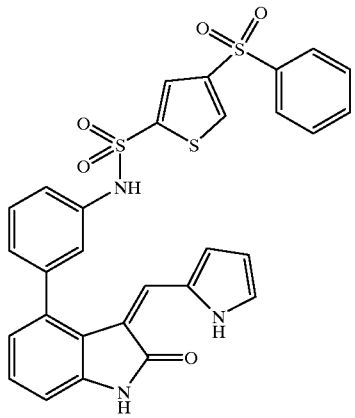

A solution of (Z)-4-(3-aminophenyl)-1,3-dihydro-3-[(1H-pyrrol-2-yl)methylene]-2H-indol-2-one (60 mg, 0.200 mmol) (from Example 4 supra), Et₃N (28 μL, 0.201 mmol), and 4-benzenesulfonylthiophene-2-sulfonyl chloride (64.6 mg, 0.200 mmol) (Lancaster) in 7 mL of 1,2-dimethoxyethane (Fisher Scientific) was heated at reflux for 1 h. The reaction mixture was allowed to cool and then stirred at room temperature for 15 h. The reaction mixture was concentrated in vacuo. Flash chromatography (Merck Silica gel 60, 230–400 mesh, 45% ethyl acetate-hexanes elution) provided pure (Z)-N-[3-[2,3-dihydro-2-oxo-3-[(1H-pyrrol-2-yl)methylene]-1H-indol-4-yl]phenyl]-4-(phenylsulfonyl)-2-thiophenesulfonamide (yield: 42 mg, 36%) as a yellow solid (mp 132–134° C.) (solid to gel).

Example 32
(Z)-4-(3-Aminophenyl)-1,3-dihydro-3-[(3-methoxy-1H-pyrrol-2-yl)methylene]-2H-indol-2-one (EE)

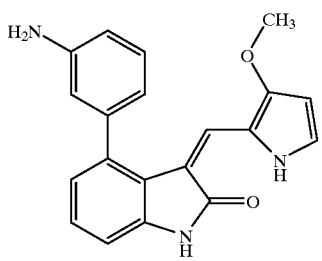

Using Method S above, 3-aminophenyl boronic acid (0.16 g, 1.0 mmol) (Lancaster) was coupled with (Z)-4-bromo-1,3-dihydro-3-[(3-methoxy-1H-pyrrol-2-yl)methylene]-2H-indol-2-one (0.3 g, 0.94 mmol) (Starting Material 7) using (Ph₃P)₄Pd (0.11 g) as catalyst in aqueous 2M Na₂CO₃ (0.94 mL, 1.88 mmol) and DME (20 mL) at reflux for 1 day to produce (Z)-4-(3-aminophenyl)-1,3-dihydro-3-[(3-methoxy-1H-pyrrol-2-yl)methylene]-2H-indol-2-one (yield: 0.2 g, 65%).

Example 33
(Z)-1,3-Dihydro-4-(2,4-dimethoxy-6-pyrimidinyl)-3-[(3-methoxy-1H-pyrrol-2-yl)methylene]-2H-indol-2one (FF)

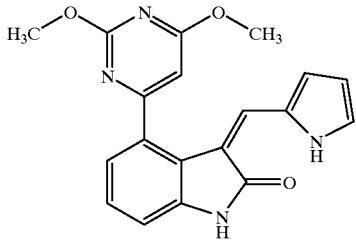

A solution of 2,4dimethoxy-6-(tributylstannyl)-pyimidine (137 mg, 0.32 mmol) (Starting Material 8) and (Z)-4-bromo-1,3-dihydro-3-[(1H-pyrrol-2-yl)methylene]-2H-indol-2-one (80 mg, 0.30 mmol) (Starting Material 2) in 3 mL dimethylformamide and 3 mL triethylamine was degassed by bubbling argon through the solution for 15 minutes. At this time (Ph₃P)₂PdCl₂ (25 mg) (Aldrich) was added and the mixture heated at 70° C. for 18 h. After cooling, water (20 mL) was added and the precipitate was filtered off and dried. The product was purified via flash column chromatography (SiO₂, 230–400 mesh with ethyl acetate/hexanes as solvent) to yield (Z)-1,3-dihydro-4-(2,4-dimethoxy-6-pyrimidinyl)-3-[(3-methoxy-1H-pyrrol-2-yl)methylene]-2H-indol-2-one. (Yield 51 mg, 49%).

Example 34
(Z)-1,3-Dihydro-4-phenyl-3-[(3-methoxy-1H-pyrrol-2-yl)methylene]-2H-indol-2-one (GG)

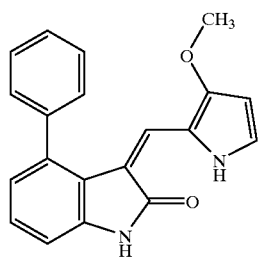

Using Method S above, phenyl boronic acid (86 mg, 0.70 mmol) (Aldrich) was coupled with (Z)-4-bromo-1,3-dihydro-3-[(3-methoxy-1H-pyrrol-2-yl)methylene]-2H-indol-2-one (150 mg, 0.47 mmol) (Starting Material 7) using (Ph₃P)₄Pd (27 mg) (Aldrich) as catalyst in aqueous 2M Na₂CO₃ (0.47 mL, 0.94 mmol) and DME (10 mL) at reflux for 2 days to give (Z)-1,3-dihydro-4-phenyl-3-[(3-methoxy-1H-pyrrol-2-yl)methylene]-2H-indol-2-one (yield: 35 mg, 23%).

Example 35

(Z)-1,3-Dihydro-4-(4-hydroxyphenyl)-3-[(3-methoxy-1H-pyrrol-2-yl)methylene]-2H-indol-2-one (HH)

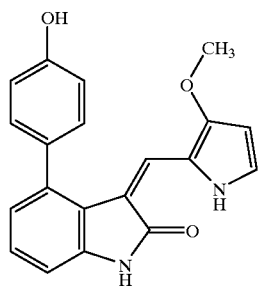

In accordance with Method S above, 4-hydroxy-phenyl boronic acid (96.6 mg, 0.70 mmol) (see Gilman, supra) was coupled with (Z)-4-bromo-1,3-dihydro-3-[(3-methoxy-1H-pyrrol-2-yl)methylene]-2H-indol-2-one (150 mg, 0.47 mmol) (Starting Material 7) using (Ph₃P)₄Pd (27 mg) (Aldrich) as catalyst in aqueous 2M Na₂CO₃ (0.47 mL, 0.94 mmol) and DME (10 mL) at reflux for 2 days to give (Z)-1,3-dihydro-4-(4-hydroxyphenyl)-3-[(3-methoxy-1H-pyrrol-2-yl)methylene]-2H-indol-2-one (yield: 60 mg, 73%, based on 70 mg recovered starting oxindole).

Example 36

(Z)-4-[2,3-Dihydro-3-[(3-methoxy-1H-pyrrol-2-yl)methylene]-2-oxo-1H-indol-4-yl]-benzoic acid (II)

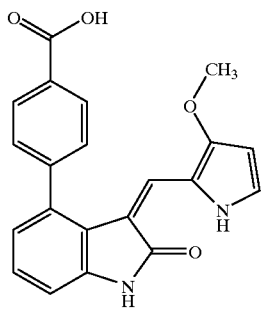

Using Method S above, 4-carboxy-phenyl boronic acid (27.2 mg, 0.164 mmol) (Lancaster) was coupled with (Z)-1,3-dihydro-4-iodo-3-[(3-methoxy-1H-pyrrol-2-yl)methylene]-2H-indol-2-one (50 mg, 0.137 mmol) (Starting Material 3) using (Ph₃P)₄Pd (4.8 mg) (Aldrich) as catalyst in DME (5 mL) and solid Na₂CO₃ (51 mg, 0.48 mmol) at reflux for 18 h to give (Z)-4-[2,3-dihydro-3-[(3-methoxy-1H-pyrrol-2-yl)methylene]-2-oxo-1H-indol-4-yl]-benzoic acid (yield: 15 mg, 31%).

Example 37
(Z)-1,3-Dihydro-4-(4-hydroxyphenyl)-3-[(3-methoxy-1H-pyrrol-2-yl)methylene]-5-nitro-2H-indol-2-one (JJ)

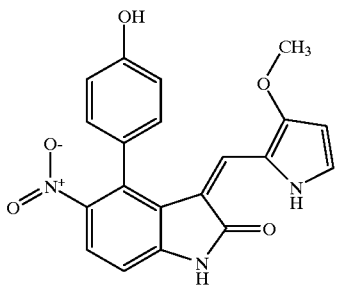

Using Method S above, 4-hydroxyphenyl boronic acid (85.0 mg, 0.62 mmol) (see Gilman, supra) was coupled with (Z)-4-bromo-1,3-dihydro-3-[(3-methoxy-1H-pyrrol-2-yl)methylene]-5-nitro-2H-indol-2-one (150 mg, 0.41 mmol) (Starting Material 6) using DPPFPdCl₂ (17 mg) (Aldrich) as catalyst in aqueous 2M Na₂CO₃ (0.42 mL, 0.84 mmol) and DME (15 mL) at reflux for 1 day to give (Z)-1,3-dihydro-4-(4-hydroxyphenyl)-3-[(3-methoxy-1H-pyrrol-2-yl)methylene]-5-nitro-2H-indol-2-one (yield: 11 0 mg, 52%).

Example 38
(Z)-1,3-Dihydro-3-[(3-methoxy-1H-pyrrol-2-yl)methylene]-5-nitro-4-phenyl-2H-indol-2-one (KK)

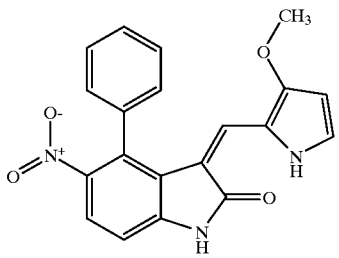

Using Method S above, phenyl boronic acid (75.2 mg, 0.617 mmol) (Aldrich) was coupled with (Z)-4-bromo-1,3-dihydro-3-[(3-methoxy-1H-pyrrol-2-yl)methylene]-5-nitro-2H-indol-2-one (150 mg, 0.41 mmol) (Starting Material 6) using DPPFPdCl₂ (17 mg) (Aldrich) as catalyst in aqueous 2M Na₂CO₃ (0.42 mL, 0.84 mmol) and DME (15 mL) at reflux for 18 h to give (Z)-1,3-dihydro-3-[(3-methoxy-1H-pyrrol-2-yl)methylene]-5-nitro-4-phenyl-2H-indol-2-one (yield: 120 mg, 80%).

Example 39
(Z)-N-[2,3-Dihydro-3-[(3-methoxy-1H-pyrrol-2-yl)methylene]-2-oxo-4-phenyl-1H-indol-5-yl]-2-thiopheneacetamide (LL)

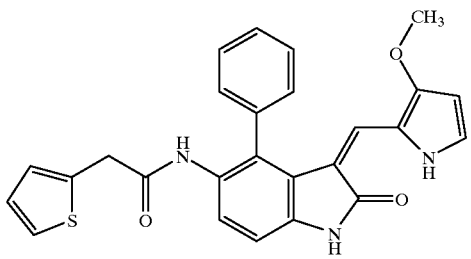

Using Method M above, (Z)-5-amino-1,3-dihydro-3-[(3-methoxy-1H-pyrrol-2-yl)methylene]-4-phenyl-2H-indol-2-one (26.5 mg, 0.08 mmol) (from Example 43 infra) was acylated with 2-thiopheneacetyl chloride (25.7 mg, 0.16 mmol) (Aldrich) in saturated aqueous NaHCO₃ (0.16 mL) and THF (2 mL) at room temperature for 3 h to give (Z)-N-[2,3-dihydro-3-[(3-methoxy-1H-pyrrol-2-yl)methylene]-2-oxo-4-phenyl-1H-indol-5-yl]-2-thiopheneacetamide (yield: 24 mg, 67%).

Example 40
(Z)-1,3-Dihydro-4-(5-indolyl)-3-[(3-methoxy-1H-pyrrol-2-yl)methylene]-2H-indol-2-one (MM)

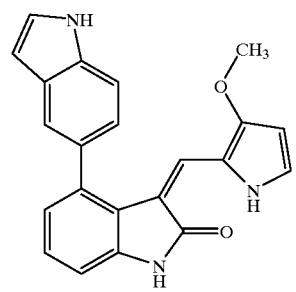

Step A: 5-Indoleboronic Acid
To a suspension of sodium hydride (122 mg, 5.1 mmol) in anhydrous tetrahydrofuran (20 mL) was added 5-bromoindole (1.0 g, 5.1 mmol) (Aldrich) at 0° C. After 15 min. of stirring at 0° C., the reaction was cooled to −78° C., and tert-butyllithium (10.2 mmol, 1.7M in hexane) (Aldrich) was added dropwise (a white precipitate immediately formed). After 10 min. tri-n-butylborate (2.75 mL, 10.2 mmol) was added dropwise. The reaction was allowed to slowly warm to room temperature, then the suspension was poured into an ice cold solution of 1N HCl. The organic phase was separated, and the aqueous phase was washed with ether. The combined organic extracts were extracted with 1N NaOH (3×25 mL), and the combined alkaline extracts were acidified to pH 1 with 1N HCl. The product was then extracted with ether, and the combined ether layers were dried over magnesium sulfate and concentrated in vacuo to yield a brownish solid. The product was recrystallized from boiling water to yield 450 mg (55%) white crystals (mp >290° C.).

Step B: (Z)-1,3-Dihydro 4-(5-indolyl)-3-[(3-methoxy-H-pyrrol-2-yl)methylene]-2H-indol-2-one A solution of 5-indoleboronic acid (36 mg, 0.22 mmol) (from Step A above), (Z)-1,3-dihydro-4-iodo-3-[(3-methoxy-1H-pyrrol-2-yl)methylene]-2H-indol-2-one (54 mg, 0.15 mmol) (Starting Material 3), and sodium carbonate (52 mg, 0.49 mmol) in 5 mL DME and 2.5 mL water was degassed for 15 min. by bubbling argon through the solution. Dichlorobis(triphenylphosphine)palladium (II) (11 mg) (Aldrich) was then added and the reaction was heated at 90° C. for 2 days. The reaction was then poured into 100 mL water and the product was extracted with ethyl acetate (4×50 mL). The combined organic layers were dried over magnesium sulfate and concentrated in vacuo. The product was purified via flash column chromatography (1% CH$_3$OH in CHCl$_3$) to yield 33 mg (62%) orange powder.

Example 41
(Z)-5-Amino-1,3-dihydro-4-(4-hydroxyphenyl)-3-[(3-methoxy-1H-pyrrol-2-yl)methylene]-2H-indol-2-one (NN)

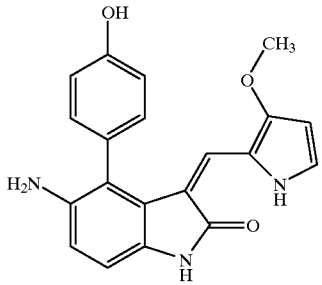

Using Method L above, (Z)-1,3-dihydro-4-(4-hydroxyphenyl)-3-[(3-methoxy-1H-pyrrol-2-yl)methylene]-5-nitro-2H-indol-2-one (84 mg, 0.22 mmol) (from Example 37 supra) was reduced with zinc (130 mg, 2.0 mmol) and ammonium chloride (25.9 mg, 0.48 mmol) in 10% water in methanol (20 mL) at reflux for 18 h to give (Z)-5-amino-1,3-dihydro-4-(4-hydroxyphenyl)-3-[(3-methoxy-1H-pyrrol-2-yl)methylene]-2H-indol-2-one (yield: 38 mg, 49%).

Example 42
(Z)-N-[2,3-Dihydro-4-(4-hydroxyphenyl)-3-[(3-methoxy-1H-pyrrol-2-yl)methylene]-2-oxo-1H-indol-5-yl]-2-thiopheneacetamide (OO)

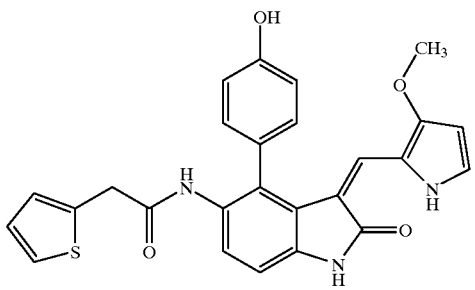

Using Method M above, (Z)-5-amino-1,3-dihydro-4-(4-hydroxyphenyl)-3-[(3-methoxy-1H-pyrrol-2-yl)methylene]-2H-indol-2-one (28 mg, 0.08 mmol) (from Example 41 supra) was acylated with 2-thiopheneacetyl chloride (25.7 mg, 0.16 mmol) (Aldrich) in saturated aqueous NaHCO$_3$ (0.16 mL) and THF (2 mL) at room temperature for 3 h to give (Z)-N-[2,3-dihydro-4-(4-hydroxyphenyl)-3-[(3-methoxy-1H-pyrrol-2-yl)methylene]-2-oxo-1H-indol-5-yl]-2-thiopheneacetamide (yield: 16 mg, 42%).

Example 43
(Z)-5-Amino-1,3-dihydro-3-[(3-methoxy-1H-pyrrol-2-yl)methylene]-4-phenyl-2H-indol-2-one (PP)

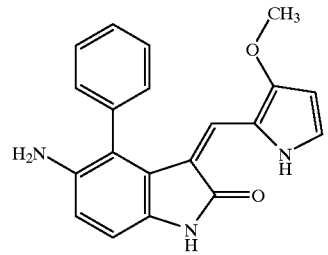

Using Method L above, (Z)-1,3-dihydro-3-[(3-methoxy-1H-pyrrol-2-yl)methylene]-5-nitro-4-phenyl-2H-indol-2-one (30 mg, 0.08 mmol) (from Example 38 supra) was reduced with zinc (48.9 mg, 0.75 mmol) and ammonium chloride (9.4 mg, 0.18 mmol) in 10% water in methanol (10 mL) at reflux for 1 day to give (Z)-5-amino-1,3-dihydro-3-[(3-methoxy-1H-pyrrol-2-yl)methylene]-4-phenyl-2H-indol-2-one (yield: 26.5 mg, 100%).

Example 44
(Z)-N-[2,3-dihydro-4-(5-indolyl)-3-[(3-methoxy-1H-pyrrol-2-yl)methylene]-2-oxo-1H-indol-5-yl]-2-thiopheneacetamide (QQ)

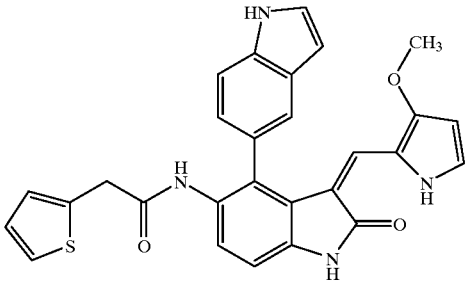

Step A: (Z)-1,3-dihydro-4-(5-indolyl)-3-[(3-methoxy-1H-pyrrol-2-yl)methylene]-5-nitro-2H-indol-2-one

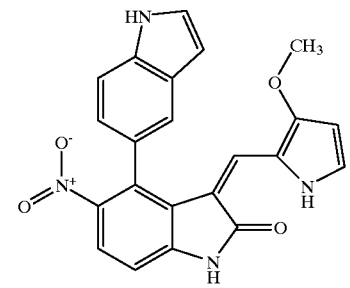

A solution of (Z)-4-bromo-1,3-dihydro-3-[(3-methoxy-1H-pyrrol-2-yl)methylene]-5-nitro-2H-indol-2-one (112 mg, 0.31 mmol) (Starting Material 6), 5-indoleboronic acid (71 mg, 0.44 mmol) (from Example 40, Step A, supra) and sodium carbonate (110 mg, 1.03 mmol) were dissolved in 10 mL DMF and 5 mL water. The solution was degassed for 30 minutes by bubbling argon through the solution. At this time, dichlorobis(triphenylphosphine) palladium(II) (11 mg) (Aldrich) was added, and the reaction was heated, under argon, at 90° C. for 2 days. Water (20 mL) was then added and the precipitate was filtered off and dried. The product was purified via flash column chromatography (SiO$_2$, 230–400 mesh) with 5% MeOH/CHCl$_3$ to give (Z)-1,3-dihydro-4-(5-indolyl)-3-[(3-methoxy-1H-pyrrol-2-yl) methylene]-5-nitro-2H-indol-2-one as a red powder. (Yield 38 mg, 76%).

Step B: (Z)-5-Amino-1,3-dihydro-4-(5-indolyl)-3-[(3-methoxy-1H-pyrrol-2-yl)methylone]-2H-indol-2-one

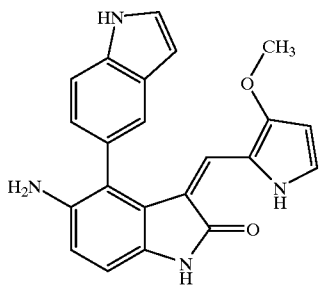

To a solution of (Z)-1,3-dihydro-4-(5-indolyl)-3-[(3-methoxy-1H-pyrrol-2-yl)methylene]-5-nitro-2H-indol-2-one (33 mg, 0.08 mmol) (from Step A above) in 1 mL of a 10% water in methanol solution and 0.5 mL THF was added zinc dust (145 mg, 2.21 mmol) followed by ammonium chloride (14 mg, 0.26 mmol). The reaction was heated at gentle reflux for 4 hours, at which time the reaction mixture was filtered through a pad of Celite® and rinsed thoroughly with ethyl acetate. The resulting solution was diluted with 5 mL water and the product was extracted with ethyl acetate. The combined organic extracts were dried over magnesium sulfate and concentrated. The resulting powder was recrystallized from EtOAc/hex to give (Z)-5-amino-1,3-dihydro-4-(5-indolyl)-3-[(3-methoxy-1H-pyrrol-2-yl)methylene]-2H-indol-2-one as a red powder. (Yield 24 mg, 80%).

Step C: (Z)-N-[2,3-Dihydro-4-(5-indolyl)-3-[(3-methoxy-1H-pyrrol-2-yl)methylene]-2-oxo-1H-indol-5-yl]-2-thiopheneacetamide (QQ)

To a solution of (Z)-5-amino-1,3-dihydro-4-(5-indolyl)-3-[(3-methoxy-1H-pyrrol-2-yl)methylene]-2H-indol-2-one (24 mg, 0.065 mmol) (from Step B above) in 2 mL tetrahydrofuran was added 2-thiopheneacetyl chloride (24 mg, 0.15 mmol) (Aldrich) and a saturated aqueous solution of sodium bicarbonate (0.15 mL). The reaction was stirred at room temperature for 14 hours at which time the reaction was diluted with water (10 mL), and the THF was evaporated in vacuo. The product was then extracted with EtOAc, and the combined organic layers were dried over magnesium sulfate and concentrated in vacuo. The resulting powder was recrystallized from EtOAc/Hex to give product as yellow crystals. (Yield 23 mg, 72%).

Example 45

(Z)-4-[2,3-Dihydro-3-[(3-methoxy-1H-pyrrol-2-yl)methylene]-5-nitro-2oxo-1H-indol-4-yl]-benzoic acid methyl ester (RR)

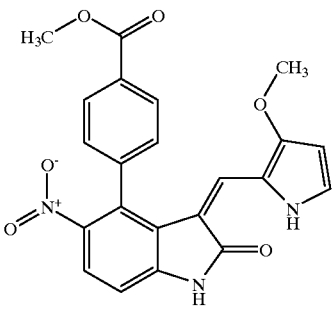

Step A: 4-Methoxycarbonyl-phenyl Boronic Acid

A solution of (trimethylsilyl)diazomethane (3 mL, 2 M in hexanes) (Aldrich) was added to a suspension of 4-carboxyphenylboronic acid (1.0 g, 6 mmol) (Lancaster) in ether (50 mL). After stirring for 2 h at room temperature, DMF (8 mL) was added to obtain a clear solution. An additional portion of (trimethylsilyl) diazomethane (3 mL, 2 M in hexanes) was added. After stirring for an additional 2 h, the reaction was quenched by adding acetic acid and concentrating under reduced pressure. Residue was recrystallized from water to give product. (Yield 0.81 9, 75%).

Step B: (Z)-4-[2,3-Dihydro-3-[(3-methoxy-1H-pyrrol-2-yl)methylene]-5-nitro-2-oxo-1H-indol-4-yl]-benzoic acid methyl ester (RR)

Using Method S above, 4-methoxycarbonyl-phenyl boronic acid (29.6 mg, 0.164 mmol) (from Step A above) was coupled with (Z)-4-bromo-1,3-dihydro-3-[(3-methoxy-1H-pyrrol-2-yl)methylene]-5-nitro-2H-indol-2-one (50 mg, 0.137 mmol) (Starting Material 6) using DPPFPdCl$_2$ (5.6 mg) (Aldrich) as catalyst in aqueous 2M Na$_2$CO$_3$ (0.14 mL, 0.28 mmol) and DME (5 mL) at reflux for 18 h to give (Z)-4-[2,3-dihydro-3-[(3-methoxy-1H-pyrrol-2-yl)methylene]-5-nitro-2-oxo-1H-indol-4-yl]-benzoic acid methyl ester (yield: 41 mg, 71%).

Example 46

(Z)-4-[5-Amino-2,3-dihydro-3-[(3-methoxy-1H-pyrrol-2-yl)methylene]-2-oxo-1H-indol-4-yl]-benzoic acid methyl ester (SS)

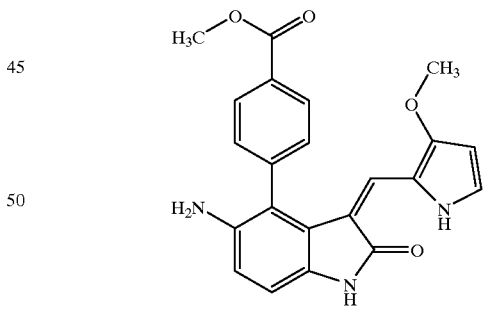

Using Method L above, (Z)-4-[2,3-dihydro-3-[(3-methoxy-1H-pyrrol-2-yl) methylene]-5-nitro-2-oxo-1H-indol-4-yl]-benzoic acid methyl ester (85 mg, 0.22 mmol) (from Example 45 supra) was reduced with zinc (130 mg, 1.97 mmol) and ammonium chloride (25.8 mg, 0.48 mmol) in 10% water in methanol (10 mL) at reflux for 2 h to yield (Z)-4-[5-amino-2,3-dihydro-3-[(3-methoxy-1H-pyrrol-2-yl)methylene]-2-oxo-1H-indol-4-yl]-benzoic acid methyl ester (yield: 40 mg, 51%).

Example 47

(Z)-1,3-Dihydro-4-(4-indolyl)-3-[(3-methoxy-1H-pyrrol-2-yl)methylene]-2H-indol-2-one (TT)

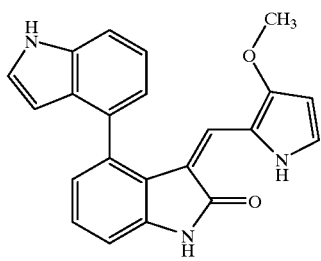

Step A: 4-Indoleboronic Acid

To a suspension of sodium hydride (130 mg, 5.41 mmol) in anhydrous tetrahydrofuran (20 mL) was added 4-bromoindole (973 mg, 4.96 mmol) (see Kosuge et al. supra) at 0° C. After 15 min. of stirring at 0° C., the reaction was cooled to −78° C., and tert-butyllithium (10.2 mmol, 1.7 M in hexane) (Aldrich) was added dropwise (a white precipitate immediately formed). After 10 min. tri-n-butylborate (2.75 mL, 10.2 mmol) (Aldrich) was added dropwise. The reaction was allowed to slowly warm to room temperature, then the suspension was poured into an ice cold solution of 1N HCl. The organic phase was separated, and the aqueous phase was washed with ether. The combined organic extracts were extracted with 1N NaOH (3×25 mL), and the combined alkaline extracts were acidified to pH 1 with 1N HCl. The product was then extracted with ether, and the combined ether layers were dried over magnesium sulfate and concentrated in vacuo to yield a brownish solid. The product was recrystallized from boiling water to yield 367 mg (46%) white crystals.

Step B: (Z)-1,3-Dihydro-4-(4-indolyl)-3-[(3-methoxy-1H-pyrrol-2-yl)methylene]-2H-indol-2-one (TT)

A solution of 4-indoleboronic acid (64 mg, 0.40 mmol) (from Step A above), (Z)-4-bromo-1,3-dihydro-3-[(3-methoxy-1H-pyrrol-2-yl)methylene]-2H-indol-2-one (100 mg, 0.31 mmol) (Starting Material 7), and sodium carbonate (35 mg, 0.33 mmol) in 3 mL DME and 1 mL water was degassed for 15 min. by bubbling argon through the solution. Dichlorobis(triphenylphosphine)palladium (II) (13 mg) (Aldrich) was then added and the reaction was heated at 90° C. for 2 days. The reaction was then poured into 100 mL water and the product was extracted with ethyl acetate (4×50 mL). The combined organic layers were dried over magnesium sulfate and concentrated in vacuo. The product was purified via flash column chromatography (1% $CH_3OH$ in $CHCl_3$) to yield 42 mg (38%) orange powder.

Example 48
(Z)-1,3-Dihydro-4-(6-indolyl)-3-[(3-methoxy-1H-pyrrol-2-yl)methylone]-2H-indol-2-one (UU)

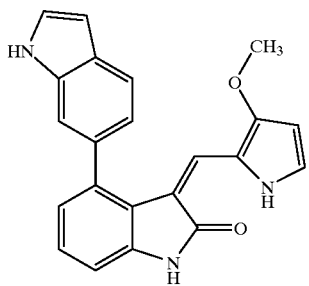

Step A: 6-Indoleboronic Acid

To a suspension of sodium hydride (130 mg, 5.41 mmol) in anhydrous tetrahydrofuran (20 mL) was added 6-bromoindole (973 mg, 4.96 mmol) (prepared according to W. A. Ayer et al., *Tetrahedron* 84(14):2919–2924 (1992)) at 0° C. After 15 min. of stirring at 0° C., the reaction was cooled to −78° C., and tert-butyllithium (10.2 mmol, 1.7 M in hexane) (Aldrich) was added dropwise (a white precipitate immediately formed). After 10 min. tri-n-butylborate (2.75 mL, 10.2 mmol) (Aldrich) was added dropwise. The reaction was allowed to warm to room temperature slowly, then the suspension was poured into an ice cold solution of 1N HCl. The organic phase was separated, and the aqueous phase was washed with ether. The combined organic extracts were extracted with 1N NaOH (3×25 mL), and the combined alkaline extracts were acidified to pH 1 with 1N HCl. The product was then extracted with ether, and the combined ether layers were dried over magnesium sulfate and concentrated in vacuo to yield a brownish solid. The product was recrystallized from boiling water to yield 412 mg (50%) white crystals.

Step B: (Z)-1,3-Dihydro-4-(6-indolyl)-3-[(3-methoxy-1H-pyrrol-2-yl)methylene]-2H-indol-2-one (UU)

A solution of 6-indoleboronic acid (36 mg, 0.22 mmol) (from Step A above), (Z)-1,3-dihydro-4-iodo-3-[(3-methoxy-1H-pyrrol-2-yl)methylene]-indol-2-one (54 mg, 0.15 mmol) (Starting Material 3) and sodium carbonate (52 mg, 0.49 mmol) in 5 mL DME and 2.5 mL water was degassed for 15 min. by bubbling argon through the solution. Dichlorobis(triphenylphosphine)palladium (II) (10 mol %) (Aldrich) was then added and the reaction was heated at 90° C. for 2 days. The reaction was then poured into 100 mL water and the product was extracted with ethyl acetate (4×50 mL). The combined organic layers were dried over magnesium sulfate and concentrated in vacuo. The resulting product, (Z)-1,3-dihydro-4-(6-indolyl)-3-[(3-methoxy-1H-pyrrol-2-yl)methylene]-2H-indol-2-one), was purified via flash column chromatography (40% EtOAc/hex) to yield 33 mg (62%) orange powder.

Example 49

(Z)-N-[2,3-Dihydro-4-(6-indolyl)-3-[(3-methoxy-1H-pyrrol-2-yl)methylene]-2-oxo-1H-indol-5-yl]-2-thiopheneacetamide (VV)

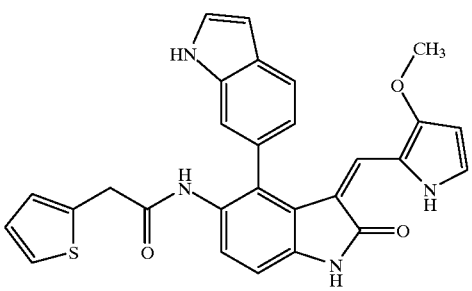

Step A: (Z)-1,3-Dihydro-4-(6-indolyl)-3-[(3-methoxy-1H-pyrrol-2-yl)methylene]-5-nitro-2H-indol-2-one

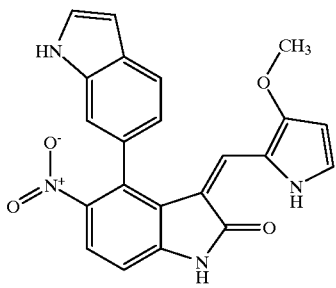

A solution of (Z)-4-bromo-1,3-dihydro-3-[(3-methoxy-1H-pyrrol-2-yl) methylene]-5-nitro-2H-indol-2-one (100 mg, 0.28 mmol) (Starting Material 6) and 6-indoleboronic acid (48 mg, 0.30 mmol) (from Example 48, Step A) were dissolved in 2 mL DMF and 2 mL triethylamine. The solution was degassed for 30 minutes by bubbling argon through the solution. At this time dichlorobis (triphenylphosphine) palladium(II) (20 mg, 0.029) (Aldrich) was added, and the reaction was heated, under argon, at 90° C. for 2 days. Water (20 mL) was then added and the precipitate was filtered off and dried. The product was purified via flash column chromatography (SiO$_2$, 230–400 mesh) with 5% MeOH/CHCl$_3$ to yield 64 mg (57%) (Z)-1, 3-dihydro-4-(6-indolyl)-3-[(3-methoxy-1H-pyrrol-2-yl) methylene]-5-nitro-2H-indol-2-one as a red powder.

Step B: (Z)-5-amino-1,3-dihydro-4-(6-indolyl)-3-[(3-methoxy-1H-pyrrol-2-yl)methylene]-2H-indol-2-one

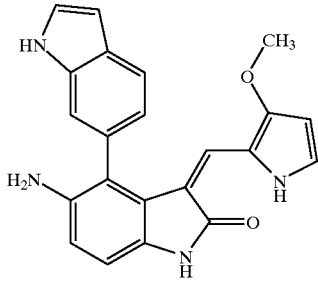

To a solution of (Z)-1,3-dihydro-4-(6-indolyl)-3-[(3-methoxy-1H-pyrrol-2-yl)methylene]-5-nitro-2H-indol-2-one (48 mg, 0.12 mmol) (from Step A above) in 2 mL of a 10% water in methanol solution and 0.5 mL THF was added zinc dust (70 mg, 1.07 mmol) followed by ammonium chloride (19 mg, 0.36 mmol). The reaction was heated at gentle reflux for 4 hours, at which time the reaction mixture was filtered through a pad of Celite® and rinsed thoroughly with ethyl acetate. The resulting solution was diluted with 5 mL water and the product was extracted with ethyl acetate. The combined organic extracts were dried over magnesium sulfate and concentrated. The resulting powder was recrystallized from EtOAc/hex to yield 25 mg (57%) of (Z)-5-amino-1,3-dihydro-4-(6-indolyl)-3-[(3-methoxy-1H-pyrrol-2-yl)methylene]-2H-indol-2-one as a red powder.

Step C: (Z)-N-[2,3-Dihydro-4-(6-indolyl)-3-[(3-methoxy-1H-pyrrol-2-yl)methylene]-2-oxo-1H-indol-5-yl]-2-thiopheneacetamide (VV)

To a solution of (Z)-5-amino-1,3-dihydro-4-(6-indolyl)-3-[(3-methoxy-1H-pyrrol-2-yl)methylene]-2H-indol-2-one (22 mg, 0.059 mmol) (from Step B above) in 2 mL tetrahydrofuran was added 2-thiopheneacetyl chloride (20 mg, 0.12 mmol) (Aldrich) and a saturated aqueous solution of sodium bicarbonate (0.15 mL). The reaction was stirred at room temperature for 16 hours at which time the reaction was diluted with water (10 mL), and the THF was evaporated in vacuo. The product was then extracted with EtOAc, and the combined organic layers were dried over magnesium sulfate and concentrated in vacuo. The resulting powder was recrystallized from EtOAc/Hex to give product as yellow crystals. (Yield 19 mg, 66%).

Example 50
(Z)-4-[2,3-Dihydro-3-[(3-methoxy-1H-pyrrol-2-yl) methylene]-2-oxo-5-[(2-thienylacetyl)amino]-1H-indol-4-yl]-benzoic Acid Methyl Ester (WW)

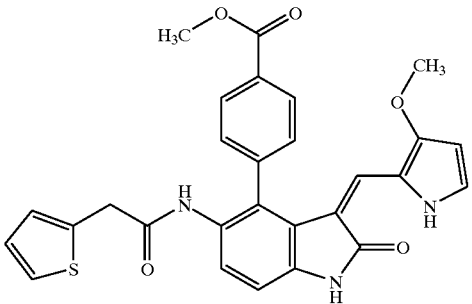

Using Method M above, (Z)-4-[5-amino-2,3-dihydro-3-[(3-methoxy-1H-pyrrol-2-yl)methylene]-2-oxo-1H-indol-4-yl]-benzoic acid methyl ester (310 mg, 0.8 mmol) (from Example 46 supra) was acylated with 2-thiopheneacetyl chloride (260 mg, 1.6 mmol) (Aldrich) in saturated aqueous NaHCO$_3$ (1.6 mL) and THF (15 mL) at room temperature for 3 h to yield (Z)-4-[2,3-dihydro-3-[(3-methoxy-1H-pyrrol-2-yl) methylene]-2-oxo-5-[(2-thienylacetyl)amino]-1H-indol-4-yl]-benzoic acid methyl ester (yield 370 mg, 90%).

Example 51
(Z)-4-[2,3-Dihydro-3-[(3-methoxy-1H-pyrrol-2-yl) methylene]-2-oxo-5-[(2-thienylacetyl)amino]-1H-indol-4-yl]-benzoic acid (XX)

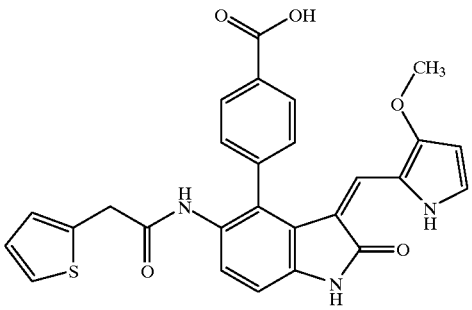

Using Method F above, (Z)-4-[2,3-dihydro-3-[(3-methoxy-1H-pyrrol-2-yl)methylene]-2-oxo-5-[(2-thienylacetyl)amino]-1H-indol-4-yl]-benzoic acid methyl ester (70 mg, 0.14 mmol) (from Example 50 supra) was hydrolyzed with LiOH.H$_2$O (20 mg, 0.48 mmol) in THF (3 mL) and water (2 mL) at room temperature for 3 days to yield (Z)-4-[2,3-dihydro-3-[(3-methoxy-1H-pyrrol-2-yl) methylene]-2-oxo-5-[(2-thienylacetyl)amino]-1H-indol-4-yl]-benzoic acid (yield: 20 mg, 29%).

Example 52
(Z)-1,3-Dihydro-3-[(4-methyl-1H-imidazol-5-yl) methylene]-5-nitro-4-phenyl-2H-indol-2-one (YY)

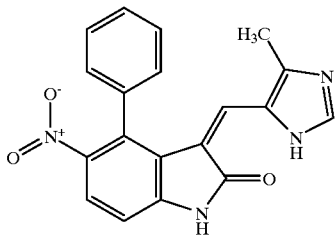

Using Method S above, (Z)-4-bromo-1,3-dihydro-3-[(4-methyl-1H-imidazol-5-yl)methylene]-5-nitro-2H-indol-2-one (100 mg, 0.29 mmol) (Starting Material 9 above) was first treated with 1,1,1,3,3,3-hexamethyidisilazane (1.53 g, 9.5 mmol) (Aldrich) then coupled with phenyl boronic acid (52.4 mg, 0.43 mmol) (Aldrich) using DPPFPdCl$_2$ (11.7 mg) (Aldrich) as catalyst in aqueous 2M Na$_2$CO$_3$ (0.29 mL, 0.58 mmol), DMF (3 mL) and DME (3 mL) at reflux for 1 day to yield (Z)-1,3-dihydro-3-[(4-methyl-1H-imidazol-5-yl)methylene]-5-nitro-4-phenyl-2H-indol-2-one (yield 9 mg, 9%).

Example 53

(Z)-1,3-Dihydro-5-fluoro-4-(4-hydroxyphenyl)-3-[(4-methyl-1H-imidazol-5-yl)methylene]-2H-indol-2-one trifluoroacetate salt (ZZ)

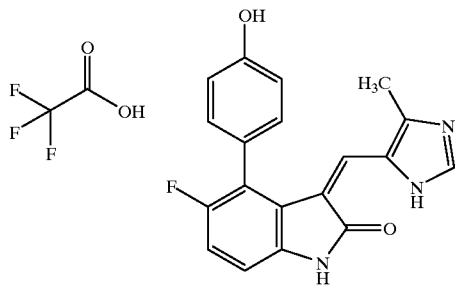

Using Method S above, 4-hydroxyphenyl boronic acid (48 mg, 0.35 mmol) (see Gilman et al., supra) was coupled with (Z)-1,3-dihydro-5-fluoro-4-iodo-3-[(4-methyl-1H-imidazol-5-yl)methylene]-2H-indol-2-one (50 mg, 0.135 mmol) (Starting Material 11 above) using DPPFPdCl$_2$ (11 mg) (Aldrich) as catalyst in aqueous 2M Na$_2$CO$_3$ (0.14 mL, 0.28 mmol), DMF (3 mL) and DME (3 mL) as solvent at reflux for 3 days to yield, after reverse phase chromatography, (Z)-1,3-dihydro-5-fluoro-4-(4-hydroxyphenyl)-3-[(4-methyl-1H-imidazol-5-yl)methylene]-2H-indol-2-one trifluoroacetate salt (yield 10 mg, 22%).

Example 54

(Z)-4-[2,3-Dihydro-5-fluoro-3-[(4-methyl-1H-imidazol-5-yl)methylene]-2-oxo-1H-indol-4-yl]-benzoic acid methyl ester trifluoroacetate Salt (AAA)

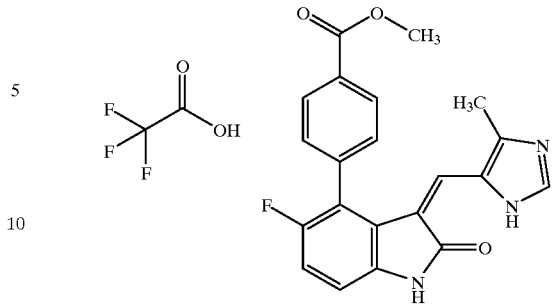

Using Method S above, 4-methoxycarbonylphenyl boronic acid (36.6 mg, 0.203 mmol) (from Example 45, Step A supra) was coupled with (Z)-1,3-dihydro-5-fluoro-4-iodo-3-[(4-methyl-1H-imidazol-5-yl)methylene]-2H-indol-2-one (50 mg, 0.135 mmol) (Starting Material 11 above) using DPPFPdCl$_2$ (11 mg) (Aldrich) as catalyst in aqueous 2M Na$_2$CO$_3$ (0.14 mL, 0.28 mmol), DMF (3 mL) and DME (3 mL) at reflux for 1 day to give (Z)-4-[2,3-dihydro-5-fluoro-3-[(4-methyl-1H-imidazol-5-yl)methylene]-2-oxo-1H-indol-4-yl]-benzoic acid methyl ester trifluoroacetate salt (yield 23 mg, 45%).

Example 55

(Z)-1,3-Dihydro-5-fluoro-4-(4-methoxyphenyl)-3-[(4-methyl-1H-imidazol-5-yl)methylene]-2H-indol-2-one trifluoroacetate salt (BBB)

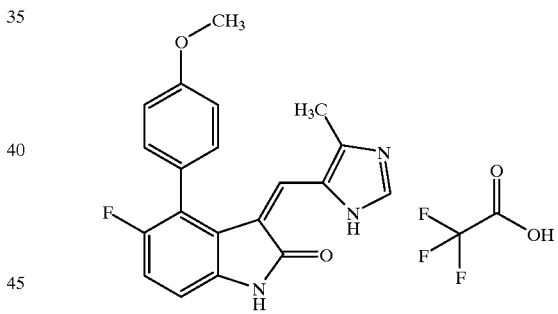

A solution of (Z)-1,3-dihydro-5-fluoro-4-iodo-3-[(4-methyl-1H-imidazol-5-yl)methylene]-2H-indol-2-one (50 mg, 0.135 mmol) (Starting Material 11), 2M aqueous Na$_2$CO$_3$ solution (0.14 mL), (Ph$_3$P)$_2$PdCl$_2$ (11 mg, 0.0135 mmol) and 4-methoxyphenylboronic acid (51.5 mg, 0.339 mmol) (Aldrich) in a 1:4 mixture of DMF:1,2-dimethoxyethane (5 mL) was heated at 104° C. for 2 days. The reaction mixture was concentrated and the crude material was purified by reverse phase HPLC to give (Z)-1,3-Dihydro-5-fluoro-4-(4-methoxyphenyl)-3-[(4-methyl-1H-imidazol-5-yl)methylene]-2H-indol-2-one trifluoroacetate salt. (Yield 18 mg, 29%).

Example 56

(Z)-1,3-Dihydro-4-(3,4-dimethoxyphenyl)-5-fluoro-3-[(4-methyl-1H-imidazol-5-yl)methylene]-2H-indol-2-one (CCC)

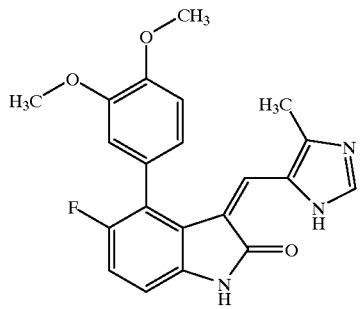

A solution of (Z)-1,3-dihydro-5-fluoro-4-iodo-3-[(4-methyl-1H-imidazol-5-yl)methylene]-2H-indol-2-one (50 mg, 0.135 mmol) (Starting Material 11), 2M aqueous Na$_2$CO$_3$ solution (0.14 mL), (Ph$_3$P)$_2$PdCl$_2$ (11 mg, 0.0135 mmol) and 3,4-dimethoxyphenylboronic acid (61.7 mg, 0.339 mmol) (Lancaster) in a 1:4 mixture of DMF:1,2-dimethoxyethane (5 mL) was heated at 104° C. for 2 days. The reaction mixture was concentrated and the crude material was purified by C18 reverse phase chromatography to give (Z)-1,3-Dihydro-4-(3,4-dimethoxyphenyl)-5-fluoro-3-[(4-methyl-1H-imidazol-5-yl)methylene]-2H-indol-2-one. (Yield 19 mg, 37%).

Example 57

(Z)-1,3-Dihydro-4-(2,4-dimethoxyphenyl)-5-fluoro-3-[(4-methyl-1H-imidazol-5-yl)methylene]-2H-indol-2-one (DDD)

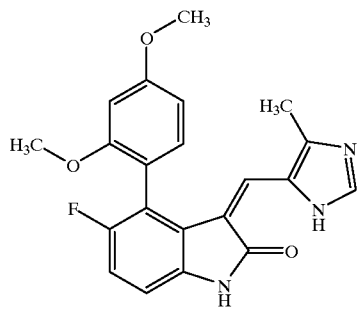

A solution of (Z)-1,3-dihydro-5-fluoro-4-iodo-3-[(4-methyl-1H-imidazol-5-yl)methylene]-2H-indol-2-one (50 mg, 0.135 mmol) (Starting Material 11), 2M aqueous Na$_2$CO$_3$ solution (0.14 mL), (Ph$_3$P)$_2$PdCl$_2$ (11 mg, 0.0135 mmol) and 2,4-dimethoxyphenylboronic acid (61.7 mg, 0.339 mmol) (Lancaster) in a 1:4 mixture of DMF:1,2-dimethoxyethane (5 mL) was heated at 104° C. for 2 days. The reaction mixture was concentrated and the crude material was purified by C18 reverse phase chromatography to give (Z)-1,3-Dihydro-4-(2,4-dimethoxyphenyl)-5-fluoro-3-[(4-methyl-1H-imidazol-5-yl)methylene]-2H-indol-2-one. (Yield 15 mg, 29%).

Example 58

(Z)-4-(1,3-Benzodioxol-5-yl)-1,3-dihydro-5-fluoro-3-[(4-methyl-1H-imidazol-5-yl)methylene]-2H-indol-2-one trifluoroacetate salt (EEE)

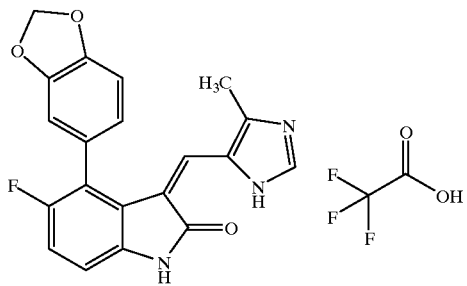

A solution of (Z)-1,3-dihydro-5-fluoro-4-iodo-3-[(4-methyl-1H-imidazol-5-yl)methylene]-2H-indol-2-one (50 mg, 0.135 mmol) (Starting Material 11), 2M aqueous Na$_2$CO$_3$ solution (0.14 mL), (Ph$_3$P)$_2$PdCl$_2$ (11 mg, 0.0135 mmol) and 3,4-methylenedioxybenzeneboronic acid (56.3 mg, 0.339 mmol) (Lancaster) in a 1:4 mixture of DMF:1,2-dimethoxyethane (5 mL) was heated at 104° C. for 2 days. The reaction mixture was concentrated and the crude material was purified by reverse phase HPLC to yield (Z)-4-(1,3-Benzodioxol-5-yl)-1,3-dihydro-5-fluoro-3-[(4-methyl-1H-imidazol-5-yl)methylene]-2H-indol-2-one trifluoroacetate salt. (Yield 23 mg, 36%).

Example 59

(Z)-4-(3-Aminophenyl)-1,3-dihydro-5-fluoro-3-[(4-methyl-1H-imidazol-5-yl)methylene]-2H-indol-2-one (FFF)

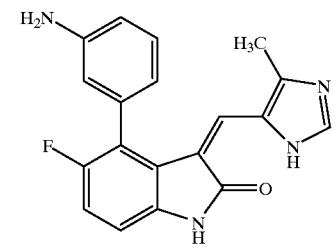

A solution of (Z)-1,3-dihydro-5-fluoro-4-iodo-3-[(4-methyl-1H-imidazol-5-yl)methylene]-2H-indol-2-one (50 mg, 0.135 mmol) (Starting Material 11), 2M aqueous Na$_2$CO$_3$ solution (0.14 mL), (Ph$_3$P)$_2$PdCl$_2$ (11 mg, 0.0135 mmol) and 3-aminobenzeneboronic acid (52.5 mg, 0.339 mmol) (Lancaster) in a 1:4 mixture of DMF:1,2-dimethoxyethane (5 mL) was heated at 104° C. for 4 days. The reaction mixture was concentrated and the crude material was purified by C18 reverse phase chromatography to give (Z)-4-(3-Aminophenyl)-1,3-dihydro-5-fluoro-3-[(4-methyl-1H-imidazol-5-yl)methylene]-2H-indol-2-one. (Yield 18 mg, 40%).

Example 60

(Z)-4-(3-Amino-4-methyl-phenyl)-1,3-dihydro-5-fluoro-3-[(4-methyl-1H-imidazol-5-yl)methylene]-2H-indol-2-one (GGG)

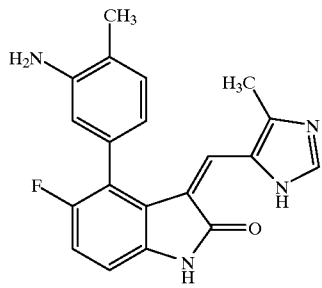

3-Amino-4-methylphenylboronic acid was prepared by hydrogenation of 4-methyl-3-nitrophenyl-boronic acid (TCI).

A solution of (Z)-1,3-dihydro-5-fluoro-4-iodo-3-[(4-methyl-1H-imidazol-5-yl)methylene]-2H-indol-2-one (50 mg, 0.135 mmol) (Starting Material 11), 2M aqueous $Na_2CO_3$ solution (0.14 mL), $(Ph_3P)_2PdCl_2$ (11 mg, 0.0135 mmol) and 3-amino-4-methylphenylboronic acid (51.2 mg, 0.339 mmol) in a 1:4 mixture of DMF:1,2-dimethoxyethane (5 mL) was heated at 104° C. for 4 days. The reaction mixture was concentrated and the crude material was purified by C18 reverse phase chromatography to give (Z)-4-(3-Amino-4-methyl-phenyl)-1,3-dihydro-5-fluoro-3-[(4-methyl-1H-imidazol-5-yl)methylene]-2H-indol-2-one. (Yield 19 mg, 40%).

Example 61
(Z)-1,3-Dihydro-5-fluoro-4-(3-hydroxyphenyl)-3-[(4-methyl-1H-imidazol-5-yl)methylene]-2H-indol-2-one (HHH)

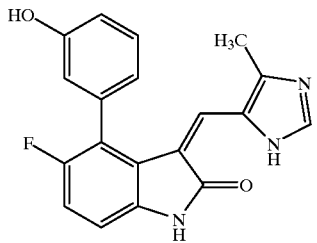

3-tert-Butyl-dimethyl-silyloxy-phenylboronic acid was prepared according to the procedure for preparing 4-tert-butyl-dimethyl-silyloxy-phenylboronic acid of: S. Yonezawa et al., Total Synthesis of Terprenin, a Novel Immunosuppressive p-Terphenyl Derivative. *J. Org. Chem.* 1998, 63, 5831–5837.

A solution of (Z)-1,3-dihydro-5-fluoro-4-iodo-3-[(4-methyl-1H-imidazol-5-yl)methylene]-2H-indol-2-one (50 mg, 0.135 mmol) (Starting Material 11), 2M aqueous $Na_2CO_3$ solution (0.14 mL), $(Ph_3P)_2PdCl_2$ (11 mg, 0.0135 mmol) and 3-tert-butyl-dimethyl-silyloxy-phenylboronic acid (0.14 g, 0.54 mmol) in 5 ml of a 1:4 mixture of DMF:1,2-dimethoxyethane (5 mL) was heated at 104° C. for 3 days. The reaction mixture was concentrated and the crude material was washed with methanol to give (Z)-1,3-Dihydro-5-fluoro-4-(3-hydroxyphenyl)-3-[(4-methyl-1H-imidazol-5-yl)methylene]-2H-indol-2-one. (Yield 10 mg, 22%).

Example 62
(Z)-1,3-Dihydro-5-fluoro-4-(4-hydroxyphenyl)-3-[(1H-pyrrol-2-yl)methylene]-2H-indol-2one (III)

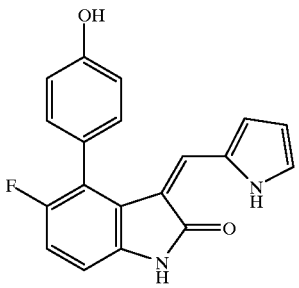

4-Hydroxyphenylboronic acid was prepared according to the procedure of H. Gilman et al., Hydroxybenzeneboronic Acids and Anhydrides. *J. Am. Chem. Soc.* 1957, 79, 3077–3081.

A solution of (Z)-1,3-dihydro-5-fluoro-4-iodo-3-[(1H-pyrrol-2-yl)methylene]-2H-indol-2-one (100 mg, 0.28 mmol) (Starting Material 12), 2M aqueous $Na_2CO_3$ solution (0.28 mL), $(Ph_3P)_2PdCl_2$ (22.9 mg, 0.028 mmol) and 4-hydroxyphenylboronic acid (77.2 mg, 0.56 mmol) in 1,2-dimethoxyethane (10 mL) was heated at 104° C. for 2 days. The reaction mixture was filtered and concentrated. The crude material was purified by reverse phase HPLC to give (Z)-1,3-Dihydro-5-fluoro-4-(4-hydroxyphenyl)-3-[(1H-pyrrol-2-yl)methylene]-2H-indol-2-one. (Yield 55mg, 61%).

Example 63
(Z)-1,3-Dihydro-5-fluoro-4-(4-hydroxyphenyl)-3-[(3-methoxy-1H-pyrrol-2-yl)methylene]-2H-indol-2-one (JJJ)

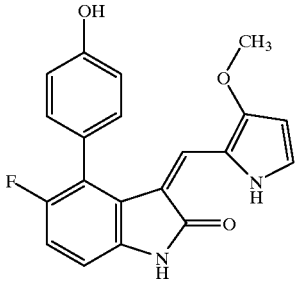

A solution of (Z)-1,3-dihydro-5-fluoro-4-iodo-3-[(3-methoxy-1H-pyrrol-2-yl)methylene]-2H-indol-2-one (100 mg, 0.26 mmol) (Starting Material 13), 2M aqueous $Na_2CO_3$ solution (0.26 mL), $(Ph_3P)_2PdCl_2$ (21.2 mg, 0.026 mmol) and 4-hydroxyphenylboronic acid (53.9 mg, 0.39 mmol) in 1,2-dimethoxyethane (10 mL) was heated at 104° C. for 4 days. The reaction mixture was filtered and concentrated. The crude material was purified by reverse phase HPLC to give (Z)-1,3-Dihydro-5-fluoro-4-(4-hydroxyphenyl)-3-[(3-methoxy-1H-pyrrol-2-yl)methylene]-2H-indol-2-one. (Yield 41 mg, 45%).

Example 64
2-[3-[5-Fluoro-3-[(3-methoxy-1H-pyrrol-2-yl)methylene]-2-oxo-2,3-dihydro-1H-indol-4-yl]-phenylamino]-acetamide (KKK)

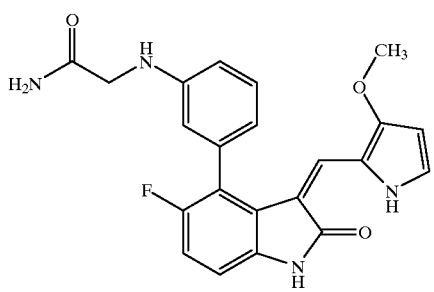

3-(Carbamoylmethyl-amino)-phenylboronic acid was prepared according to the procedure of A. H. Soloway et al., Acylation and alkylation of aminoboronic acid. *J. Org. Chem.* 1960, 25, 1683–1686.

A solution of (Z)-1,3-dihydro-5-fluoro-4-iodo-3-[(3-methoxy-1H-pyrrol-2-yl)methylene]-2H-indol-2-one (50 mg, 0.13 mmol), 2M aqueous $Na_2CO_3$ solution (0.13 mL) (Starting Material 13), $(Ph_3P)_2PdCl_2$ (22 mg, 0.027 mmol) and 3-(carbamoylmethyl-amino)-phenylboronic acid (55 mg, 0.26 mmol) in 1,2-dimethoxyethane (5 mL) was heated at 103° C. for 3 days. The reaction mixture was filtered and concentrated. The crude material was purified by C18 reverse phase chromatography to give 2-[3-[5-Fluoro-3-[(3-methoxy-1H-pyrrol-2-yl)methylene]-2-oxo-2,3-dihydro-1H-indol-4-yl]-phenylamino]-acetamide. (Yield 1 5mg, 28%).

Example 65
(Z)-1,3-Dihydro-5-fluoro-4-(4hydroxymethyl-3-methoxy-phenyl)-3-[(3-methoxy-1H-pyrrol-2-yl)methylene]-2H-indol-2-one (LLL)

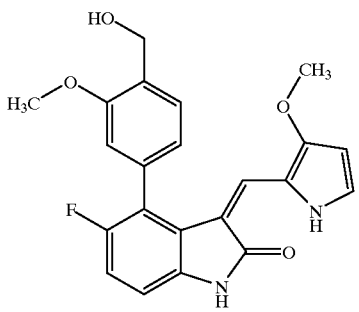

4-tert-Butyl-dimethyl-silyloxymethyl-3-methoxyphenylboronic acid was prepared according to the procedure of S. Yonezawa et al., supra.

A solution of (Z)-1,3-dihydro-5-fluoro-4-iodo-3-[(3-methoxy-1H-pyrrol-2-yl)methylene]-2H-indol-2-one (50 mg, 0.13 mmol) (Starting Material 13), 2M aqueous $Na_2CO_3$ solution (0.13 mL), $(Ph_3P)_2PdCl_2$ (11 mg, 0.013 mmol) and 4-tert-butyl-dimethyl-silyloxymethyl-3-methoxyphenylboronic acid (77 mg, 0.26 mmol) in 1,2-dimethoxyethane (5 mL) was heated at 104° C. for 1.5 days. The reaction mixture was filtered and concentrated. The crude material was purified by chromatography with silica gel eluting with EtOAc/Hexanes (3:7) to give silylated product (50 mg) which was deprotected by treatment with tetrabutyl ammonium fluoride to give (Z)-1,3-Dihydro-5-fluoro-4-(4-hydroxymethyl-3-methoxy-phenyl)-3-[(3-methoxy-1H-pyrrol-2-yl)methylene]-2H-indol-2-one. (Yield 30mg, 76%).

Example 66
SAPK Inhibitory Activity

The SAPK inhibitory activity of the compounds of the invention is demonstrated below. These effects indicate that the compounds of the present invention are useful in treating inflammatory diseases such as, for example, rheumatoid arthritis.

SAPK FlashPlate Assay

Human JNK is highly homologous to rat SAPK. To measure the inhibitory activity of test compounds, the compounds were tested in the rat SAPK assay.

For the SAPK assay, purified GST-c-Jun (a chimeric protein containing c-Jun, a natural substrate of JNK) was coated on 96 well FlashPlates (New England Nuclear, Boston, Mass.). Purified rat SAPK (isoform b, Kyriakis et al. supra) was preincubated with preparations containing MEKK-1 and MKK4 for 30 minutes at 37° C. in assay buffer containing 25 mM HEPES, pH 7.5, 150 mM NaCl, 20 mM $MgCl_2$, 2 mM DTT, 0.001% Tween 20, 1 mM ATP freshly added. In the preincubation step, MEKK-1 phosphorylates and activates MKK4, which in turn phosphorylates and activates SAPK. The activated SAPK was then added to the c-Jun coated FlashPlates along with $^{33}$P-ATP (0.32 mCi per reaction) and test compounds. The plates were incubated for 30 minutes at 37° C., then washed with PBS, 0.01% Tween 20, and counted in the Topcount scintillation counter (Packard Instrument Co., Downers Grove, Ill.). Dilutions of compounds were tested in duplicate in each assay. The percent inhibition of c-Jun phosphorylation (a measure of inhibition of SAPK activity) was determined by the following formula:

$$100 \times \left[ 1 - \frac{\text{test compound} - \text{nonspecific}}{\text{total} - \text{nonspecific}} \right]$$

where "test compound" refers to the average counts per minute of the test duplicates, "nonspecific" refers to the average counts per minute when no SAPK was added, and "total" refers to the average counts per minute when no compound was added.

The results of the SAPK assay with various test compounds is summarized below in Table I.

TABLE I

| Compound | $IC_{50}$ (μM) SAPK |
|---|---|
| C | <0.15 |
| EE | <0.15 |
| GG | <0.15 |
| JJ | <0.15 |
| KK | <0.15 |
| LL | <0.15 |
| MM | <0.15 |
| NN | <0.15 |
| OO | <0.15 |
| PP | <0.15 |
| QQ | <0.15 |
| RR | <0.15 |
| SS | <0.15 |
| TT | <0.15 |
| UU | <0.15 |
| VV | <0.15 |
| WW | <0.15 |
| XX | <0.15 |

U937 Cell-Based Assay

The U937 cells, a human monocyte/macrophage cell line, was obtained from the ATTC and grown in the recommended medium. These cells when stimulated with lipopolysaccharide (LPS) release TNF, another inflammatory mediator implicated in the JNK pathway (Swantek et al., supra) and IL-6. In this assay the ability of a test compound to block TNF expression is evaluated.

The U937 cells were suspension cells which when stimulated with phorbol myristate acetate (PMA) (Sigma, St. Louis, Mo.) became adherent. After PMA stimulation the cells were washed in cell culture medium and plated at $1 \times 10^5$ cells/well in 96 well plates. The following day the test compounds and dexamethasone control (Sigma, St. Louis, Mo.) were added to the cells for 1 hour of preincubation. Then the cells were stimulated with LPS (Sigma, St. Louis, Mo.). After an additional 24 hours of incubation the supernatants were removed and assayed for TNF-$\alpha$ and IL-6 by ELISA. The IL-6 ELISA was run as described previously for the MG63 assay. The TNF ELISA was run using a kit supplied by Genzyme (Cambridge, Mass.).

In the ELISA, 96 well plates were coated with antibody to TNF-$\alpha$ or IL-6. Supernatants were added to the coated plates and any antigen (TNF-$\alpha$ or IL-6) in the supernatant bound to the antibody coated on the plates. The plates were then washed with PBS containing 0.05% Tween 20 (Sigma, St. Louis, Mo.) and the biotinylated secondary antibody was added. This secondary antibody binds to the already bound antigen creating a "sandwich effect". Plates were washed as described above and horseradish peroxidase (HRP)-streptavidin conjugate (Sigma, St. Louis, Mo.) was added to the plates. HRP-streptavidin bound to the biotin-antibody conjugate. The plates were washed and TMB substrate (Kirkegaard and Perry Labs, Gaithersburg, Md.) was added to the wells. This substrate changes color in the presence of HRP-streptavidin. The intensity of the color (measured at 450 nm) is proportional to the amount of TNF-$\alpha$ or IL-6 produced by the U937 cells upon exposure to LPS and the test compounds. Optical density values were converted to concentration (pg/ml or Units/ml) based on a standard curve included in the assay. $IC_{50}$ values for each test compound were determined from the linear regression of a plot of the logarithm of the concentration of compound versus amount of TNF-$\alpha$ or IL-6 secreted. (The TNF-$\alpha$ antibodies and the IL-6 antibodies were obtained from either Genzyme, Cambridge, Mass. or Pharmingen, San Diego, Calif.).

The results of this assay on various test compounds is summarized below in Table II.

TABLE II

| Compound | $IC_{50}$ (pM) in U837 Cells | |
| --- | --- | --- |
| | TNF | IL6 |
| D | 1.17 | 6.33 |
| WW | 1.35 | 7.80 |

Example 67

Tablet Formulation

| Item | Ingredients | mg/Tablet | | | | | |
| --- | --- | --- | --- | --- | --- | --- | --- |
| 1 | Compound 1* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |

-continued

| Item | Ingredients | mg/Tablet | | | | | |
| --- | --- | --- | --- | --- | --- | --- | --- |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound 1 represents a compound of the invention.

Manufacturing Procedure:

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 68

Capsule Formulation

| Item | Ingredients | mg/Capsule | | | | |
| --- | --- | --- | --- | --- | --- | --- |
| 1 | Compound 1* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound 1 represents a compound of the invention.

Manufacturing Procedure:

1. Mix Items 1, 2 and 3 in a suitable mixer for 15 minutes.
2. Add Items 4 & 5 and mix for 3 minutes.
3. Fill into a suitable capsule.

Example 69

Injection Solution/Emulsion Preparation

| Item | Ingredient | mg/mL |
| --- | --- | --- |
| 1 | Compound 1* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound 1 represents a compound of the invention.

Manufacturing Procedure:

1. Dissolve item 1 in item 2
2. Add items 3, 4 and 5 to item 6 and mix until dispersed, then homogenize.
3. Add the solution from step 1 to the mixture from step 2 and homogenize until the dispertsion is translucent.
4. Sterile filter through a 0.2 um filter and fill into vials.

Example 70
Injection Solution/Emulsion Preparation

| Item | Ingredient | mg/mL |
|---|---|---|
| 1 | Compound 1* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound 1 represents a compound of the invention.

Manufacturing Procedure:
1. Dissolve item 1 in item 2
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:
1. A compound of formula

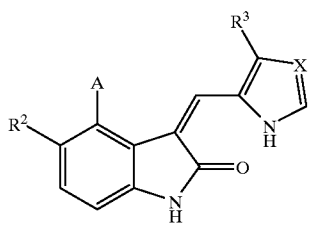

I or prodrugs or pharmaceutically active metabolites of compounds of formula I, or the pharmaceutically acceptable salts of the foregoing compounds, wherein;

A is selected from the group consisting of aryl or heteroaryl, each of which is unsubstituted or substituted by one or more substituents independently selected from the group consisting of
—H,
—$OR^4$,
—$COR^4$,
—$COOR^4$,
—$CONR^6R^7$,
—$NR^6R^7$,
—CN,
—$NO_2$,
—$SO_2R^4$,
—$SO_2NR^6R^7$,
—halogen,
—perfluoroalkyl,
lower alkyl which is unsubstituted or substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, cycloalkyl, and heterocycle,
cycloalkyl which is unsubstituted or substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, lower alkyl, and heterocycle, and
heterocycle which is unsubstituted or substituted by the group consisting of —$OR^4$, —$NR^6R^7$, —$COR^4$, —$COOR^4$, —$OCOR^4$, —$CONR^6R^7$, —CN, —$NO_2$, —$SO_2R^4$, —$SO_2NR^6R^7$, halogen, lower alkyl, and cycloalkyl;

$R^2$ is selected from the group consisting of
—H,
—$OR^4$,
—$COOR^4$,
—$CONR^6R^7$,
—$NR^6R^7$,
halogen,
—$NO_2$,
—CN,
—$SO_2NR^6R^7$,
—$SO_2R^4$
perfluoroalkyl, and
lower alkyl which is unsubstituted or substituted by the group consisting of —$OR^8$, —$NR^6R^7$, —$COR^4$, —$COOR^4$, and —$CONR^6R^7$;

$R^3$ is selected from the group consisting of
—H,
—$OR^4$,
—$COR^4$,
—$COOR^4$,
—$CONR^6R^7$,
halogen,
—CN,
—$NR^6R^7$,
perfluoroalkyl, and
lower alkyl which is unsubstituted or substituted by the group consisting of —$OR^8$ and —$NR^6R^7$;

$R^4$ is selected from the group consisting of
—H,
lower alkyl which is unsubstituted or substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$,
cycloalkyl which is unsubstituted or substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$, and
heterocycle which is unsubstituted or substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$;

$R^5$ is selected from the group consisting of
—H,
—$COR^8$,
—$CONR^8R^9$, and
lower alkyl which is unsubstituted or substituted by the group consisting of —$OR^9$, —$NR^9R^{10}$, —$N(COR^9)R^{10}$, —$COR^9$, —$CONR^9R^{10}$, and —$COOR^9$;

$R^6$ and $R^7$ are each independently selected from the group consisting of
—H,
—$COR^8$,
—$COOR^8$,
—$CONR^8R^9$,
—$SO_2R^8$,
—$SO_2NR^8R^9$,
lower alkyl which is unsubstituted or substituted by the group consisting of —OR⁵,
—COOR⁸,
—COR⁸,
—CONR⁸R⁹,
—CN,
—NO₂,
—SO₂R⁸,
—SO₂NR⁸R⁹,
—NR⁸R⁹,
cycloalkyl which is unsubstituted or substituted by the group consisting of —OR⁵, —COOR⁸, —COR⁸, —CONR⁸R⁹, —NR⁸R⁹, lower alkyl, heterocycle, —CN, —NO₂, —SO₂R⁸, and —SO₂NR⁸R⁹,
heterocycle which is unsubstituted or substituted by the group consisting of —OR⁵, —COOR⁸, —COR⁸, —CONR⁸R⁹, —NR⁸R⁹, lower alkyl, cycloalkyl, —CN, —NO₂, —SO₂R⁸, and —SO₂NR⁸R⁹,
aryl which is unsubstituted or substituted by the group consisting of —OR⁵, —COOR⁸, —COR⁸, —CONR⁸R⁹, -NR⁸R⁹, lower alkyl, cycloalkyl, heterocycle, —CN, —NO₂, —SO₂R⁸, and —SO₂NR⁸R⁹, and
heteroaryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹,
cycloalkyl which is unsubstituted or substituted by the group consisting of —OR⁵, —COOR⁸, —COR⁸, —CONR⁸R⁹, —NR⁸R⁹, lower alkyl, heterocycle, —CN, —NO₂, —SO₂R⁸, and —SO₂NR⁸R⁹,
heterocycle which is unsubstituted or substituted by the group consisting of —OR⁵, —COOR⁸, —COR⁸, —CONR⁸R⁹, —NR⁸R⁹, lower alkyl, cycloalkyl, —CN, —NO₂, —SO₂R⁸, and —SO₂NR⁸R⁹,
aryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹,
heteroaryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹, and
—NR⁶R⁷ can form a ring having 3 to 7 atoms, said ring not including any additional hetero atoms or including one or more additional hetero atoms and being unsubstituted or substituted by the group consisting of one or more of lower alkyl, —OR⁵, —COR⁸, —COOR⁸, CONR⁸R⁹, and —NR⁵R⁹;

R⁸ is selected from the group consisting of
—H,
lower alkyl which is unsubstituted or substituted by the group consisting of cycloalkyl, heterocycle, aryl, heteroaryl, —OR⁹, —NR⁹R¹⁰, and —N(COR⁹)R¹⁰,
aryl which is unsubstituted or substituted by the group consisting of —OR⁹, —COOR⁹, —COR⁹, —CONR¹⁰R⁹, —NR¹⁰R⁹, lower alkyl, cycloalkyl, heterocycle, —CN, —NO₂, —SO₂R⁹, halogen, —SO₂F and —SO₂NR¹⁰R⁹,
heteroaryl which is unsubstituted or substituted by the group consisting of —OR⁹, —COOR⁹, —COR⁹, —CONR¹⁰R⁹, —NR¹⁰R⁹, lower alkyl, cycloalkyl, heterocycle, —CN, —NO₂, —SO₂R⁹, halogen, —SO₂F and —SO₂NR¹⁰R⁹, cycloalkyl which is unsubstituted or substituted by the group consisting of —OR⁹, —COOR⁹, —COR⁹, —CONR¹⁰R⁹, —NR¹⁰R⁹, lower alkyl, heterocycle, aryl, —CN, —NO₂, —SO₂R⁹, and —SO₂NR¹⁰R⁹, and
heterocycle which is unsubstituted or substituted by the group consisting of —OR⁹, —COOR⁹, —COR⁹, —CONR¹⁰R⁹, —NR¹⁰R⁹, lower alkyl, cycloalkyl, aryl, —CN, —NO₂, —SO₂R⁹, and —SO₂NR¹⁰R⁹;

R⁹ and R¹⁰ are each independently selected from the group consisting of —H, lower alkyl and aryl; and X is selected from the group consisting of =N— and

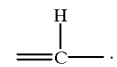

2. A compound having the formula

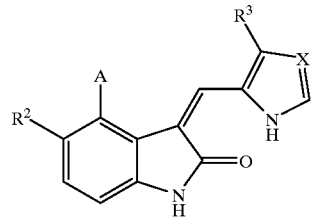

I or the pharmaceutically acceptable salts of the foregoing compound, wherein;

A is selected from the group consisting of aryl or heteroaryl, each of which is unsubstituted or substituted by one or more substituents independently selected from the group consisting of
—H,
—OR⁴,
—COR⁴,
—COOR⁴,
—CONR⁶R⁷,
—NR⁶R⁷,
—CN,
—NO₂,
—SO₂R⁴,
—SO₂NR⁶R⁷,
—halogen,
—perfluoroalkyl,
lower alkyl which is unsubstituted or substituted by the group consisting of —OR⁴, —NR⁶R⁷, —COR⁴, —COOR⁴, —OCOR⁴, —CONR⁶R⁷, —CN, —NO₂, —SO₂R⁴, —SO₂NR⁶R⁷, halogen, cycloalkyl, and heterocycle,
cycloalkyl which is unsubstituted or substituted by the group consisting of —OR⁴, —NR⁶R⁷, COR⁴, —COOR⁴, —OCOR⁴, —CONR⁶R⁷, —CN, —NO₂, —SO₂R⁴, —SO₂NR⁶R⁷, halogen, lower alkyl, and heterocycle, and
heterocycle which is unsubstituted or substituted by the group consisting of —OR⁴, and —NR⁶R⁷, —COR⁴, —COOR⁴, —OCOR⁴, —CONR⁶R⁷, —CN, —NO₂, —SO₂R⁴, —SO₂NR⁶R⁷, halogen, lower alkyl, and cycloalkyl;

R² is selected from the group consisting of
—H,
—OR⁴,
—COOR⁴,

—CONR⁶R⁷,
—NR⁶R⁷,
halogen,
—NO₂,
—CN,
—SO₂NR⁶R⁷,
—SO₂R⁴
perfluoroalkyl, and
lower alkyl which is unsubstituted or substituted by the group consisting of —OR⁸, —NR⁶R⁷, —COR⁴, —COOR⁴, and —CONR⁸R⁷;

R³ is selected from the group consisting of
—H,
—OR⁴,
—COR⁴,
—COOR⁴,
—CONR⁶R⁷,
halogen,
—CN,
—NR⁶R⁷,
perfluoroalkyl, and
lower alkyl which is unsubstituted or substituted by the group consisting of —OR⁸ and —NR⁶R⁷;

R⁴ is selected from the group consisting of
—H,
lower alkyl which is unsubstituted or substituted by the group consisting of —OR⁵, —COOR⁸, —COR⁸, —CONR⁸R⁹, —NR⁶R⁷, cycloalkyl, heterocycle, —CN, —NO₂, —SO₂R⁸, and —SO₂NR⁸R⁹,
cycloalkyl which is unsubstituted or substituted by the group consisting of —OR⁵, —COOR⁸, —COR⁸, —CONR⁸R⁹, —NR⁶R⁷, lower alkyl, heterocycle, —CN, —NO₂, —SO₂R⁸, and —SO₂NR⁸R⁹, and
heterocycle which is unsubstituted or substituted by the group consisting of —OR⁵, —COOR⁸, —COR⁸, —CONR⁸R⁹, —NR⁶R⁷, lower alkyl, cycloalkyl, —CN, —NO₂, —SO₂R⁸, and —SO₂NR⁸R⁹;

R⁵ is selected from the group consisting of
—H,
—COR⁸,
—CONR⁸R⁹, and
lower alkyl which is unsubstituted or substituted by the group consisting of —OR⁹, —NR⁹R¹⁰, —N(COR⁹)R¹⁰, —COR⁹, —CONR⁹R¹⁰, and —COOR⁹;

R⁶ and R⁷ are each independently selected from the group consisting of
—H,
—COR⁸,
—COOR⁸,
—CONR⁸R⁹,
—SO₂R⁸,
—SO₂NR⁸R⁹,
lower alkyl which is unsubstituted or substituted by the group consisting of
—OR⁵,
—COOR⁸,
—COR⁸,
—CONR⁸R⁹,
—CN,
—NO₂,
—SO₂R⁸,
—SO₂NR⁸R⁹,
—NR⁸R⁹,
cycloalkyl which is unsubstituted or substituted by the group consisting of —OR⁵, —COOR⁸, —COR⁸, —CONR⁸R⁹, —NR⁸R⁹, lower alkyl, heterocycle, —CN, —NO₂, —SO₂R⁸, and —SO₂NR⁸R⁹,
heterocycle which is unsubstituted or substituted by the group consisting of —OR⁵, —COOR⁸, —COR⁸, —CONR⁸R⁹, —NR⁸R⁹, lower alkyl, cycloalkyl, —CN, —NO₂, —SO₂R⁸, and —SO₂NR⁸R⁹,
aryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹, and
heteroaryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN,—NO₂,—SO₂R⁸, and —SO₂NR⁸R⁹,
cycloalkyl which is unsubstituted or substituted by the group consisting of —OR⁵, —COOR⁸, —COR⁸, —CONR⁸R⁹, —NR⁸R⁹, lower alkyl, heterocycle, —CN, —NO₂, —SO₂R⁸, and —SO₂NR⁸R⁹,
heterocycle which is unsubstituted or substituted by the group consisting of —OR⁵, —COOR⁸, —COR⁸, —CONR⁸R⁹, —NR⁸R⁹, lower alkyl, cycloalkyl, —CN, —NO₂, —SO₂R⁸, and —SO₂NR⁸R⁹,
aryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹,
heteroaryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹, and
—NR⁶R⁷ can form a ring having 3 to 7 atoms, said ring not including any additional hetero atoms or including one or more additional hetero atoms and being unsubstituted or substituted by the group consisting of one or more of lower alkyl, —OR⁵, —COR⁸, —COOR⁸, CONR⁸R⁹, and —NR⁵R⁹;

R⁸ is selected from the group consisting of
—H,
lower alkyl which is unsubstituted or substituted by the group consisting of cycloalkyl, heterocycle, aryl, heteroaryl, —OR⁹, —NR⁹R¹⁰, and —N(COR⁹)R¹⁰,
aryl which is unsubstituted or substituted by the group consisting of —OR⁹, —COOR⁹, —COR⁹, —CONR¹⁰R⁹, —NR¹⁰R⁹, lower alkyl, cycloalkyl, heterocycle, —CN, —NO₂, —SO₂R⁹, halogen, —SO₂F and —SO₂NR¹⁰R⁹,
heteroaryl which is unsubstituted or substituted by the group consisting of —OR⁹, —COOR⁹, —COR⁹, —CONR¹⁰R⁹, —NR¹⁰R⁹, lower alkyl, cycloalkyl, heterocycle, —CN, —NO₂, —SO₂R⁹, halogen, —SO₂F and —SO₂NR¹⁰R⁹,
cycloalkyl which is unsubstituted or substituted by the group consisting of —OR⁹, —COOR⁹, —COR⁹, —CONR¹⁰R⁹, —NR¹⁰R⁹, lower alkyl, heterocycle, aryl, —CN, —NO₂, —SO₂R⁹, and —SO₂NR¹⁰R⁹, and
heterocycle which is unsubstituted or substituted by the group consisting of —OR⁹, —COOR⁹, —COR⁹, —CONR¹⁰R⁹, —NR¹⁰R⁹, lower alkyl, cycloalkyl, aryl, —CN, —NO₂, —SO₂R⁹, and —SO₂NR¹⁰R⁹;

R⁹ and R¹⁰ are each independently selected from the group consisting of —H, lower alkyl and aryl; and X is selected from the group consisting of =N— and

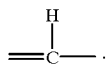

3. The compound of claim 2 wherein A is aryl or heteroaryl, each of which is unsubstituted or substituted by the group consisting of
—H,
—NR$^6$R$^7$,
—OR$^4$,
—COR$^4$,
—COOR$^4$,
—CONR$^6$R$^7$,
—SO$_2$R$^4$,
—SO$_2$NR$^6$R$^7$, and
lower alkyl which is unsubstituted or substituted by the group consisting of —OR$^5$, —NR$^6$R$^7$, —COR$^4$, —COOR$^4$, and —CONR$^6$R$^7$.

4. The compound of claim 2 wherein R$^2$ is selected from the group consisting of —H, —OR$^4$, —NO$_2$, —NR$^6$R$^7$, perfluoroalkyl, halogen, —COR$^4$, —COOR$^4$, —CONR$^6$R$^7$ and lower alkyl which is unsubstituted or substituted by the group consisting of —OR$^8$ and —NR$^6$R$^7$.

5. The compound of claim 3 wherein R$^2$ is selected from the group consisting of —H, —OR$^4$, —NR$^6$R$^7$, —NO$_2$, perfluoroalkyl, halogen, —COR$^4$, —COOR$^4$, —CONR$^6$R$^7$ and lower alkyl which is unsubstituted or substituted by the group consisting of —OR$^8$, —NR$^6$R$^7$, —COR$^4$, —COOR$^4$ and —CONR$^6$R$^7$.

6. The compound of claim 4 wherein R$^2$ is —NR$^6$R$^7$.

7. The compound of claim 5 wherein R$^2$ is —NR$^6$R$^7$.

8. The compound of claim 2 wherein R$^3$ is selected from the group consisting of —H, —OR$^4$,—NR$^6$R$^7$, and -lower alkyl which is unsubstituted or substituted by the group consisting of —OR$^8$ and —NR$^6$R$^7$.

9. The compound of claim 5 wherein R$^3$ is selected from the group consisting of —H, —OR$^4$, —NR$^6$R$^7$, and -lower alkyl which is unsubstituted or substituted by the group consisting of —OR$^8$ and —NR$^6$R$^7$.

10. The compound of claim 2 wherein R$^4$ is selected from the group consisting of —H and lower alkyl which is unsubstituted or substituted by the group consisting of —OR$^5$, —COOR$^8$, —COR$^8$, —NR$^6$R$^7$ and —CONR$^8$R$^9$.

11. The compound of claim 9 wherein R$^4$ is selected from the group consisting of —H and lower alkyl which is unsubstituted or substituted by the group consisting of —OR$^5$, —COOR$^8$, —COR$^8$, —NR$^6$R$^7$ and —CONR$^8$R$^9$.

12. The compound of claim 2 wherein R$^5$ is selected from the group consisting of —COR$^8$, —CONR$^8$R$^9$, and lower alkyl.

13. The compound of claim 11 wherein R$^5$ is selected from the group consisting of —COR$^8$, —CONR$^8$R$^9$, and lower alkyl.

14. The compound of claim 2 wherein R$^6$ and R$^7$ are each independently selected from the group consisting of —H, —COR$^8$, —COOR$^8$, —CONR$^8$R$^9$, —SO$_2$R$^8$, aryl, heteroaryl and lower alkyl which is unsubstituted or substituted by the group consisting of OR$^5$, and —NR$^8$R$^9$.

15. The compound of claim 13 wherein R$^6$ and R$^7$ are each independently selected from the group consisting of —H, —COR$^8$, —COOR$^8$, —CONR$^8$R$^9$, —SO$_2$R$^8$, aryl, heteroaryl and lower alkyl which is unsubstituted or substituted by the group consisting of OR$^5$ and —NR$^8$R$^9$.

16. The compound of claim 2 wherein R$^8$ is selected from the group consisting of —H, aryl, heteroaryl and lower alkyl which is unsubstituted or substituted by the group consisting of aryl, heteroaryl, —OR$^9$, —NR$^9$R$^{10}$, and —N(COR$^9$)R$^{10}$.

17. The compound of claim 15 wherein R$^8$ is selected from the group consisting of —H, aryl, heteroaryl and lower alkyl which is unsubstituted or substituted by the group consisting of aryl, heteroaryl, —OR$^9$, —NR$^9$R$^{10}$, and —N(COR$^9$)R$^{10}$.

18. The compound of claim 2 wherein X is =CH—.
19. The compound of claim 17 wherein X is =CH—.
20. A compound of formula

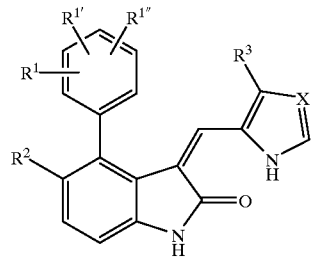

or the pharmaceutically acceptable salts of the foregoing compounds, wherein;
R$^1$, R$^{1'}$ and R$^{1''}$ are each independently selected from the group consisting of
—H,
—OR$^4$,
—COR$^4$,
—COOR$^4$,
—CONR$^6$R$^7$,
—NR$^6$R$^7$,
halogen,
—SO$_2$R$^4$,
—SO$_2$NR$^6$R$^7$,
—NO$_2$,
—CN,
perfluoroalkyl,
lower alkyl which is unsubstituted or substituted by the group consisting of —OR$^4$, —NR$^6$R$^7$, —COR$^4$, —COOR$^4$, —OCOR$^4$, —CONR$^6$R$^7$, —CN, —NO$_2$, —SO$_2$R$^4$, —SO$_2$NR$^6$R$^7$, halogen, cycloalkyl, and heterocycle,
cycloalkyl which is unsubstituted or substituted by the group consisting of —OR$^4$ and —NR$^6$R$^7$, —COR$^4$, —COOR$^4$, —OCOR$^4$, —CONR$^6$R$^7$, —CN, —NO$_2$, —SO$_2$R$^4$, —SO$_2$NR$^6$R$^7$, halogen, lower alkyl, and heterocycle, and
heterocycle which is unsubstituted or substituted by the group consisting of —OR$^4$ and —NR$^6$R$^7$, —COR$^4$, —COOR$^4$, —OCOR$^4$, —CONR$^6$R$^7$, —CN, —NO$_2$, —SO$_2$R$^4$, —SO$_2$NR$^6$R$^7$, halogen, lower alkyl, and cycloalkyl;
R$^2$ is selected from the group consisting of
—H,
—OR$^4$,
—COOR$^4$,
—CONR$^6$R$^7$,
—NR$^6$R$^7$,
halogen,
—NO$_2$,
—CN,
—SO$_2$NR$^6$R$^7$,
—SO$_2$R$^4$
perfluoroalkyl, and
lower alkyl which is unsubstituted or substituted by the group consisting of —OR$^8$, —NR$^6$R$^7$, —COR$^4$, —COOR$^4$, and —CONR$^6$R$^7$;

R³ is selected from the group consisting of
—H,
—OR⁴,
—COR⁴,
—COOR⁴,
—CONR⁶R⁷,
halogen,
—CN,
—NR⁶R⁷,
perfluoroalkyl, and
lower alkyl which is unsubstituted or substituted by the group consisting of —OR⁸ and —NR⁶R⁷;

R⁴ is selected from the group consisting of
—H,
lower alkyl which is unsubstituted or substituted by the group consisting of —OR⁵, —COOR⁸, —COR⁸, —CONR⁸R⁹, —NR⁶R⁷, cycloalkyl, heterocycle, —CN, —NO₂, —SO₂R⁸, and —SO₂NR⁸R⁹,
cycloalkyl which is unsubstituted or substituted by the group consisting of —OR⁵, —COOR⁸, —COR⁸, —CONR⁸R⁹, —NR⁶R⁷, lower alkyl, heterocycle, —CN, —NO₂, —SO₂R⁸, and —SO₂NR⁸R⁹, and
heterocycle which is unsubstituted or substituted by the group consisting of —OR⁵, —COOR⁸, —COR⁸, —CONR⁸R⁹, —NR⁶R⁷, lower alkyl, cycloalkyl, —CN, —NO₂, —SO₂R⁸, and —SO₂NR⁸R⁹;

R⁵ is selected from the group consisting of
—H,
—COR⁸,
—CONR⁸R⁹, and
lower alkyl which is unsubstituted or substituted by the group consisting of —OR⁹, —NR⁹R¹⁰, —N(COR⁹)R¹⁰, —COR⁹, —CONR⁹R¹⁰, and —COOR⁹;

R⁶ and R⁷ are each independently selected from the group consisting of
—H,
—COR⁸,
—COOR⁸,
—CONR⁸R⁹,
—SO₂R⁸,
—SO₂NR⁸R⁹,
lower alkyl which is unsubstituted or substituted by the group consisting of
—OR⁵,
—COOR⁸,
—COR⁸,
—CONR⁸R⁹,
—CN,
—NO₂,
—SO₂R⁸,
—SO₂NR⁸R⁹,
—NR⁸R⁹,
cycloalkyl which is unsubstituted or substituted by the group consisting of —OR⁵, —COOR⁸, —COR⁸, —CONR⁸R⁹, —NR⁸R⁹, lower alkyl, heterocycle, —CN, —NO₂, —SO₂R⁸, and —SO₂NR⁸R⁹,
heterocycle which is unsubstituted or substituted by the group consisting of —OR⁵, —COOR⁸, —COR⁸, —CONR⁸R⁹, —NR⁸R⁹, lower alkyl, cycloalkyl, —CN, —NO₂, —SO₂R⁸, and —SO₂NR⁸R⁹,
aryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹, and
heteroaryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹,
cycloalkyl which is unsubstituted or substituted by the group consisting of —OR⁵, —COOR⁸, —COR⁸, —CONR⁸R⁹, —NR⁸R⁹, lower alkyl, heterocycle, —CN, —NO₂, —SO₂R⁸, and —SO₂NR⁸R⁹,
heterocycle which is unsubstituted or substituted by the group consisting of —OR⁵, —COOR⁸, —COR⁸, —CONR⁸R⁹, —NR⁸R⁹, lower alkyl, cycloalkyl, —CN, —NO₂, —SO₂R⁸, and —SO₂NR⁸R⁹,
aryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹,
heteroaryl which is unsubstituted or substituted by the group consisting of —OR⁵, —COOR⁸, —COR⁸, —CONR⁸R⁹, —NR⁸R⁹, lower alkyl, cycloalkyl, heterocycle, —CN, —NO₂, —SO₂R⁸, and —SO₂NR⁸R⁹, and
—NR⁶R⁷ can form a ring having 3 to 7 atoms, said ring not including any additional hetero atoms or including one or more additional hetero atoms and being unsubstituted or substituted by the group consisting of one or more of lower alkyl, —OR⁵, —COR⁸, —COOR⁸, CONR⁸R⁹, and —NR⁵R⁹;

R⁸ is selected from the group consisting of
—H,
lower alkyl which is unsubstituted or substituted by the group consisting of cycloalkyl, heterocycle, aryl, heteroaryl, —OR⁹, —NR⁹R¹⁰, and —N(COR⁹)R¹⁰,
aryl which is unsubstituted or substituted by the group consisting of —OR⁹, —COOR⁹, —COR⁹, —CONR¹⁰R⁹, —NR¹⁰R⁹, lower alkyl, cycloalkyl, heterocycle, —CN, —NO₂, —SO₂R⁹, halogen, —SO₂F and —SO₂NR¹⁰R⁹,
heteroaryl which is unsubstituted or substituted by the group consisting of —OR⁹, —COOR⁹, —COR⁹, —CONR¹⁰R⁹, —NR¹⁰R⁹, lower alkyl, cycloalkyl, heterocycle, —CN, —NO₂, —SO₂R⁹, halogen, —SO₂F and —SO₂NR¹⁰R⁹,
cycloalkyl which is unsubstituted or substituted by the group consisting of —OR⁹, —COOR⁹, —COR⁹, —CONR¹⁰R⁹, —NR¹⁰R⁹, lower alkyl, heterocycle, aryl, —CN, —NO₂, —SO₂R⁹, and —SO₂NR¹⁰R⁹, and
heterocycle which is unsubstituted or substituted by the group consisting of —OR⁹, —COOR⁹, —COR⁹, —CONR¹⁰R⁹, —NR¹⁰R⁹, lower alkyl, cycloalkyl, aryl, —CN, —NO₂, —SO₂R⁹, and —SO₂NR¹⁰R⁹;

R⁹ and R¹⁰ are each independently selected from the group consisting of —H, lower alkyl and aryl; and X is selected from the group consisting of =N— and

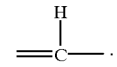

21. The compound of claim 20 wherein, R¹, R¹' and R¹'' are each independently selected from the group consisting of
—H,
—OR⁴,
—COR⁴, —COOR⁴,
—CONR⁶R⁷,
—NR⁶R⁷,
—SO₂R⁴,
—SO₂NR⁶R⁷, and
lower alkyl which is unsubstituted or substituted by the group consisting of —OR⁵ and —NR⁶R⁷,
cycloalkyl which is unsubstituted or substituted by the group consisting of —OR⁵ and —NR⁶R⁷, and
heterocycle which is unsubstituted or substituted by the group consisting of —OR⁵ and —NR⁶R⁷; and
R³ is selected from the group consisting of
—H,
—OR⁴,
—NR⁶R⁷,
—lower alkyl which is unsubstituted or substituted by the group consisting of —OR⁸ and —NR⁶R⁷.

22. The compound of claim 2 wherein A is heteroaryl.
23. The compound of claim 22 wherein A is indole or indole substituted with R¹.
24. The compound (Z)-1,3-Dihydro-4-iodo-3-[(1H-pyrrol-2-yl)methylene]-2H-indol-2-one.
25. A compound selected from the group consisting of
(Z)-1,3-Dihydro-4-phenyl-3-[(1H-pyrrol-2-yl)methylene]-2H-indol-2-one (A),
(Z)-4-(3-Aminophenyl)-1,3-dihydro-3-[(1H-pyrrol-2-yl)methylene]-2H-indol-2-one (C),
(Z)-4-(3-Aminophenyl)-1,3-dihydro-3-[(1H-pyrrol-2-yl)methylene]-2H-indol-2-one hydrochloride salt (D),
(Z)-1,3-Dihydro-4-(4-methoxyphenyl)-3-[(1H-pyrrol-2-yl)methylene]-2H-indol-2-one (E),
(Z)-1,3-Dihydro-4-(3-nitrophenyl)-3-[(1H-pyrrol-2-yl)methylene]-2H-indol-2-one (F),
(Z)-1,3-Dihydro-3-[(1H-pyrrol-2-yl)methylene]-4-(3-trifluoromethylphenyl)-2H-indol-2-one (G),
(Z)-1,3-Dihydro-4-(4-methylphenyl)-3-[(1H-pyrrol-2-yl)methylene]-2H-indol-2-one (H),
(Z)-1,3-Dihydro-4-(2-methylphenyl)-3-[(1H-pyrrol-2-yl)methylene]-2H-indol-2-one (I),
(Z)-4-(2,4-Dichlorophenyl)-1,3-dihydro-3-[(1H-pyrrol-2-yl)methylene]-2H-indol-2-one (J),
(Z)-4-(4-Chlorophenyl)-1,3-dihydro-3-[(1H-pyrrol-2-yl)methylene]-2H-indol-2-one (L),
(Z)-1,3-Dihydro-4-(2-methoxyphenyl)-3-[(1H-pyrrol-2-yl)methylene]-2H-indol-2-one (M),
(Z)-1,3-Dihydro-4-(1-naphthalenyl)-3-[(1H-pyrrol-2-yl)methylene]-2H-indol-2-one (N),
(Z)-4-(3-Chlorophenyl)-1,3-dihydro-3-[(1H-pyrrol-2-yl)methylene]-2H-indol-2-one (P),
(Z)-1,3-Dihydro-4-(4-hydroxyphenyl)-3-[(1H-pyrrol-2-yl)methylene]-2H-indol-2-one (R),
(Z)-4-(3-Aminophenyl)-1,3-dihydro-3-[(3-methoxy-1H-pyrrol-2-yl)methylene]-2H-indol-2-one (EE),
(Z)-1,3-Dihydro-4-phenyl-3-[(3-methoxy-1H-pyrrol-2-yl)methylene]-2H-indol-2-one (GG), and
(Z)-1,3-Dihydro-4-(4-hydroxyphenyl)-3-[(3-methoxy-1H-pyrrol-2-yl)methylene]-2H-indol-2-one (HH).

26. A compound selected from the group consisting of
(Z)-4-[2,3-Dihydro-2-oxo-3-[(1H-pyrrol-2-yl)methylene]-1H-indol-4-yl]-benzoic acid (Q),
(Z)-3-[2,3-Dihydro-2-oxo-3-[(1H-pyrrol-2-yl)methylene]-1H-indol-4-yl]-benzoic acid (BB),
(Z)-4-[2,3-Dihydro-3-[(3-methoxy-1H-pyrrol-2-yl)methylene]-2-oxo-1H-indol-4-yl]-benzoic acid (II),
(Z)-4-[2,3-Dihydro-3-[(3-methoxy-1H-pyrrol-2-yl)methylene]-5-nitro-2-oxo-1H-indol-4-yl]-benzoic acid methyl ester (RR),
(Z)-4-[5-Amino-2,3-dihydro-3-[(3-methoxy-1H-pyrrol-2-yl)methylene]-2-oxo-1H-indol-4-yl]-benzoic acid methyl ester (SS),
(Z)-4-[2,3-Dihydro-3-[(3-methoxy-1H-pyrrol-2-yl)methylene]-2-oxo-5-[(2-thienylacetyl)amino]-1H-indol-4-yl]-benzoic acid methyl ester (WW),
(Z)-4-[2,3-Dihydro-3-[(3-methoxy-1H-pyrrol-2-yl)methylene]-2-oxo-5-[(2-thienylacetyl)amino]-1H-indol-4-yl]-benzoic acid (XX),
(Z)-4-[2,3-Dihydro-5-fluoro-3-[(4-methyl-1H-imidazol-5-yl)methylene]-2-oxo-1H-indol-4-yl]-benzoic acid methyl ester trifluoroacetate salt (AAA).

27. A compound selected from the group consisting of
(Z)-N-[3-[2,3-Dihydro-2-oxo-3-[(1H-pyrrol-2-yl)methylene]-1H-indol-4-yl]-phenyl]-4-hydroxybenzamide (S),
(Z)-N-[3-[2,3-Dihydro-2-oxo-3-[(1H-pyrrol-2-yl)methylene]-1H-indol-4-yl]-phenyl]-3-bromobenzamide (T),
(Z)-N-[3-[2,3-Dihydro-2-oxo3-[(1H-pyrrol-2-yl)methylene]-1H-indol-4-yl]-phenyl]-3-cyanobenzamide (U),
(Z)-N-[3-[2,3-Dihydro-2-oxo-3-[(1H-pyrrol-2-yl)methylene]-1H-indol-4-yl]-phenyl]-3-nitrobenzamide (V),
(Z)-N-[3-[2,3-Dihydro-2-oxo-3-[(1H-pyrrol-2-yl)methylene]-1H-indol-4-yl]-phenyl]-4-fluorobenzamide (W),
(Z)-N-[3-[2,3-Dihydro-2-oxo-3-[(1H-pyrrol-2-yl)methylene]-1H-indol-4-yl]-phenyl]-4-nitrobenzamide (X),
(Z)-N-[3-[2,3-Dihydro-2-oxo-3-[(1H-pyrrol-2-yl)methylene]-1H-indol-4-yl]-phenyl]-4-methoxybenzamide (Y),
(Z)-4-Amino-N-[3-[2,3-dihydro-2-oxo-3-[(1H-pyrrol-2-yl)methylene]-1H-indol-4-yl]phenyl]cyclohexanecarboxamide (Z),
(Z)-N-[3-[2,3-Dihydro-2-oxo-3-[(1H-pyrrol-2-yl)methylene]-1H-indol-4-yl]-phenyl]-4-(fluorosulfonyl)benzamide (AA),
(Z)-N-[2-[[3-[2,3-Dihydro-2-oxo-3-[(1H-pyrrol-2-yl)methylene]-1H-indol-4-yl]phenyl]amino]-2-oxoethyl]-4-(fluorosulfonyl)benzamide (CC).

28. A compound selected from the group consisting of
(Z)-1,3-Dihydro-3-[(1H-pyrrol-2-yl)methylene]-4-(2-thiophenyl)-2H-indol-2-one (B),
(Z)-1,3-Dihydro-4-(2,4-dimethoxy-6-pyrimidinyl)-3-[(3-methoxy-1H-pyrrol-2-yl)methylene]-2H-indol-2-one (FF),
(Z)-1,3-Dihydro-4-(5-indolyl)-3-[(3-methoxy-1H-pyrrol-2-yl)methylene]-2H-indol-2-one (MM),
(Z)-1,3-Dihydro-4-(5-indolyl)-3-[(3-methoxy-1H-pyrrol-2-yl)methylene]-5-nitro-2H-indol-2-one,
(Z)-5-Amino-1,3-dihydro-4-(5-indolyl)-3-[(3-methoxy-1H-pyrrol-2-yl)methylene]-2H-indol-2-one,
(Z)-N-[2,3-Dihydro-4-(5-indolyl)-3-[(3-methoxy-1H-pyrrol-2-yl)methylene]-2-oxo-1H-indol-5-yl]-2-thiopheneacetamide (QQ),
(Z)-1,3-Dihydro-4-(4-indolyl)-3-[(3-methoxy-1H-pyrrol-2-yl)methylene]-2H-indol-2-one (TT), (Z)-1,3-Dihydro-4-(6-indolyl)-3-[(3-methoxy-1H-pyrrol-2-yl)methylene]-2H-indol-2-one (UU), (Z)-1,3-Dihydro-4-(6-indolyl)-3-[(3methoxy-1H-pyrrol-2-yl)methylene]-5-nitro-2H-indol-2-one, (Z)-5-Amino-1,3-dihydro-4-(6-indolyl)-3-[(3-methoxy-1H-pyrrol-2-yl)methylene]-2H-indol-2-one, and (Z)-N-[2,3-Dihydro-4-(6-indolyl)-3-[(3-methoxy-1H-pyrrol-2-yl)methylene]-2-oxo-1H-indol-5-yl]-2-thiopheneacetamide (VV).

29. A compound selected from the group consisting of
(Z)-N-[3-[2,3-Dihydro-2-oxo-3-[(1H-pyrrol-2-yl)methylene]-1H-indol-4-yl]phenyl]methanesulfonamide (K), (Z)-N-[3-[2,3-Dihydro-2-oxo-3-[(1H-pyrrol-2-yl)methylene]-1H-indol-4-yl]phenyl]-2-thiophenesulfonamide (O), and (Z)-N-[3-[2,3-Dihydro-2-oxo-3-[(1H-pyrrol-2-yl)methylene]-1H-indol-4-yl]phenyl]-4-(phenylsulfonyl)-2-thiophenesulfonamide (DD).

30. A compound selected from the group consisting of
(Z)-1,3-Dihydro-4-(4-hydroxyphenyl)-3-[(3-methoxy-1H-pyrrol-2-yl)methylene]-5-nitro-2H- indol-2-one (JJ), (Z)-1,3-Dihydro--[(3-methoxy-1H-pyrrol-2-yl)methylene]-5-nitro-4-phenyl-2H-1 indol-2-one (KK), (Z)-N-[2,3-Dihydro-3-[(3-methoxy-1H-pyrrol-2-yl)methylene]-2-oxo-4-phenyl-1H-indol-5-yl]-2-thiopheneacetamide (LL), (Z)-5-Amino-1,3-dihydro-4-(4-hydroxyphenyl) -3-[(3-methoxy-1H-pyrrol-2-yl)methylene]-2H-indol-2-one (NN), (Z)-N-[2,3-Dihydro-4-(4-hydroxyphenyl)-3-[(3-methoxy-1H-pyrrol-2-yl)methylene]-2-oxo-1H-indol-5-yl]-2-thiopheneacetamide (OO), (Z)-5-Amino-1,3-dihydro-3-[(3-methoxy-1H-pyrrol-2-yl)methylene]-4-phenyl-2H-indol-2-one (PP), (Z)-1,3-Dihydro-3-[(4-methyl-1H-imidazol-5-yl)methylene]-5-nitro-4-phenyl-2H-indol-2-one (YY), and (Z)-1,3-Dihydro-5-fluoro-4-(4-hydroxyphenyl)-3-[(4-methyl-1H-imidazol-5-yl)methylene]-2H-indol-2-one trifluoroacetate salt (ZZ).

31. A compound selected from the group consisting of
(Z)-1,3-Dihydro-5-fluoro-4-(4-methoxyphenyl)-3-[(4-methyl-1H-imidazol-5-yl)methylene]-2H-indol-2-one trifluoroacetate salt (BBB), (Z)-1,3-Dihydro-4-(3,4-dimethoxyphenyl)-5-fluoro-3-[(4-methyl-1H-imidazol-5-yl)methylene]-2H-indol-2-one (CCC), (Z)-1,3-Dihydro-4-(2,4-dimethoxyphenyl)-5-fluoro-3-[(4-methyl-1H-imidazol-5-yl)methylene]-2H-indol-2-one (DDD), (Z)-4-(1,3-Benzodioxol-5-yl)-1,3-dihydro-5-fluoro-3-[(4-methyl-1H-imidazol-5-yl)methylene]-2H-indol-2-one trifluoroacetate salt (EEE), (Z)-4-(3-Aminophenyl)-1,3-dihydro-5-fluoro-3-[(4-methyl-1H-imidazol-5-yl)methylene]-2H-indol-2-one (FFF), (Z)-4-(3-Amino-4-methyl-phenyl)-1,3-dihydro-5-fluoro-3-[(4-methyl-1H-imidazol-5-yl)methylene]-2H-indol-2-one (GGG), (Z)-1,3-Dihydro-5-fluoro-4-(3-hydroxyphenyl)-3-[(4-methyl-1H-imidazol-5-yl)methylene]-2H-indol-2-one (HHH), (Z)-1,3-Dihydro-5-fluoro-4-(4-hydroxyphenyl)-3-[(1H-pyrrol-2-yl)methylene]-2H-indol-2-one (III), (Z)-1,3-Dihydro-5-fluoro-4-(4-hydroxyphenyl)-3-[(3-methoxy-1H-pyrrol-2-yl)methylene]-2H-indol-2-one (JJJ), 2-[3-[5-Fluoro-3-[(3-methoxy-1H-pyrrol-2-yl)methylene]-2-oxo-2,3-dihydro-1H-indol-4-yl]-phenylamino]-acetamide (KKK), and (Z)-1,3-Dihydro-5-fluoro-4-(4-hydroxymethyl-3-methoxy-phenyl)-3-[(3-methoxy-1H-pyrrol-2-yl)methylene]-2H-indol-2-one (LLL).

32. A pharmaceutical composition comprising as an active ingredient an effective amount of a compound of claim 2 and a pharmaceutically acceptable carrier or excipient.

33. The pharmaceutical composition of claim 32 which is suitable for parenteral administration.

34. A pharmaceutical composition comprising as an active ingredient an effective amount of a compound of claim 20 and a pharmaceutically acceptable carrier or excipient.

35. The pharmaceutical composition of claim 34 which is suitable for parenteral administration.

36. A method for treating an inflammatory disease comprising of administering to a subject in need thereof a therapeutically effective amount of a compound according to claim 2.

37. A method for treating an inflammatory disease comprising of administering to a subject in need thereof a therapeutically effective amount of a compound according to claim 20.

38. A method for treating a neurodegenerative disease comprising of administering to a subject in need thereof a therapeutically effective amount of a compound according to claim 2.

39. A method for treating a neuro-degenerative disease comprising of administering to a subject in need thereof a therapeutically effective amount of a compound according to claim 20.

40. A method for treating rheumatoid arthritis comprising of administering to a subject in need thereof a therapeutically effective amount of a compound according to claim 2.

41. A method for treating rheumatoid arthritis comprising of administering to a subject in need thereof a therapeutically effective amount of a compound according to claim 20.

\* \* \* \* \*

UNITED STATES PATENT AND TRADEMARK OFFICE
CERTIFICATE OF CORRECTION

PATENT NO. : 6,307,056 B1  Page 1 of 1
APPLICATION NO. : 09/464466
DATED : October 23, 2001
INVENTOR(S) : Wendy Lea Corbett, Kin-Chun Luk and Paige E. Mahaney It is certified that error appears in the above-identified patent and that said Letters Patent is hereby corrected as shown below:

IN THE CLAIMS:

- Claim 27, Column 74, line 25: "(Z)-N-[3-[2,3-Dihydro-2-oxo3-" should read -- (Z)-N-[3-[2,3-Dihydro-2-oxo-3- --.

- Claim 28, Column 75, line 3: "(Z)-1,3-Dihydro-4-(6-indolyl)-3-[(3methoxy-1H-pyrrol-" should read -- (Z)-1,3-Dihydro-4-(6-indolyl)-3-[(3-methoxy-1H-pyrrol- --.

- Claim 30, Column 75, line 26: "(Z)-1,3-Dihydro- -[(3-methoxy" should read -- (Z)-1,3-Dihydro-[(3-methoxy --.

Signed and Sealed this

First Day of April, 2008

JON W. DUDAS
*Director of the United States Patent and Trademark Office*